United States Patent
Hoye et al.

(10) Patent No.: US 11,111,206 B2
(45) Date of Patent: Sep. 7, 2021

(54) MONOMERS AND POLYMERS FORMED THEREBY

(71) Applicant: REGENTS OF THE UNIVERSITY OF MINNESOTA, Minneapolis, MN (US)

(72) Inventors: Thomas R. Hoye, St. Paul, MN (US); Nicolas Ball-Jones, Minneapolis, MN (US); Grant W. Fahnhorst, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 61 days.

(21) Appl. No.: 16/136,593

(22) Filed: Sep. 20, 2018

(65) Prior Publication Data

US 2019/0084915 A1    Mar. 21, 2019

Related U.S. Application Data

(60) Provisional application No. 62/560,867, filed on Sep. 20, 2017.

(51) Int. Cl.
*C07C 69/587* (2006.01)
*C07C 69/602* (2006.01)
(Continued)

(52) U.S. Cl.
CPC .......... *C07C 69/587* (2013.01); *C07C 51/02* (2013.01); *C07C 51/41* (2013.01); *C07C 51/60* (2013.01);
(Continued)

(58) Field of Classification Search
CPC ......... C07C 67/08; C07C 51/41; C07C 51/02; C07C 51/60; C07C 233/09; C07C 57/03;
(Continued)

(56) References Cited

U.S. PATENT DOCUMENTS 4,195,184 A * 3/1980 Kesling, Jr. ............ C07C 69/58
560/207
6,344,538 B1   2/2002 Sheares
(Continued)

FOREIGN PATENT DOCUMENTS

WO   WO 2014172596 A2   10/2014
WO   WO 2015161169 A1   10/2015

OTHER PUBLICATIONS

Abarbri, "Stereospecific synthesis of (Z) or (E)-3-methylalk-2-enoic acids" 1995 Tetrahedron Lett., 36:2469-2472.
(Continued)

*Primary Examiner* — Shane Fang
(74) *Attorney, Agent, or Firm* — Mueting Raasch Group

(57) ABSTRACT

Monomers, polymers, or oligomers formed therefrom and methods of forming or utilizing monomers of formula I

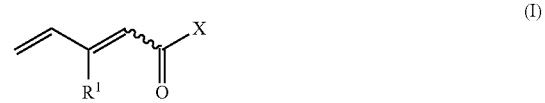

where $R^1$ is a $C_1$ to $C_4$ alkyl; and X is —OH; —OM where M is lithium (Li), sodium (Na), or potassium (K), $NH_4^+$, $R^5NH_3^+$, $R^5{}_2NH_2^+$, $R^5{}_3NH^+$, $R^5{}_4N^+$ where $R^5$ can independently be selected from alkyl, benzyl, and combinations thereof; —$OR^2$ where $R^2$ can be a $C_1$ to $C_4$ alkyl, 2-ethylhexyl, or a hydrocarbon moiety of bio-renewable alcohol or a hydrogenated derivative thereof; —$NR^3R^4$, —$NR^3$—$NR^3R^4$, —$NR^3$—$OR^4$ where $R^3$ and $R^4$ can independently be H, a $C_1$ to $C_4$ alkyl, or combinations thereof.

10 Claims, 30 Drawing Sheets

(51) Int. Cl.
| | |
|---|---|
| C07C 57/03 | (2006.01) |
| C07C 51/41 | (2006.01) |
| C08F 236/14 | (2006.01) |
| C08F 236/06 | (2006.01) |
| C08F 236/08 | (2006.01) |
| C08F 236/10 | (2006.01) |
| C08F 220/06 | (2006.01) |
| C07C 51/02 | (2006.01) |
| C07C 67/08 | (2006.01) |
| C07C 51/60 | (2006.01) |
| C07C 233/09 | (2006.01) |

(52) U.S. Cl.
CPC .............. *C07C 57/03* (2013.01); *C07C 67/08* (2013.01); *C07C 69/602* (2013.01); *C07C 233/09* (2013.01); *C08F 220/06* (2013.01); *C08F 236/06* (2013.01); *C08F 236/08* (2013.01); *C08F 236/10* (2013.01); *C08F 236/14* (2013.01); *C08F 2438/02* (2013.01)

(58) Field of Classification Search
CPC ..... C07C 57/66; C07C 69/587; C07C 69/602; C08F 236/14; C08F 236/10; C08F 236/06; C08F 236/08; C08F 220/06; C08F 4/04; C08F 2438/02
See application file for complete search history.

(56) References Cited

U.S. PATENT DOCUMENTS

| | | | |
|---|---|---|---|
| 8,178,719 | B2 | 5/2012 | Shima |
| 8,764,873 | B2 | 7/2014 | Nevin |
| 2016/0068877 | A1 | 3/2016 | Zhang |
| 2018/0355088 | A1* | 12/2018 | Ogawa ..................... C08L 33/04 |

OTHER PUBLICATIONS

Andreozzi, "Rheological and Thermal Properties of Narrow Distribution Poly(ethyl acrylate)s" 2006 Macromolecules, 39:1880-1889.
Arbuzova, "Vysokomolekulyarnye Soedineniya" 1970 Seriya A., 12:697-704.
Ball-Jones, "Poly(isoprenecarboxylates) from Glucose via Anhydromevalonolactone" Sep. 2016 ACS Macro Lett., 5(10):1128-1131.
Ball-Jones, "Supporting information for 'Poly(isoprenecarboxylates) from Glucose via Anhydromevalonolactone,'" 2016 ACS Macro Lett, S1-S40.
Benoit, "Development of a Universal Alkoxyamine for "Living" Free Radical Polymerizations" 1999 J. Am. Chem. Soc., 121:3904-3920.
Cornforth, "Studies on the biosynthesis of cholesterol. 5. Biosynthesis of squalene . . . " 1958 Biochem. J., 69:146-155.
De Jong, "Product developments in the bio-based chemicals arena" Oct. 2012 Biofuels, Bioproducts, and Biorefining, 6(6):606-624.
Dvornić, "The viscosity effect on autoacceleration of the rate of free radical polymerization" Aug. 1981 Polym. Eng. Sci., 21:792-796.
Fetters, "Connection between Polymer Molecular Weight, Density, Chain Dimensions, and Melt Viscoelastic Properties" 1994 Macromolecules, 27:4639-4647.
Hoye, "A Practical Guide to First-Order Multiplet Analysis in 1H NMR Spectroscopy" 1994 J. Org. Chem., 59:4096-4103.
Hoye, "A Method for Easily Determining Coupling Constant Values: An Addendum to 'A Practical Guide to First-Order Multiplet Analysis in 1H NMR Spectroscopy'" 2002 J. Org. Chem., 67(12):4014-4016.
Huguet, "Nickel-Catalyzed Direct Carboxylation of Olefins with CO2: One-Pot Synthesis of α,β-Unsaturated Carboxylic Acid Salts" 2014 Chem. Eur. J., 20:16858-16862.
Jenkins, "Terminology for reversible-deactivation radical polymerization previously called 'controlled' radical or 'living' radical polymerization (IUPAC Recommendations 2010)" 2009 Pure Appl. Chem., 82:483-491.
Manning, "The molecular theory of polyelectrolyte solutions with applications to the electrostatic properties of polynucleotides" 1978 Q. Rev. Biophys., 11:179-246.
Matsumoto, "Reaction principles and crystal structure design for the topochemical polymerization of 1,3-dienes" 2002 Angew. Chem. Int. Ed. Engl., 41:2502-2505.
Mauldin, "Acrylic Platform from Renewable Resources via a Paradigm Shift in Lactide Polymerization" 2016 ACS Macro Lett., 5:544-546.
Moriconi, "Reaction of dienes with chlorosulfonyl isocyanate" 1971 J. Org. Chem., 36:2841-2849.
Nakai, "The [2,3]Wittig rearrangement of 2-alkenyloxyacetic acids and its applications to the stereocontrolled synthesis of β, γ-unsaturated aldehydes and conjugated dienoic acids" 1981 Tetrahedron Lett., 22:69-72.
Paulus, "High Temperature Initiator-Free RAFT Polymerization of Methyl Methacrylate in a Microwave Reactor" 2009 U. S. Aust. J. Chem., 62(3):254-259.
Penzel,"Polyacrylates" in Ullmann's Encyclopedia of Industrial Chemistry; Wiley-VCH Verlag GmbH & Co. KGaA: Weinheim, Germany, 2000; vol. 28. Cover page, publisher page, pp. 515-536.
Schneiderman, "Chemically Recyclable Biobased Polyurethanes" 2016 ACS Macro Lett., 5:515-518.
Stickler, "Die thermische Polymerisation von Methylmethacrylat, 1. Polymerisation in Substanz" Nov. 1978 Makromol. Chem., 179:2729-2745.
Takasu, "Highly Threo Diastereoselective Anionic Polymerization of (E,E)-Methyl Sorbate Catalyzed by a Bulky Organoaluminum Lewis Acid" 2001 Macromolecules, 34:6548-6550.
Ueda, "Radical polymerization of methyl trans-β-vinylacrylate" 1995 J. Polym. Sci. A Polym. Chem., 33:1059-1067.
Xiong, "Scalable production of mechanically tunable block polymers from sugar" 2014 PNAS, 111:238357-8362.
Yamazaki, "Dynamic Viscoelasticity of Poly(butyl acrylate) Elastomers Containing Dangling Chains with Controlled Lengths" 2011 Macromolecules, 44(22):8829-8834.
Zhang, "Tough and Sustainable Graft Block Copolymer Thermoplastics" 2016 ACS Macro Lett., 5, 407-412.
Zhang, Supporting materials for "Tough and Sustainable Graft Block Copolymer Thermoplastics" 2016 ACS Macro Lett, 10 pages.

* cited by examiner

FIG. 1
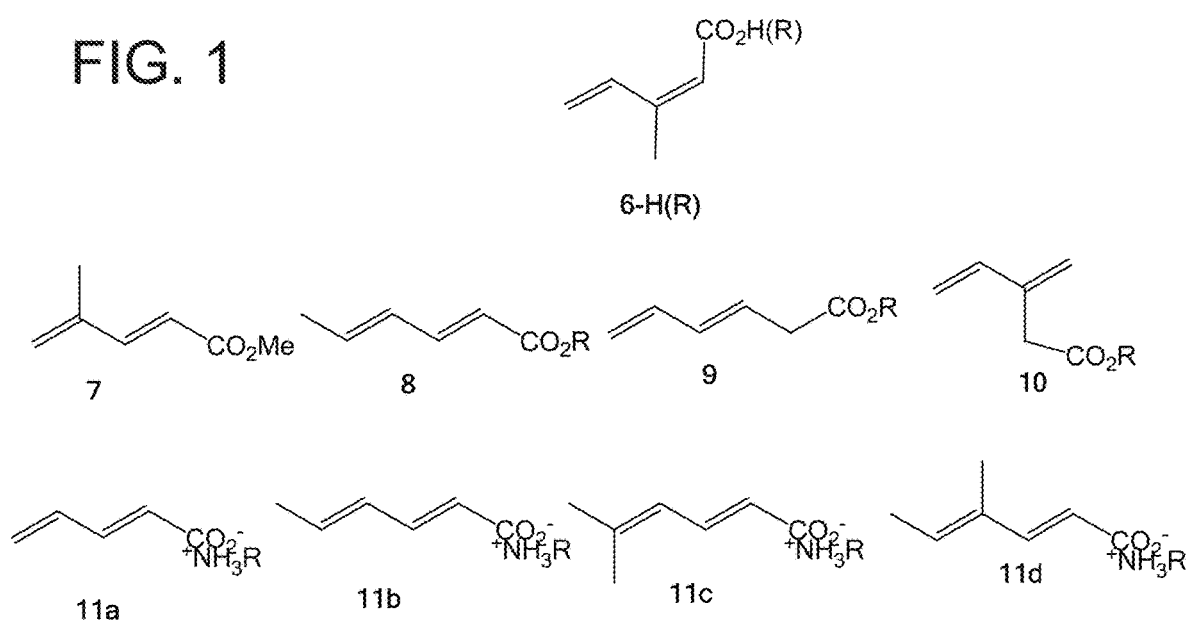
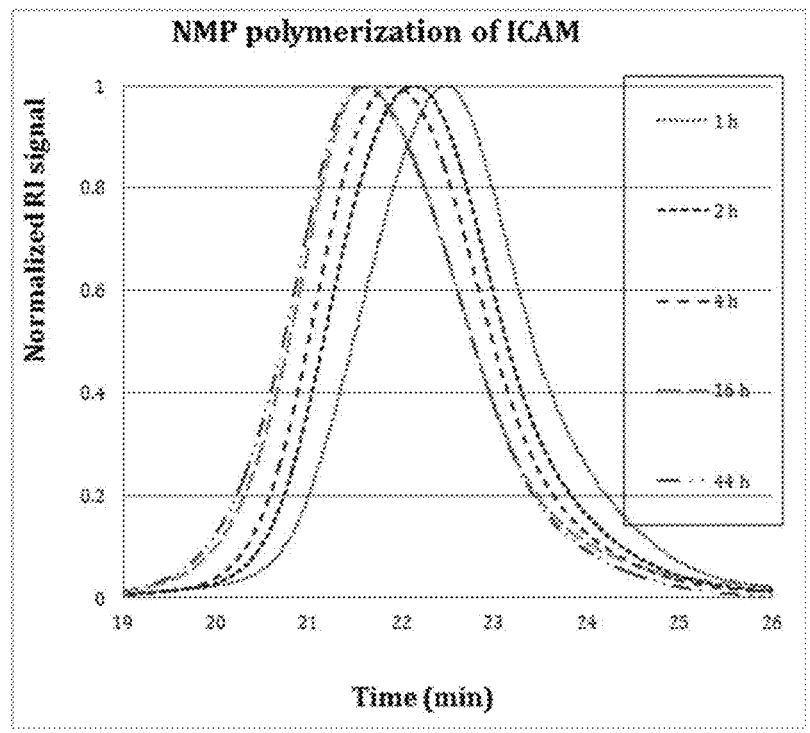
FIG. 2A

FIG. 3B
FIG. 3C
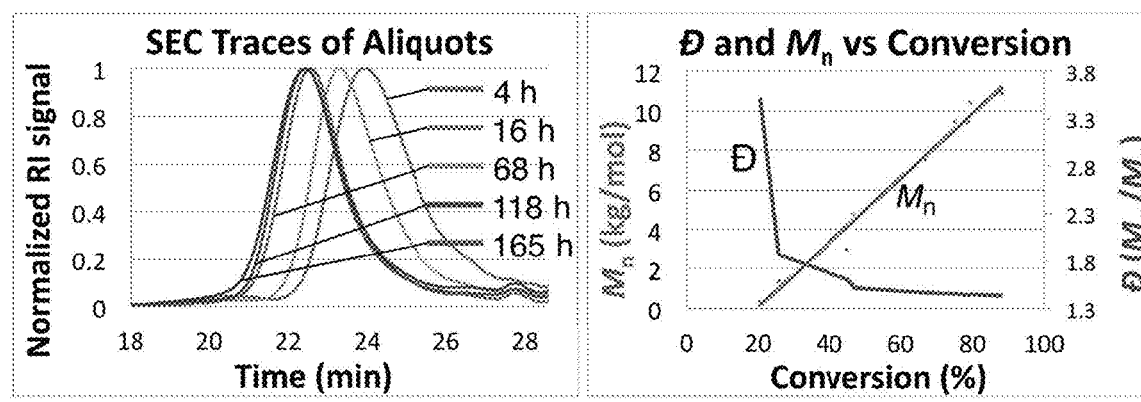
FIG. 4
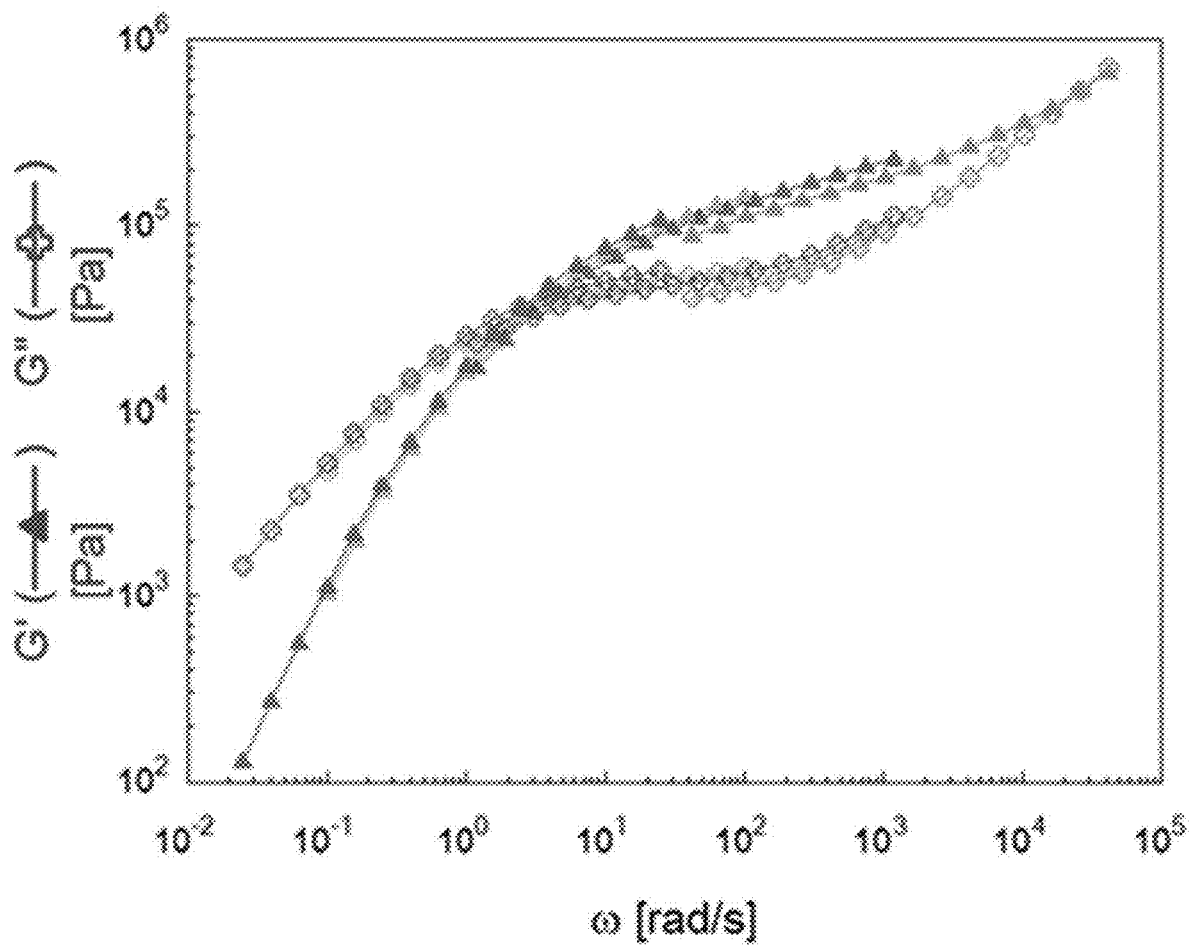

MONOMERS AND POLYMERS FORMED THEREBY

PRIORITY

This application claims priority to U.S. Provisional Application No. 62/560,867 filed on Sep. 20, 2017 entitled MONOMERS AND POLYMERS FORMED THEREBY, the disclosure of which is incorporated herein by reference thereto in its entirety.

GOVERNMENT FUNDING

This invention was made with government support under CHE-1413862 awarded by the National Science Foundation. The government has certain rights in the invention.

SUMMARY

Disclosed are monomers of formula I

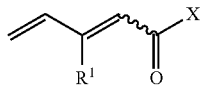

(I)

where $R^1$ is a $C_1$ to $C_4$ alkyl; and X is —OH; —OM where M is lithium (Li), sodium (Na), or potassium (K), $NH_4^+$, $R^5NH_3^+$, $R^5_2NH_2^+$, $R^5_3NH^+$, $R^5_4N^+$ where $R^5$ can independently be selected from alkyl, benzyl, and combinations thereof; —$OR^2$ where $R^2$ can be a $C_1$ to $C_4$ alkyl, 2-ethylhexyl, or a hydrocarbon moiety of bio-renewable alcohol or a hydrogenated derivative thereof; —$NR^3R^4$, —$NR^3$—$NR^3R^4$, —$NR^3$—$OR^4$ where $R^3$ and $R^4$ can independently be H, a $C_1$ to $C_4$ alkyl, or combinations thereof.

Disclosed are polymers formed from one or more monomers of formula I

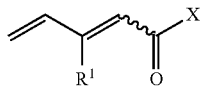

(I)

where $R^1$ is a $C_1$ to $C_4$ alkyl; and X is —OH; —OM where M is lithium (Li), sodium (Na), or potassium (K), $NH_4^+$, $R^5NH_3^+$, $R^5_2NH_2^+$, $R^5_3NH^+$, $R^5_4N^+$ where $R^5$ can independently be selected from $C_1$-$C_4$ alkyl, benzyl, cetyl, and other alkyl moieties found in commonly utilized ammonium ions; —$OR^2$ where $R^2$ can be a $C_1$ to $C_4$ alkyl, 2-ethylhexyl, or a hydrocarbon moiety of bio-renewable alcohol or a hydrogenated derivative thereof; —$NR^3R^4$, —$NR^3$—$NR^3R^4$, —$NR^3$—$OR^4$ where $R^3$ and $R^4$ can independently be H, a $C_1$ to $C_4$ alkyl, or combinations thereof.

Also disclosed are methods that include the steps of combining anhydromevalonolactone with a metal-tert-alkoxide in a solvent to form a carboxylate salt of formula I

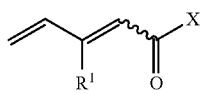

(I)

where $R^1$ is a $C_1$ to $C_4$ alkyl; and X is —OM where M is lithium (Li), sodium (Na), or potassium (K), $NH_4^+$, $R^5NH_3^+$, $R^5_2NH_2^+$, $R^5_3NH^+$, $R^5_4N^+$ where $R^5$ can independently be selected from $C_1$-$C_4$ alkyl, benzyl, cetyl, and other alkyl moieties found in commonly utilized ammonium ions; and treating the carboxylate salt of formula I with a mineral acid to form a mixture of the carboxylate salt of formula I and the acid thereof, wherein M is replaced with a hydrogen.

Also disclosed are monomers of formula II:

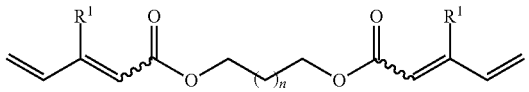

(II)

where $R^1$ is a $C_1$ to $C_4$ alkyl; and n is an integer from 0 to 6.

Also disclosed are monomers of formula III:

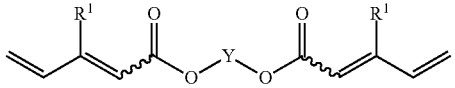

(III)

where $R^1$ is a $C_1$ to $C_4$ alkyl; and Y is a linker group.

The above summary of the invention is not intended to describe each disclosed embodiment or every implementation of the invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

BRIEF DESCRIPTION OF FIGURES

FIG. 1 shows isoprenecarboxylic acid (6-H) and its esters (6-R) which are described here and related dienoates (7-11).

FIGS. 2A and 2B show a normalized SEC chromatogram (FIG. 2A) and corresponding dispersity ($Đ$) and molecular weights (FIG. 2B) of aliquots taken from a nitroxide-mediated radical polymerization (NMP).

FIGS. 3A, 3B and 3C show RAFT polymerization of isoprenecarboxylates 6-R and conditions used for the polymerization of bulk samples of methyl (Z)-3-methylpenta-2,4-dienoate (6-Me), ethyl (Z)-3-methylpenta-2,4-dienoate (6-Et), butyl (Z)-3-methylpenta-2,4-dienoate (6-$^n$Bu), and tert-Butyl (Z)-3-Methylpenta-2,4-dienoate (6-$^t$Bu) (FIG. 3A); SEC of aliquots vs. time for polymerization of 6-Me (in the presence of 0.01 equiv of 12) showing a linear increase in molecular weight with % conversion (FIGS. 3B and 3C).

FIG. 4 shows Time-Temperature Superposition plot of poly(methyl isoprenecarboxylate) (PMIC) ($M_n$=152,000 g/mol) referenced at 110° C. ($T_g$=38° C.). Each of the two curves comprised of closed triangles and open crosses is a composite of four separate curves measured, respectively, at 70, 90, 100, and 125° C.

DETAILED DESCRIPTION OF ILLUSTRATIVE EMBODIMENTS

Figure 2B:
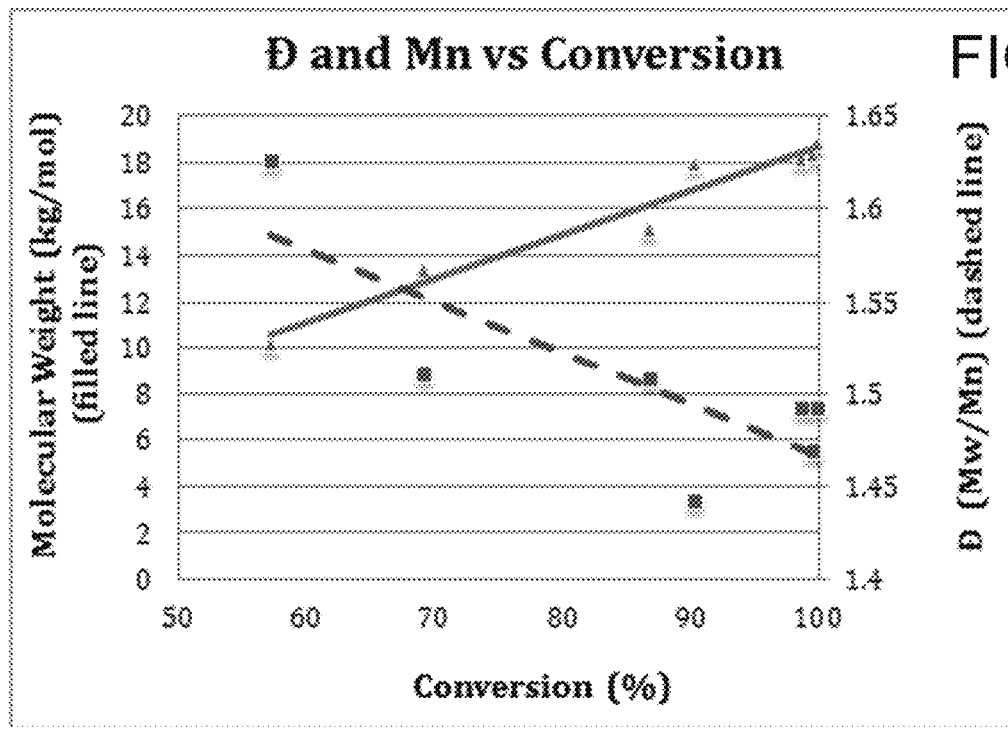

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one. Reference to "a carboxylic acid compound", for example, refers to a single carboxylic acid compound, multiple compounds of the same carboxylic acid compound, more than one specific carboxylic acid compound, multiple types of carboxylic acid compounds, mixtures of carboxylic acid compounds, or any combination thereof.

As used herein, "alkyl" is an unsubstituted or substituted saturated hydrocarbon chain radical having from 1 to about 12 carbon atoms; from 1 to about 10 carbon atoms; from about 1 to about 6 carbon atoms; or from about 1 to about 4 carbons. It should also be understood that an alkyl moiety can be a combination of two or more alkyl moieties. Illustrative, non-limiting examples of alkyl groups include, for example, methyl, ethyl, propyl, iso-propyl, and butyl. A $C_2$ to $C_4$ substituted or unsubstituted alkyl radical, for example refers to a $C_2$ to $C_4$ linear alkyl chain that may be unsubstituted or substituted. If the $C_2$ to $C_4$ linear alkyl chain is substituted with an alkyl radical, the carbon number of the alkyl radical increases as a function of the number of carbons in the alkyl substituent.

As used herein, "hydroxyl group" refers to a substituent group of formula —OH.

Unless otherwise stated, as employed herein, when a moiety (e.g., alkyl, or alkenyl) is described as "substituted" it is meant that the group optionally has from one to four, from one to three, or one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Referring to a compound herein refers to both enantiomeric versions of the compound. For example, referring to a compound refers to and includes both the Z- and E- isomers unless specifically stated otherwise.

In formulae herein, a squiggled bond (i.e., ～～～), which is used to designate the attachment of a carbonyl group to an alkene double bond, is taken to mean that the geometry of that bond can be either of Z- or E-configuration in the compound in question or a mixture of both geometric isomers of that compound.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order, unless context indicates otherwise. And, as appropriate, any combination of two or more steps may be conducted simultaneously.

All headings are for the convenience of the reader and should not be used to limit the meaning of the text that follows the heading, unless so specified.

Disclosed herein are monomers and compounds produced from such monomers. Disclosed monomers can generally be described as a dienoate or derivatives thereof. In some embodiments, disclosed monomers can be formed using anhydromevalonolactone (compound 3 below) as a starting material. In some embodiments, anhydromevalonolactone can be subjected to eliminative opening under the action of potassium tert-butoxide, sodium ethoxide, or combinations thereof (which may proceed via the intermediate 5 and an E1cB mechanism) to produce compound 6 (shown below) which can then be subjected to Fischer esterification with an alcohol to produce desired monomers (referred to in the description of Scheme 2 as "isoprenecarboxylate esters"). This scheme is demonstrated below

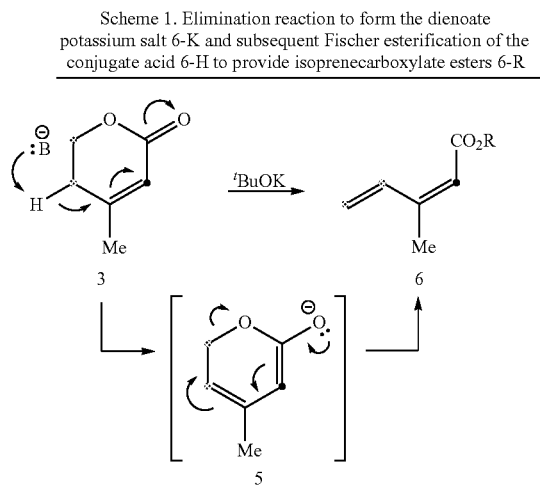

Scheme 1. Elimination reaction to form the dienoate potassium salt 6-K and subsequent Fischer esterification of the conjugate acid 6-H to provide isoprenecarboxylate esters 6-R More specifically, disclosed herein is the preparation of a series of esters and derivatives thereof that can be derived from 6-H. Cornforth first demonstrated (Cornforth, J. W.; Cornforth, R. H.; Popjak, G.; Gore, I. Y. Biochem. J. 1958, 69, 146-155) the eliminative opening of lactone 3, most likely via 5 and an E1cB mechanism, under the action of potassium tert-butoxide (Scheme 1). Acidification gives the acid 6-H. The potassium salt 6-K can be routinely prepared and isolated on multi-ten-gram scales. The non-nucleophilic bases NaOiPr, sodium acetate, or 1,8-diazabicyclo[5.4.0]undec-7-ene (DBU) can also effect this transformation. Other known methods for accessing this penta-2,4-dienoic acid may be less advantageous from a preparative point of view: e.g. cross-coupling of alkenylstannanes (Abarbri, M.; Parrain, J.-L.; Duchene, A. Tetrahedron Lett. 1995, 36, 2469-2472), multi-step sequences (Nakai, T.; Mikami, K.; Taya, S.; Kimura, Y; Mimura, T. Tetrahedron Lett. 1981, 22, 69-72), or generation as a mixture of 3- and 4-methylpentadienoic acids from isoprene (uguet, N.; Jevtovikj, I.; Gordillo, A.; Lejkowski, M. L.; Lindner, R.; Bru, M.; Khalimon, A. Y.; Rominger, F.; Schunk, S. A.; Hofmann, P.; Limbach, M. Chem. Eur. J. 2014, 20, 16858-16862). Fischer esterification of 6-H with any of the alcohols, for example MeOH, EtOH, or n-BuOH can give, following distillation, each of the esters 6-Me, 6-Et, and 6-$^n$Bu, respectively, in the yield indicated in Scheme 1. Alternatively, the tert-butyl ester 6-$^t$Bu can be prepared by suspension of 6-H in isobutylene and treatment with $H_2SO_4$ as a Brønsted acid catalyst.

In some embodiments, the starting material, anhydromevalolactone (compound 3) may be obtained from any type of source. In some embodiments, the starting material, anhydromevalolactone (compound 3) may be obtained from renewable feedstocks. In some embodiments, this can be accomplished using a bioengineered process. The synthesis of polymers from renewable feedstocks is of growing importance to a sustainable society. Disclosed methods, monomers and polymers may capitalize on the ready availability of mevalonate (1), for which an efficient bioengineered preparation via fermentation of glucose has recently been developed in the Zhang laboratory (Xiong, M.; Schneiderman, D. K.; Bates, F. S.; Hillmyer, M. A.; Zhang, K. Proc. Natl. Acad. Sci. 2014, 111, 8357-8362). The carboxylate 1 can be readily converted (Scheme 2) through acidification to mevalonolactone (2) and, in turn, anhydromevalonolactone (3). Simple hydrogenation then gives β-methyl-δ-valerolactone (βMδVL, 4). This saturated lactone has been demonstrated by investigators to be an effective monomer for ring-opening transesterification polymerization (ROTEP) enroute to valuable polyesters containing βMδVL (Xiong, M.; Schneiderman, D. K.; Bates, F. S.; Hillmyer, M. A.; Zhang, K. Proc. Natl. Acad. Sci. 2014, 111, 8357-8362. Zhang, J.; Li, T.; Mannion, A. M.; Schneiderman, D. K.; Hillmyer, M. A.; Bates, F. S. ACS Macro Lett. 2016, 5, 407-412. Schneiderman, D. K.; Vanderlaan, M. E.; Mannion, A. M.; Panthani, T. R.; Batiste, D. C.; Wang, J. Z.; Bates, F. S.; Macosko, C. W.; Hillmyer, M. A. ACS Macro Lett. 2016, 5, 515-518).

| R | | Yield | |
|---|---|---|---|
| 6-K | K | 89% | HCl |
| 6-H | H | 83% | |
| 6-Me | Me | 79% | ROH, HCl |
| 6-Et | Et | 59% | |
| 6-$^n$Bu | $^n$Bu | 82% | $H_2SO_4$ |
| 6-$^t$Bu | $^t$Bu | 79% | Isobutylene |

Scheme 2. The facile chemical conversion of mevalonate (1) to β-methyl-δ-valerolactone (βMδVL, 4) via mevalonolactone (2) and anhydromevalonolactone (3)

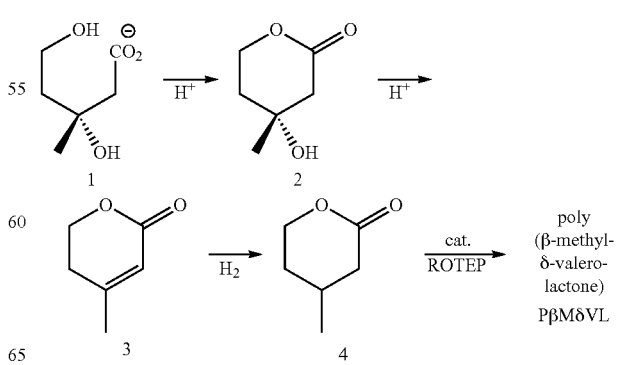

In some embodiments, the monomers can be of formula I below, where the Z- and E-alkene isomers, as well as mixtures thereof are included:

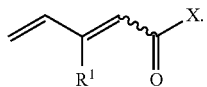

In formula I, $R^1$ can be a substituted or unsubstituted $C_1$ to $C_4$ alkyl. In some embodiments, $R^1$ can be more specifically described as a methyl group ($C_1$), an ethyl group ($C_2$), a propyl group ($C_3$) (e.g., an n-propyl group or an isopropyl group) or a butyl group ($C_4$) (e.g., an n-butyl, sec-butyl, isobutyl, or tert-butyl). In formula I, X can be —OH; —OM where M can be lithium (Li), sodium (Na), potassium (K), $NH_4^+$, $R^5NH_3^+$, $R^5_2NH_2^+$, $R^5_3NH^+$, $R^5_4N^+$ where $R^5$ can independently be selected from alkyl, benzyl (—$CH_2$Phenyl), or combinations thereof; $OR^2$ where $R^2$ can be a substituted or unsubstituted $C_1$ to $C_4$ alkyl (e.g., a methyl group ($C_1$), an ethyl group ($C_2$), a propyl group ($C_3$) (e.g., an n-propyl group or an isopropyl group) or a butyl group ($C_4$) (e.g., an n-butyl, sec-butyl, isobutyl, or tert-butyl), 2-ethylhexyl, or a hydrocarbon moiety of bio-renewable alcohol such as geranyl, phytyl, cholesteryl, sitosteryl, ergosteryl, recinoleyl, etc. (or the hydrogenated derivatives thereof); —$NR^3R^4$, —$NR^3$—$NR^3$—$R^4$, —$NR^3$—$OR^4$ where $R^3$ and $R^4$ can independently be H, or a substituted or unsubstituted $C_1$ to $C_4$ alkyl (e.g., a methyl group ($C_1$), an ethyl group ($C_2$), a propyl group ($C_3$) (e.g., an n-propyl group or an isopropyl group) or a butyl group ($C_4$) (e.g., an n-butyl, sec-butyl, isobutyl, or tert-butyl), or combinations thereof; halide (e.g., chloride ($Cl^-$), iodide (I), bromide (Br). In some embodiments, $R^5$ can be an alkyl moiety that is itself a combination of two or more alkyl moieties. In some embodiments $R^5$ can be an alkyl moiety found in commonly utilized ammonium ions. In some embodiments, $R^5$ can be a cetyl moiety.

In some embodiments starting materials for the monomers of formula I may be obtained via methods or processes described in United States Patent Publication Number US 2016/0068877, PCT Patent Application Publication Number WO 2015/161169, or both; the disclosures of which are incorporated herein by reference to the extent they do not conflict.

In some embodiments, the following combinations of $R^1$ and X may not be included in compounds of formula I: $R^1$ is methyl and X is —OH (both Z- and E-alkene isomers); $R^1$ is methyl and X is OM (both Z- and E-alkene isomers); $R^1$ is methyl and X is $OR^2$ where $R^2$ is methyl (both Z- and E-alkene isomers); $R^1$ is methyl and X is $OR^2$ where $R^2$ is ethyl (both Z- and E-alkene isomers); $R^1$ is methyl and X is $OR^2$ where $R^2$ is tert-butyl (both Z- and E-alkene isomers); $R^1$ is ethyl and X is —OH (both Z- and E-alkene isomers); $R^1$ is ethyl and X is $OR^2$ where $R^2$ is methyl (both Z- and E-alkene isomers); $R^1$ is ethyl and X is $OR^2$ where $R^2$ is ethyl (both Z- and E-alkene isomers); $R^1$ is methyl and X is —$NR^3R^4$ where both $R^3$ and $R^4$ are methyl (both Z- and E-alkene isomers); $R^1$ is methyl and X is —$NR^3R^4$ where both $R^3$ and $R^4$ are isopropyl (both Z- and E-alkene isomers); $R^1$ is methyl and X is —$NR^3R^4$ where both $R^3$ and $R^4$ are hydrogen (both Z- and E-alkene isomers); $R^1$ is n-propyl and X is —$NR^3R^4$ where both $R^3$ and $R^4$ are isopropyl (both Z- and E-alkene isomers) and); $R^1$ is methyl and X is chloride (both Z- and E-alkene isomers).

Also disclosed herein are polymers formed using one or more disclosed monomers, e.g., polymers, either homopolymers or copolymers, formed by polymerizing one or more compounds of formula I above. Polymers formed herein can be referred to as poly(isoprenecarboxylate) polymers, poly(isoprenecarboxylate) derivative polymers, or combinations thereof. Polymerization can be accomplished using any known methods, including for example radical polymerization, anionic polymerization, or combinations thereof. In some embodiments radical polymerization can be utilized. In some embodiments, reversible addition-fragmentation chain-transfer (RAFT) polymerization can be utilized. In some embodiments, nitroxide-mediated polymerization (NMP) can be utilized. Disclosed monomers can optionally be polymerized with a secondary monomer that is not a disclosed isoprenecarboxylate or derivative thereof monomer as well. In some embodiments, secondary monomers that can be polymerized (randomly, block, or combinations thereof) can include, for example petroleum-derived monomers including for example isoprene, butadiene and non-petroleum-derived monomers. In some embodiments, one or more disclosed monomers can be polymerized with one or more acid derivatives of one or more disclosed monomers. Such copolymerization can be utilized to form a hydrogel, for example.

Disclosed monomers can be utilized to form a hydrogel via inclusion in a copolymer. In some embodiments, a disclosed monomer(s) can form the majority (based on moles or weight, or both) monomer in a copolymer for use as a hydrogel. In some embodiments, disclosed monomer(s) can be polymerized and then cross linked to form a hydrogel. In some embodiments, disclosed monomer(s) can be polymerized and cross linked simultaneously to form a hydrogel. In some embodiments, the minority monomer can be difunctional or multifunctional crosslinking agent. In some embodiments, the minority monomer can be an acrylate monomer (or methacrylate monomer). In some embodiments, illustrative acrylate monomers can include bis-acrylates, tri-acrylates, tetra-acrylates (or methacrylates). Therefore, disclosed herein are copolymers formed from one or more monomers according to formula I above and one or more other monomers. In some embodiments, disclosed herein are copolymers formed from one or more monomers according to formula I above and itaconic acid or maleic acid or fumaric acid. In some embodiments, disclosed herein are copolymers formed from one or more monomers according to formula I above and one or more crosslinkable monomers. In some embodiments, disclosed herein are copolymers formed from one or more monomers according to formula I above and one or more acrylate or methacrylate containing monomers. In some embodiments, copolymers can be formed using at least 10 times the molar equivalent of the monomer of formula I as the crosslinkable monomer. In some embodiments, copolymers can be formed using at least 50 times the molar equivalent of the monomer of formula I as the crosslinkable monomer. In some embodiments, copolymers can be formed using at least 70 times the molar equivalent of the monomer of formula I as the crosslinkable monomer. In some embodiments, copolymers can be formed using at least 100 times the molar equivalent of the monomer of formula I as the crosslinkable monomer. In some embodiments, copolymers can be formed using at least 1000 times the molar equivalent of the monomer of formula I as the crosslinkable monomer. Disclosed hydrogels can be synthesized in, for example, a methanol/water solution or, even more advantageously, in water alone.

Also disclosed are monomers formed from monomers of formula I. In some embodiments, such monomers can be referred to as difunctional monomers. In some embodiments, such monomers can be of formula II below:

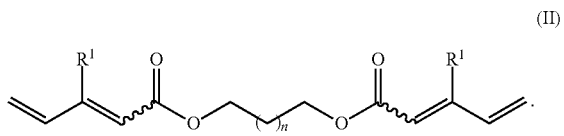

(II)

In formula II, $R^1$ can be a substituted or unsubstituted $C_1$ to $C_4$ alkyl. In some embodiments, $R^1$ can be more specifically described as a methyl group ($C_1$), an ethyl group ($C_2$), a propyl group ($C_3$) (e.g., an n-propyl group or an isopropyl group) or a butyl group ($C_4$) (e.g., an n-butyl, sec-butyl, isobutyl, or tert-butyl). In formula II, n can be an integer from 0 to 6.

Also disclosed are monomers formed from monomers of formula I and being of formula III below:

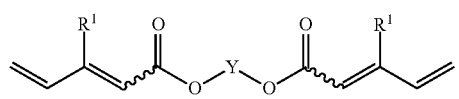

(III)

In formula III, $R^1$ can be a substituted or unsubstituted $C_1$ to $C_4$ alkyl. In some embodiments, le can be more specifically described as a methyl group ($C_1$), an ethyl group ($C_2$), a propyl group ($C_3$) (e.g., an n-propyl group or an isopropyl group) or a butyl group ($C_4$) (e.g., an n-butyl, sec-butyl, isobutyl, or tert-butyl). In formula III, Y is a linker group. In some embodiments, Y can be a linker group corresponding to a linker group commonly used in a bis-acrylate or bis-methacrylate crosslinking agent typically utilized in acrylate or methacrylate polymerization reactions. In some embodiments, Y can be a linker group comprising oligomeric ethylenoxy repeat units [Y=—(CH$_2$CH$_2$O)$_n$CH$_2$CH$_2$, where n=1-200]. In some embodiments, Y can be the linker group derived from 1,2-, 1,3-, or 1,4-benzenedimethanol.

Polymers formed from disclosed monomers can be swelled by combining them with an aqueous solution optionally including counterion(s) (e.g., Na$^+$, Li$^+$, K$^+$, or combinations thereof). Illustrative aqueous solutions can include deionized water (DI H$_2$O) alone or aqueous solutions containing Na$^+$, K$^{30}$, Ca$^{++}$, Mg$^{++}$ or combinations thereof. In some embodiments, 1% (weight/volume) aqueous solution of NaCl, KCl, or CaCl$_2$ can be utilized as a swelling solution.

As discussed above, disclosed polymers can function as or can have characteristics of a hydrogel. The particular properties of disclosed monomers or polymers can be affected based, at least in part, on the components making up the monomer or polymer formed thereby. For example, swelling properties of a polymer can be affected by the choice of counterion(s) in the monomer, the concentration of counterion(s) in a swelling solution, the identity of the crosslinking agent, the amount of the crosslinking agent, or combinations thereof.

In some embodiments, disclosed monomers can absorb or absorb and retain a greater amount of an aqueous solution such as a swelling solution than can a hydrogel made from acrylic acid when the two are prepared under substantially identical conditions. These monomers possess an increased distance between carboxylates. Due to this feature, the extent of "counterion condensation" (Manning, G. S. Q. Rev. Biophys.1978, 11, 179-246) may be reduced.

This disclosure is further illustrated by the following examples. It is to be understood that the particular examples, materials, amounts, and procedures are to be interpreted broadly in accordance with the scope and spirit of the disclosure as set forth herein.

EXAMPLES

Esters were prepared and polymerized in various ways, including under RAFT and NMP conditions, to provide a series of high molecular weight polymers. The glass transition temperature and entanglement molecular weight of each was determined. The ester alkyl group in these polymers affected the $T_g$ and $M_e$ in a very similar fashion as is known for simple poly(acrylates). This work established the feasibility of using glucose as a source of polymers with acrylate-like properties. Additionally, various alternative strategies are disclosed herein that capitalize on the ready availability of compounds 2-4 (in Scheme 1) in ways that might lead to additional novel monomers and/or polymers.

EXAMPLES

This disclosure is further illustrated by the following examples. It is to be understood that the particular examples, materials, amounts, and procedures are to be interpreted broadly in accordance with the scope and spirit of the disclosure as set forth herein.

General Experimental Protocols

Materials: Anhydrous tetrahydrofuran (THF), dichloromethane (DCM), and diethyl ether were taken immediately prior to use from a column of activated alumina. Reported reaction temperatures are the temperature of the external heating or cooling bath.

Instrumental Methods:

NMR: $^1$H and $^{13}$C NMR spectra were recorded on a Bruker Avance 500 (500 MHz) or a Varian Inova 500 (500 MHz) spectrometers. $^1$H NMR chemical shifts in CDCl$_3$ are referenced to TMS (δ 0.00 ppm). Non-first-order multiplets in $^1$H NMR spectra have been identified as 'nfom.' The following format is used to report resonances: chemical shift in ppm [multiplicity, coupling constant(s) in Hz, integral, and assignment]. $^1$H NMR assignments are indicated by the substructural environment (e.g., CH$_a$H$_b$). Coupling constant analysis was led by methods we have described elsewhere. $^{13}$C NMR chemical shifts for spectra recorded in CDCl$_3$ are referenced to the carbon resonance in CDCl$_3$ (δ 77.16).

ATR-FTIR: Fourier transform infrared (FTIR) spectra were recorded with a Bruker Alpha Platinum ATR-FTIR instrument (diamond single-bounce crystal). Typically 16 scans were acquired and a 4 s acquisition time was used.

Mass spectrometry of non-polymeric samples: MS measurements were made using electron impact ionization on an Agilent 5975 MSD at 70 eV GC-MS. The column stationary phase was an Agilent HP-5 with a 0.25 μm film thickness, 30 m long, ×0.32 mm i.d.

Size Exclusion Chromatography (SEC): SEC was conducted on a liquid chromatograph (Agilent 1100 series) fitted with a refractive index detector (HP1047A). Polymer samples were dissolved in CHC13 (1-2 mg·mL-1) and eluted through three successive Varian PLgel Mixed C columns (7.5 mm id; 25 cm 1) at 35° C. at a flow rate of 1 mL·min-1. Dispersity and mass-average molar mass of the samples were referenced to polystyrene standards.

Thermogravimetric Analysis (TGA): TGA was performed (TA Instruments Q500) at a heating rate of 10° C.·min-1 under an atmosphere of nitrogen. The sample size was 5-15 mg.

Differential Scanning Calorimetry (DSC): Differential scanning Calorimetry (TA Instruments Q-1000 DSC) was performed on samples hermetically sealed in aluminum pans. Each sample was heated to 250° C., cooled to –60° C., and reheated to 250° C. Glass transition temperatures were taken as the inflection point and are reported as measured on the second (or third) heating cycle.

Linear Viscosity (Rheology) Measurements: A 0.50 g sample of solid polymer was placed onto the bottom rheometer plate (2.5 cm d) held at the desired reference temperature (70° C. above the Tg). The top plate was manually lowered under a steady rate sweep at a frequency of 0.1/s for approximately 2 full rotations to prepare the sample for the measurements. A dynamic strain sweep was taken at this temperature to ensure linearity within the sample. The dynamic linear viscoelastic measurements were carried out within the linear viscoelastic regime at temperatures in the range from 10 to 125° C. The dynamic measurements were conducted in the range of 0.1-100 rad/s at a strain of 1%. A gap of approximately 1.0 mm was used to minimize edge effects. The rheological measurements were carried out under an atmosphere of nitrogen to minimize oxidative events of the polymer samples during testing. Entanglement molecular weights were approximated using the equation $$M_e = \frac{4}{5}\frac{\rho RT}{G_N}.$$

The plateau moduli were calculated using the minimum of tan delta vs G'.

Preparation of Monomers

A series of four esters of isoprenecarboxylic acid (6-H) that differed in the size of the ester alkyl moiety were prepared herein as shown in Scheme 1. The parent acid was made by an eliminative opening of anhydromevalonolactone (3), a commodity efficiently available in large quantities from glucose (Xiong, M.; Schneiderman, D. K.; Bates, F. S.; Hillmyer, M. A.; Zhang, K. Proc. Natl. Acad. Sci. 2014, 111, 8357-8362).

FIG. 1 shows isoprenecarboxylic acid (6-H) and its esters (6-R), specific examples of some monomers described here and related dienoates (7-11) that are known and have been previously polymerized. (Z)-3-Methylpenta-2,4-dienoic acid (or isoprenecarboxylic acid, 6-H, FIG. 1) has been prepared from anhydromevalonolactone (3) (Cornforth, J. W.; Cornforth, R. H.; Popjak, G.; Gore, I. Y Biochem. J. 1958, 69, 146-155. Moriconi, E. J.; Meyer, W. C. J. Org. Chem. 1971, 36, 2841-2849). Disclosed herein is the first reported polymerization of 6-H or any of its esters (6-R). In contrast, 4-methylpenta2,4-dienoate (7) (Arbuzova, I. A.; Efremova, V. N.; Eliseeva, A. G.; Mikhailova, N. V.; Nikitin, V. N.; Sidorovich, A. V.; Klushin, N. A.; Kuvshinskii, E. V. Vysokomolekulyarnye Soedineniya, Seriya A. 1970, 12, 697-704), sorbic acid esters (8) (For example, Takasu, A.; Ishii, M.; Inai, Y.; Hirabayashi, T. Macromolecules 2001, 34, 6548-6550), pentadienoates (9) (Ueda, M.; Shimada, S.; Ogata, T.; Oikawa, K.; Ito, H.; Yamada, B. J. Polym. Sci. A Polym. Chem. 1995, 33, 1059-1067), and 3-methylene-4-pentenoates (U.S. Pat. No. 6,344,538) have all been polymerized under one or more of radical, anionic, or cationic conditions. Light-induced topochemical polymerizations of the related dienoate salts 11a-d have also been described (Matsumoto, A.; Sada, K.; Tashiro, K.; Miyata, M.; Tsubouchi, T.; Tanaka, T.; Odani, T.; Nagahama, S.; Tanaka, T.; Inoue, K.; Saragai, S.; Nakamoto, S. Angew. Chem. Int. Ed. Engl. 2002, 41, 2502-2505). All of these unsymmetrical dienic monomers can, in principle, give rise to a variety of regioisomeric relationships in the derived polymeric backbones. For example, methyl penta-2,4-dienoate (9 or β-vinylacrylate) has been radically polymerized to give a homopolymer comprising an 85:15 mixture of backbone repeat units arising from competitive 1,4- vs. 1,2-addition (Ueda, M.; Shimada, S.; Ogata, T.; Oikawa, K.; Ito, H.; Yamada, B. J. Polym. Sci. A Polym. Chem. 1995, 33, 1059-1067). Finally, we also note the recent work of Boday and coworkers who polymerized "methylidenelactide", whose structure is given below and pointed out that this compound was one of only a few examples of acrylate-like monomers in which all atoms are bio-derived (the others arising from itaconic or levulinic acid or via bioengineered routes to acrylic acid from sugars) (Mauldin, T. C.; Wertz, J. T.; Boday, D. J. ACS Macro Lett. 2016, 5, 544-546).

Cornforth first demonstrated (Cornforth, J. W.; Cornforth, R. H.; Popjak, G.; Gore, I. Y. Biochem. J. 1958, 69, 146-155) the eliminative opening of lactone 3, most likely via 5 and an E1cB mechanism, under the action of potassium tert-butoxide (see Scheme 1). Alternatively, sodium ethoxide (NaOEt), an economically advantageous base, can be used in place of potassium tert-butoxide (KOtBu). Acidification gives the acid 6-H. The potassium salt 6-K has been routinely prepared and isolated on multi-ten-gram scales. The non-nucleophilic bases NaOiPr or 1,8-diazabicyclo[5.4.0]undec-7-ene (DBU) also effect this transformation. Other known methods for accessing this penta-2,4-dienoic acid may have drawbacks from a preparative point of view: e.g. cross-coupling of alkenylstannanes (Abarbri, M.; Parrain, J.-L.; Duchene, A. Tetrahedron Lett. 1995, 36, 2469-2472), multi-step sequences (Nakai, T.; Mikami, K.; Taya, S.; Kimura, Y; Mimura, T. Tetrahedron Lett. 1981, 22, 69-72), or generation as a mixture of 3- and 4-methylpentadienoic acids from isoprene (uguet, N.; Jevtovikj, I.; Gordillo, A.; Lejkowski, M. L.; Lindner, R.; Bru, M.; Khalimon, A. Y; Rominger, F.; Schunk, S. A.; Hofmann, P.; Limbach, M. Chem. Eur. J. 2014, 20, 16858-16862). Fischer esterification of 6-H with any of the alcohols MeOH, EtOH, or n-BuOH gave, following distillation, each of the esters 6-Me, 6-Et, and 6-$^n$Bu, respectively, in the yield indicated in Scheme 1. Alternatively, the tert-butyl ester 6-$^t$Bu was prepared by suspension of 6-H in isobutylene and treatment with $H_2SO_4$ as a Brønsted acid catalyst.

Specific Illustrative Syntheses (Z)-3-Methylpenta-2,4-dienoic acid (6-H)

This compound was synthesized following a modified literature procedure ((a) Moriconi, E. J.; Meyer, W. C. J. Org. Chem. 1971, 36, 2841-2849. (b) Cornforth, J. W.; Cornforth, R. H.; Popjak, G.; Gore, I. Y. Biochem. J. 1958, 69, 146-155)

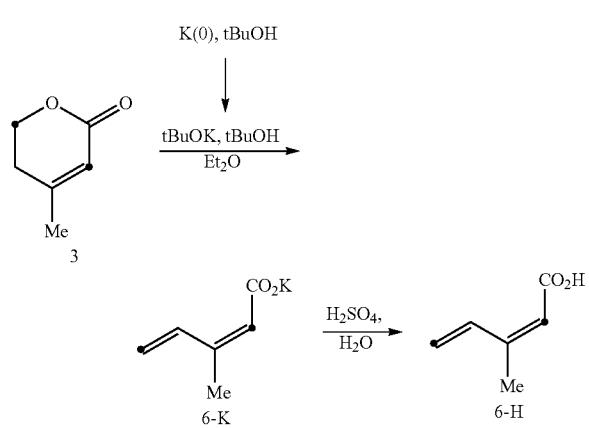

To a 50 mL two-neck round bottom flask equipped with a stir bar was added potassium metal (1.08 equiv, 0.487 g, 12.5 mmol), followed by dry, warm tert-butanol (10.1 equiv, 11.2 mL, 117 mmol). A bubbler was affixed to allow for the escape of hydrogen gas and the mixture was stirred under a slight positive pressure of nitrogen. After one hour at room temperature, the mixture was heated to 80° C. and stirred for 21 h until complete dissolution of the solid potassium had occurred. This solution of potassium tert-butoxide (1.06 M) was added rapidly to a stirring solution of 4-methyl-5,6-dihydro-2H-pyran-2-one (3, 1 equiv, 1.3 g, 11.6 mmol) in diethyl ether (8 mL). Immediate appearance of a precipitate was observed. The solid was collected by filtration (1.77 g). Analysis by $^1$H NMR spectroscopy (D$_2$O) indicated the solid to contain potassium (Z)-3-methylpenta-2,4-dienoate (6-K), potassium formate (a few percent), and potassium (Z)-5-hydroxy-3-methylpent-2-enoate. The purity of 6-K was judged to be ca. 90%.

Alternatively, commercially available potassium tert-butoxide was used to synthesize 6-K. Anhydromevalanolactone (3, 1 equiv, 6.06 g, 54.1 mmol) was dissolved in diethyl ether (15 mL) and added to a cooled (0° C.) solution of tert-butoxide (6.67 g, 59.6 mmol) in tert-butanol (20 mL) and diethyl ether (15 mL) in a 250 mL round bottom flask. A precipitate formed nearly immediately. After being stirred for approximately 10 minutes, the slurry was filtered, and the solid was rinsed thoroughly with diethyl ether. The crude mixture (8.70 g) was recovered as a tan solid. Similar purity was observed as described above. This material was used without further purification. (The yield of acid 6-H, obtained by the acidification procedure described below, was 5.34 g or 88%.)

The salt 6-K (35 g) was dissolved in water (200 mL) and diethyl ether (100 mL) was added. Aqueous hydrochloric acid was added to this mixture until the pH of the aqueous portion fell to ca. 3). The aqueous portion was extracted with additional diethyl ether. The combined organic layers were dried over MgSO$_4$, filtered, and concentrated to provide acid 6-H (20 g, 77% yield).

The material could be molecularly distilled in a sublimation apparatus held at ca. 210° C. at ca. 1 torr, or alternatively it could be recrystallized from a mixture of ethanol and water Acid (6-H) was found to be somewhat sensitive to light and was stored in the dark.

$^1$H NMR (500 MHz, CDCl$_3$) δ 12.06 (br s, CO$_2$H), 7.80 (ddd, J=17.6, 10.9, 0.9 Hz, 1H, CH$_2$=CHR), 5.76 (br dq, J=1.4, 1.4 Hz, 1H, =CHCO$_2$H), 5.65 (ddd, J=17.6, 1.3, 0.8 Hz, 1H, CH$_Z$H$_E$=CHR), 5.49 (ddd, J=10.9, 1.4, 1.4 Hz, 1H, CH$_Z$H$_E$=CHR), and 2.05 (d, J=1.3 Hz, 3H).

$^{13}$C NMR (125 MHz, CDCl$_3$) δ 171.8, 153.5, 133.9, 121.6, 117.5, and 20.6.

IR (neat, selected peaks): 2984, 2962, 1684, 1633, 1587, and 1427, 1395 cm$^{-1}$.

mp: 68-73° C.

GC-MS (30 m×0.25 mm ID, HP-5, 50° C./2.0 min/20° C. min$^{-1}$/250° C.) t$_R$=3.38 min; MS [70 eV, m/z (rel int)]: 112 (96, M$^+$), 111 (100, M$^+$-H), 97 (62, M$^-$-Me), and 94 (36, M$^+$-H$_2$O).

Methyl (Z)-3-Methylpenta-2,4-dienoate (6-Me)

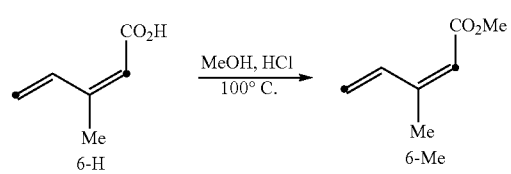

To an 80 mL screw cap topped culture tube equipped with a stir bar was added methanol (28 equiv, 25 mL, 0.6 mol) and thionyl chloride (25 mol %, 0.4 mL, 5.51 mmol). After five minutes, (Z)-3-methylpenta-2,4-dienoic acid (1 equiv, 2.44 g, 21.8 mmol) was added followed by phenothiazine (7 mol %, 0.03 g, 0.15 mmol). The tube was capped and stirred at 76° C. for 18 h and allowed to cool. The contents were added to a saturated solution of sodium bicarbonate (100 mL) followed by extraction with diethyl ether (100 mL×3). The organic layers were combined, dried (MgSO$_4$), and concentrated in vacuo. $^1$H NMR analysis of an aliquot of this crude reaction product indicated that all of the acid had been consumed. This material was distilled at ambient temperature under reduced pressure (1.5 torr) into a flask cooled in a −78° C. bath to afford methyl (Z)-3-methylpenta-2,4-dienoate (6-Me, 2.18 g, 17.3 mmol, 79% yield). Visual inspection of the reaction mixture when no phenothiazine was added led us to conclude that polymerization had occurred.

$^1$H NMR (500 MHz, CDCl$_3$) δ 7.81 (ddd, J=17.6, 10.9, 0.8 Hz, 1H, CH$_2$=CHR), 5.74 (qddd, J=1.4, 1.4, 0.7, 0.7 Hz, 1H, =CHCO$_2$Me), 5.61 (br ddd, J=17.6, 1.3, 0.7 Hz, 1H, CH$_Z$H$_E$=CHR), 5.47 (ddd, J=10.9, 1.5, 1.5 Hz, 1H, CH$_Z$H$_E$=CHR), 3.72 (s, 3H, OMe), and 2.02 (d, J=1.4 Hz, 3H, =CMe).

$^{13}$C NMR (125 MHz, CDCl$_3$) δ 166.6, 151.0, 134.0, 120.8, 117.8, 51.2, and 20.4.

IR (neat, selected peaks): 3095, 1710, 1637, and 1590 cm$^{-1}$.

GC-MS (30 m×0.25 mm ID, HP-5, 50° C./2.0 min/20° C. min$^{-1}$/250° C.) t$_R$=2.73 min; MS [70 eV, m/z (rel int)]: 126 (100, M$^+$), 125 (80, M$^+$-H), 111 (72, M$^+$-Me), 95 (99, M$^+$-OMe), and 67 (99, M$^+$-CO$_2$Me).

Ethyl (Z)-3-Methylpenta-2,4-dienoate (6-Et)

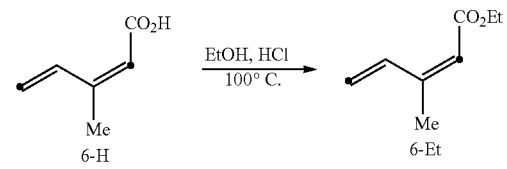

To an 80 mL screw cap topped culture tube equipped with a stir bar was added ethanol (19 equiv, 50 mL, 0.85 mol) and thionyl chloride (24 mol %, 0.8 mL, 11 mmol). After five minutes, (Z)-3-methylpenta-2,4-dienoic acid (1 equiv, 4.7 g, 43 mmol) was added followed by phenothiazine (3 mol %, 0.03 g, 0.15 mmol). The tube was capped and stirred at 86° C. for 18 h and allowed to cool. The contents were added to a saturated solution of sodium bicarbonate (100 mL) and then extracted with diethyl ether (100 mL×3). The organic layers were combined, dried (MgSO$_4$), and concentrated in vacuo. This material was distilled at 35° C. under reduced pressure (1.5 torr) into a flask cooled in a −78° C. bath to afford ethyl (Z)-3-methylpenta-2,4-dienoate (6-Et, 3.52 g, 25.2 mmol, 59% yield, 91:9 mixture of Z:E isomers).

$^1$H NMR (500 MHz, CDCl$_3$) δ 7.81 (ddd, J=17.6, 10.9, 0.8 Hz, 1H, CH$_2$=CHR), 5.72 (qddd, J=1.4, 1.4, 0.8, 0.8 Hz, 1H, =CHCO$_2$Me), 5.59 (br ddd, J=17.6, 1.3, 0.7 Hz, 1H, CH$_Z$H$_E$=CHR), 5.45 (ddd, J=10.9, 1.4, 1.4 Hz, 1H, CH$_Z$H$_E$=CHR), 4.17 (q, J=7.1 Hz, 2H, OCH$_2$CH$_3$), 2.00 (d, J=1.4 Hz, 3H, =CMe), and 1.28 (t, J=7.1 Hz, 3H, OCH$_2$CH$_3$).

$^{13}$C NMR (125 MHz, CDCl$_3$) δ 166.1, 150.6, 133.9, 120.5, 118.1, 59.8, 20.2, and 14.3.

IR (neat, selected peaks): 2977, 1710, 1634, and 1590 cm$^{-1}$.

GC-MS (30 m×0.25 mm ID, HP-5, 50° C./2.0 min/20° C. min$^{-1}$/250° C.) t$_R$=3.48 min; MS [70 eV, m/z (rel int)]: 140 (57, M$^+$), 139 (10, M$^+$-H), 112 (75, M$^-$-CH$_2$=CH$_2$), 111 (78, M$^+$-Et), 95 (100, M$^+$-OEt), and 67 (99, M$^+$-CO$_2$Et).

Butyl (Z)-3-Methylpenta-2,4-dienoate (6-$^n$Bu)

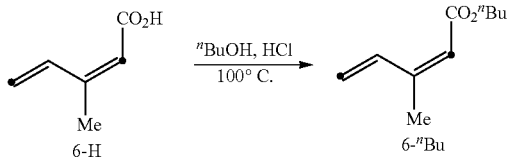

Thionyl chloride (0.13 equiv, 1 mL, 13.8 mmol) was added in dropwise fashion to a 200 mL heavy-walled glass pressure tube containing n-butanol (10 equiv, 100 mL, 1.08 mol). The tube was capped and the mixture was stirred for five minutes to allow generation of anhydrous HCl. (Z)-3-Methylpenta-2,4-dienoic acid (1 equiv, 4.7 g, 42 mmol) was added in one portion. The pressure tube was recapped and heated to 100° C. After 18 h the mixture was allowed to cool, and the butanol solution was partitioned between saturated potassium carbonate (100 mL) and methylene chloride. The aqueous layer was extracted 3× with dichloromethane, and the organic layers were combined, dried over MgSO$_4$, and concentrated. Phenothiazine (0.1 g) was added to minimize polymerization and this material was distilled under reduced pressure to afford butyl (Z)-3-methylpenta-2,4-dienoate (6-$_n$Bu, 4.8 g, 34.3 mmol, 81.7% yield, 86:14 mixture of Z:E isomers ($^1$H NMR analysis)).

$^1$H NMR (500 MHz, CDCl$_3$) δ 7.81 (ddd, J=17.6, 10.9, 0.8 Hz, 1H, CH$_2$=CHR), 5.73 (qddd, J=1.4, 1.4, 0.7, 0.7 Hz, 1H, =CHCO$_2$Me), 5.59 (br ddd, J=17.6, 1.3, 0.7 Hz, 1H, CH$_Z$H$_E$=CHR), 5.44 (ddd, J=10.9, 1.4, 1.4 Hz, 1H, CH$_Z$H$_E$=CHR), 4.11 (t, J=6.7 Hz, 2H, OCH$_2$CH$_2$), 2.00 (d, J=1.3 Hz, 3H, =CMe), 1.64 (br pent, J=7.1 Hz, 2H, OCH$_2$CH$_2$CH$_2$), 1.40 (br sextet, J=7.5 Hz, 2H, CH$_2$CH$_2$CH$_3$), and 0.94 (t, J=7.4 Hz, 3H, CH$_2$CH$_3$).

$^{13}$C NMR (125 MHz, CDCl$_3$) δ 166.2, 150.5, 134.0, 120.5, 118.2, 63.8, 30.8, 20.3, 19.3 and 13.7.

IR (neat, selected peaks): 3095, 2959, 2878, 1709, 1636, 1591, 1460, and 1381 cm$^{-1}$.

bp: 65° C. (1.5 torr).

GC-MS (30 m×0.25 mm ID, HP-5, 50° C./2.0 min/20° C. min$^{-1}$/250° C.) t$_R$=5.08 min; MS [70 eV, m/z (rel int)]: 168 (10, M$^+$), 112 (78, M$^+$-butene), 111 (57, M$^+$-Bu), 95 (51, M$^+$-OBu), and 67 (31, M$^+$-CO$_2$Et).

tert-Butyl (Z)-3-Methylpenta-2,4-dienoate (6-$^t$Bu)

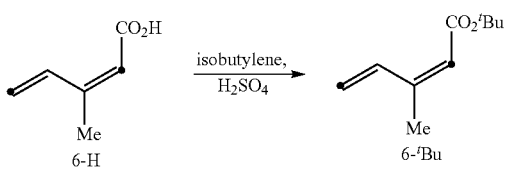

(Z)-3-Methylpenta-2,4-dienoic acid (3.00 g, 26.7 mmol) was added to an 80 mL screw cap culture tube equipped with a stir bar. The solution was cooled to −78° C. and isobutylene (15 equivalents, 38 mL, 400 mmol), which had been pre-condensed in a graduated cylinder, was added. Concentrated sulfuric acid (0.2 equivalents, 280 µL, 5.34 mmol) was added, the culture tube was capped, and the mixture was stirred for 7 h at 35° C. No starting 6-H remained ($^1$H NMR analysis). The culture tube was cooled to −78° C., opened, and approximately 20 mL of diethyl ether and 20 mL of saturated sodium bicarbonate (gas evolution) were added. The mixture was allowed to warm to ambient temperature to allow for slow evaporation of excess isobutylene over ca. 1 h while stirring. The remaining contents were diluted into ca. 100 mL of diethyl ether, washed with saturated sodium bicarbonate and brine, dried (MgSO$_4$), and concentrated to leave a yellow oil (4.73 g). Phenothiazine (0.1 g) was added and this crude material was distilled under reduced pressure (0.7 torr) to afford tert-butyl (Z)-3-methylpenta-2,4-dienoate (6-$^t$Bu, 3.54 g, 21.7 mmol, 78.9% yield).

$^1$H NMR (500 MHz, CDCl$_3$) δ 7.77 (ddd, J=17.6, 10.9, 0.9 Hz, 1H, CH$_2$=CHR), 5.66 (qddd, J=1.4, 1.4, 0.7, 0.7 Hz, 1H, =CHCO$_2$Me), 5.57 (br ddd, J=17.6, 1.4, 0.8 Hz, 1H, CH$_Z$H$_E$=CHR), 5.40 (ddd, J=10.9, 1.5, 1.5 Hz, 1H, CH$_Z$H$_E$=CHR), 1.97 (d, J=1.3 Hz, 3H, =CMe), and 1.48 (s, 9H, O(CH$_3$)$_3$).

$^{13}$C NMR (125 MHz, CDCl$_3$) δ 165.7, 149.4, 134.1, 120.2, 120.1, 80.1, 28.4, and 20.3.

IR (neat, selected peaks): 2987, 1706, 1637, and 1591 cm$^{-1}$.

bp: 27° C. (0.7 torr).

GC-MS (30 m×0.25 mm ID, HP-5, 50° C./2.0 min/20° C. min$^{-1}$/250° C.) t$_R$=4.10 min; MS [70 eV, m/z (rel int)]: 112 (100, M$^+$-isobutylene), 111 (55, M$^+$-C(Me)$_3$), 95 (63, M$^+$-O$^t$Bu), and 67 (24, M$^+$-CO$_2$$^t$Bu).

Carboxamides

Isoprenecarboxamides 6-AM can be synthesized from the isoprenecarboxylic acid (6-H). These can be made by initial conversion to the isoprenecarboxylic acid chloride (6-Cl) and then reacted with either of ammonia or a primary or secondary amine.

Synthesis of Isoprenecarboxamides

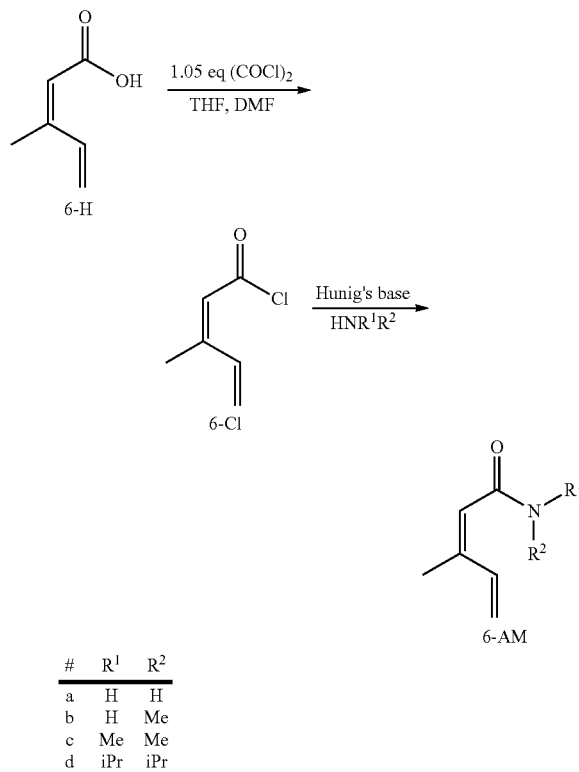

| # | R¹ | R² |
|---|----|----|
| a | H | H |
| b | H | Me |
| c | Me | Me |
| d | iPr | iPr |

As one example, (Z)-3-methylpenta-2,4-dienoic acid (6-H, 1.0 equiv, 1.50 g, 13.3 mmol), THF (20 mL), and DMF (50 mL) were added to a 6-dram vial fitted with a stir bar. Oxalyl chloride (1.1 equiv, 1.30 mL, 14.7 mmol) was added dropwise over the course of 10 minutes. Once bubbling had ceased, an aliquot was taken and the reaction progress was evaluated via $^1$H NMR analysis. The formation of acid chloride 6-Cl was judged to be complete. At this point, Hunig's base (1 equiv, 2.30 mL, 13.3 mL) was added followed by cold, liquefied dimethylamine (5.6 equiv, ca. 5.0 mL, 74 mmol) at 0° C. Stirring slowed almost immediately as a precipitate appeared, and THF (10 mL) was added to allow for continued stirring for 20 minutes. Excess solvent and reagents were removed in vacuo and the remaining mixture was taken up in DCM, washed with 0.1 M HCl, brine, dried (MgSO$_4$), and concentrated to give 1.67 g of (Z)-N,N,3-trimethylpenta-2,4-dienamide (6-AMc) as a yellow oil. The liquid was distilled twice (77° C., 0.1 mmHg) to give the material (960 mg, 6.7 mmol, 50% yield) as a clear liquid.

Polymerization

The compounds synthesized above were then polymerized using various methods.

First azobisisobutyronitrile (AIBN) was used to initiate a polymerization of methyl isoprenecarboxylate (6-Me) (Scheme 3) to provide poly(methyl isoprenecarboxylate) (PMIC). This reaction was examined both in the bulk and in methanol at varying initial monomer concentrations. This demonstrated that 6-Me behaves in a similar fashion to other conjugated dienoates (FIG. 1). $^1$H and $^{13}$C NMR analysis of the PMIC suggested that the polymerization occurs via competing 1,4- and 1,2-addition modes in a ratio of ca. 1.5:1. Additionally, the broad nature of nearly all resonances were indicative of the likely formation of multiple diastereomeric relationships among the new stereogenic alkene (E/Z) and sp$^3$ carbon atoms (R/S) that arise from the addition of each monomer.

Scheme 3. Free radical polymerization of 6-Me, initiated by AIBN as both a neat sample and in MeOH solution

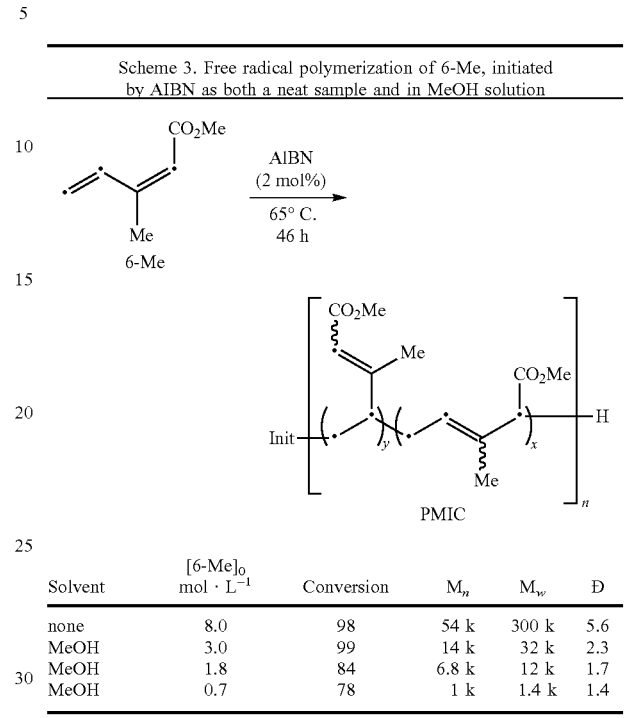

| Solvent | [6-Me]$_0$ mol · L$^{-1}$ | Conversion | $M_n$ | $M_w$ | Đ |
|---------|---------------------------|------------|-------|-------|-----|
| none | 8.0 | 98 | 54 k | 300 k | 5.6 |
| MeOH | 3.0 | 99 | 14 k | 32 k | 2.3 |
| MeOH | 1.8 | 84 | 6.8 k | 12 k | 1.7 |
| MeOH | 0.7 | 78 | 1 k | 1.4 k | 1.4 |

Procedure for AIBN Initiated Free Radical Polymerization of (Z)-3-methylpenta-2,4-dienoate (6-Me)

A stock solution of methyl (Z)-3-methylpenta-2,4-dienoate (6-Me, 0.21 g, 1.66 mmol) and (E)-2,2'-(diazene-1,2-diyl)bis(2-methylpropanenitrile) (AIBN, 4.1 mg, 0.025 mmol) was prepared. After the full dissolution of AIBN in the diene, the stock solution was dispensed into a series of 2 mL ampules (51 mg each). To each of these was added one of four solvents (benzene, acetonitrile, toluene, and methanol; 0.12 mL). The ampule was degassed through a series of three freeze-pump-thaw cycles and sealed under vacuum with a torch. The ampule was heated at 65° C. for 48 h. The ampule was allowed to cool to ambient temperature and a portion of the contents was analyzed by $^1$H NMR spectroscopy to determine the conversion. The remainder of the reaction mixture was freed of solvent in vacuo and then analyzed by SEC to determine the molecular weight and dispersity.

Reactivity of methyl (Z)-3-Methylpenta-2,4-dienoate (6-Me) Versus ethyl hexa-2,4-dienoate A competition experiment was also carried out in which the two diene monomers 6-Me and ethyl sorbate (ethyl hexa-2,4-dienoate) were copolymerized to partial (ca. 50%) conversion under AIBN initiation in order to gain some insight about the relative reactivity of the two. Although overlap of resonances from each of the unreactive monomers and the copolymer product made it difficult to obtain precise quantitative assessment, it was concluded that the 6-Me was consumed about 4 times faster than the ethyl sorbate. This is consistent with an expected easier approach of any propagating radical to the unsubstituted methylene carbon (C5) of the monomer 6-Me compared to attack at C5 of ethyl sorbate.

Procedure for competition experiment for the copolymerization of ethyl sorbate and (Z)-3-methylpenta-2,4-dienoate (6-Me) (Scheme 4)

To a 2 mL ampule was added (E)-2,2'-(diazene-1,2-diyl)bis(2-methylpropanenitrile) (AIBN, 1 equiv, 2 mg, 0.01 mmol) followed by methyl (Z)-3-methylpenta-2,4-dienoate (6-Me, ca. 80 mg, 0.6 mmol) and ethyl sorbate (ca. 90 mg, 0.6 mmol). After full dissolution of the AIBN at ambient temperature, an aliquot of the mixture was taken that showed ($^1$H NMR) a 44:56 molar mixture of 6-Me:ethyl sorbate. The ampule was degassed through a series of three freeze-pump-thaw cycles and sealed under vacuum with a torch. The ampule was heated at 65° C. for 29 h. The ampule was allowed to cool to ambient temperature and the contents were analyzed by $^1$H NMR spectroscopy to determine the conversion, amounts of 6-Me and ethyl sorbate remaining, and the composition of the copolymer.

Ethyl sorbate is somewhat less reactive than 6-Me toward radical polymerization. This may reflect the higher degree of substitution and increased steric bulk of the alkenes in the former compared to the latter.

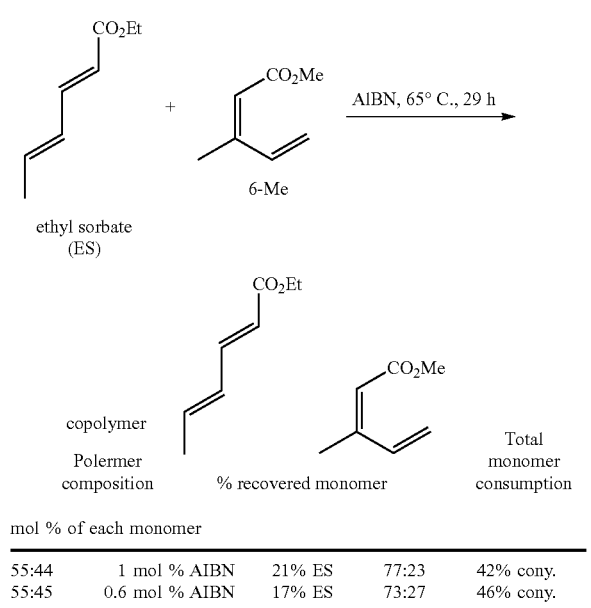

Scheme 4

| mol % of each monomer | | | | |
|---|---|---|---|---|
| 55:44 | 1 mol % AIBN | 21% ES | 77:23 | 42% conv. |
| 55:45 | 0.6 mol % AIBN | 17% ES | 73:27 | 46% conv. |

Other Polymerization Methods

To gain additional control over $M_n$ and lower the dispersities of the polymer products, especially when made via bulk polymerization (Dvornić, P. R.; Jaćović, M. S. Polym. Eng. Sci. 1981, 21, 792-796) several reversible deactivation radical polymerization strategies were explored (Jenkins, A. D.; Jones, R. G.; Moad, G. Pure Appl. Chem. 2009, 82, 483-491). Nitroxide mediated radical polymerization of 6-Me in the bulk initiated by TIPNO-St (TIPNO-St: N-(tert-butyl)-N-(2-methyl-1-phenylpropyl)-O-(1-phenylethyl)hydroxylamine: Benoit, D.; Chaplinski, V; Braslau, R.; Hawker, C. J. J. Am. Chem. Soc. 1999, 121, 3904-3920) behaved in a manner characteristic of a living polymerization; the Mn increased linearly with conversion (FIGS. 2A and 2B). This product showed a substantially lower dispersity ($Đ$ =1.45) than that of the polymer prepared from the AIBN bulk polymerization (Scheme 3).

Procedure for Nitroxide-Mediated Radical Polymerization (NMP) of (Z)-3-methylpenta-2,4-dienoate (6-Me)

To a 10 mL Schlenk flask was added N-(tert-butyl)-N-(2-methyl-1-phenylpropyl)-O-(1-phenylethyl)hydroxylamine (1 equiv, 25.7 mg, 0.079 mmol) and methyl (Z)-3-methylpenta-2,4-dienoate (6-Me) (100 equiv, 1 g, 7.93 mmol). The solution was degassed through three freeze-pump-thaw cycles and then heated at 110° C. Aliquots were taken at intervals to monitor conversion ($^1$H NMR) and Mn and dispersity ($Đ$) (SEC) (see FIGS. 2A and 2B)

Reversible Addition-Fragmentation Chain-Transfer (RAFT) Polymerization

Figure 3A:
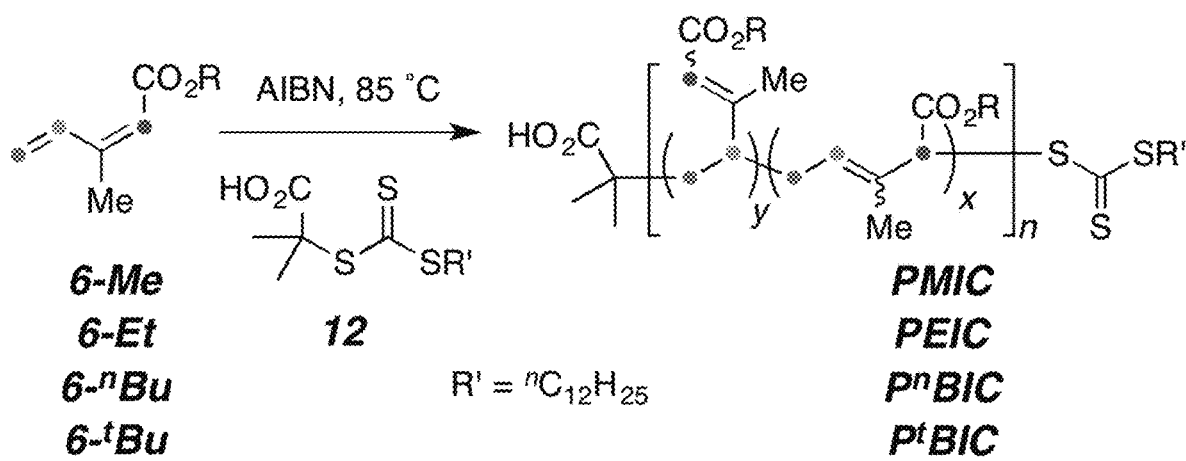

Reversible addition-fragmentation chain-transfer (RAFT) polymerization of the esters 6-R (FIG. 3A) was also investigated. When 6-Me (1 equiv) was polymerized in the presence of AIBN ($8\times10^{-5}$ equiv) and the trithiocarbonate 12 (DDMAT (2-{[(dodecylthio)carbonothioyl]thio}-2-methylpropanoic acid), $1\times10^{-3}$ equiv) as the RAFT agent, the resulting PMIC showed an $M_n$ of 150 kg·mol$^{-1}$ and a dispersity of 1.5 (SEC vs. PS) (FIGS. 3B and 3C). The $T_g$ of the sample was 34° C. and its entanglement molecular weight ($M_e=4\rho RT/5G_n°$) was 17 kg·mol$^{-1}$ (FIG. 4). The RAFT polymerization of 6-Me again appeared to be living (FIGS. 3B and 3C). As has been reported with, for example, methyl methacrylate, this RAFT polymerization also proceeded in the absence of a radical initiator (Stickler, M.; Meyerhoff, G. Makromol. Chem. 1978, 179, 2729-2745. Paulus, R. M.; Becer, C. R.; Hoogenboom, R.; Schubert, U. S. Aust. J. Chem. 2009, 62, 254-259). It is also worth noting that neither of these controlled polymerization methods altered the ratio of 1,4- vs. 1,2-addition modes of polymerization (i.e., the ratio remained ca. 1.5:1).

With the goal of establishing the effect of the ester alkyl moiety on $T_g$ and $M_e$, high molecular weight polymer samples were also prepared from the series of esters 6-Et, 6-$^n$Bu, and 6-$^t$Bu. Samples of each of PEIC, P$^n$BIC, and P$^t$BIC having $M_n$>100 kg·mol$^{-1}$ were prepared using AIBN and 12. The $T_g$s and $M_e$s of these poly(isoprenecarboxylates) are given in Table 1. The $T_g$s decrease as the ester alkyl moiety grows in size until the t-butyl analogue is reached, in which case there is a substantial increase in the $T_g$. This is quite analogous to the trend seen for simple poly(acrylate) esters (Table 1). Similarly, the $M_e$s for the poly(isoprenecarboxylates) parallel those for the analogous poly(acrylates). The former tend to be higher than the latter for most of the same ester alkyl groups, perhaps reflecting the contribution from the larger side chain moieties arising from the 1,2-mode of polymerization of the isoprenecarboxylate monomers 6.

TABLE 1

Glass transition temperature ($T_g$) and $M_e$ of poly(isoprenecarboxylates) vs. poly(acrylates) (a) Comparison of glass transition temperatures ($T_g$) and entanglement molecular weights ($M_e$) for the four PICA esters; all five samples had $M_n > 100$ kg·mol$^{-1}$. (b) $T_g$ and $M_e$ for poly(methyl acrylate) (PMA), poly(ethyl acrylate) (PEA), poly(n-butyl acrylate) (P$^n$BA), and poly(t-butyl acrylate) (P$^t$BA)

| a Poly(isoprenecarboxylates) | | | | |
|---|---|---|---|---|
| | PMIC | PEIC | P$^n$BIC | P$^t$BIC |
| $T_g$ (°C) | 34 | 10 | −19 | 55 |
| $M_e$ (kg/mol) | 17 | 22 | 41 | 39 |
| b Poly(acrylates) | | | | |
| | PMA | PEA | P$^n$BA | P$^t$BA |
| $T_g$ (°C) | 22[a] | −8[a] | −43[a] | 55[a] |
| $M_e$ (kg/mol) | 9[b] | 12[c] | 29[d] | NA |

[a]Penzel, E. Polyacrylates. In Ullmann's Encyclopedia of Industrial Chemistry; Wiley-VCH Verlag GmbH & Co. KGaA: Weinheim, Germany, 2000; Vol. 28, pp 515-536.
[b]Fetters, L. J.; Lohse, D. J.; Richter, D.; Witten, T. A.; Zirkelt, A. Macromolecules 1994, 27, 4639-4647.
[c]Andreozzi, L.; Castelvetro, V; Faetti, M.; Giordano, M.; Zulli, F. Macromolecules 2006, 39, 1880-1889.
[d]Yamazaki, H.; Takeda, M.; Kohno, Y; Ando, H.; Urayama, K; Takigawa, T. Macromolecules 2011, 44, 8829-8834).

Procedures for RAFT Polymerization

Poly(methyl isoprenecarboxylate) (PMIC)

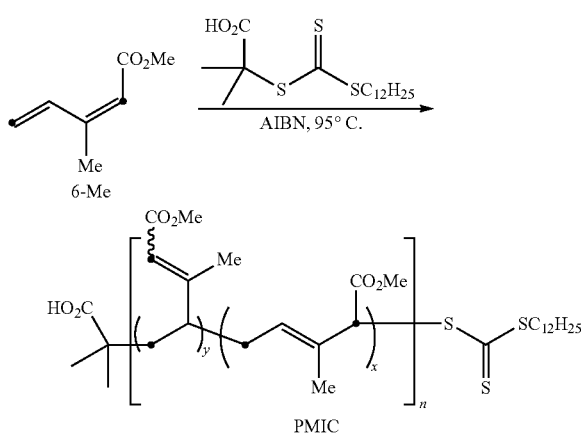

AIBN (0.08 equiv, 0.16 mg, 1.0 μmol) was added as a stock solution in DCM (10 mg·mL$^{-1}$) to a 10 mL Schlenk flask. The DCM was removed under reduced pressure and 2-{[(dodecylthio)carbonothioyl]thio}-2-methylpropanoic acid (DDMAT, 12, 1.0 equiv, 4.3 mg, 12 μmol) and methyl (Z)-3-methylpenta-2,4-dienoate (6-Me, 1000 equiv, 1.50 g, 11.9 mmol) were added. The headspace was degassed through several freeze-pump-thaw cycles, under static vacuum, until bubbling no longer was observed during thawing. Nitrogen was then admitted and the flask was heated in an oil bath held at 95° C. Aliquots were periodically withdrawn under nitrogen flow. $^1$H NMR analysis of each crude aliquot relied, principally, on integration of the following resonances: 7.81-H4 in the starting 6-Me; 6.40-H4 in a small amount of the E-isomer of 6-Me (E-6-Me) that appears during the polymerization; and 4.9-6.0, the superposition of the single alkene proton arising from both the 1,4- and 1,2-modes of addition in the PMIC polymer as well as protons H2, HS$_E$, and H5$_Z$ in both 6-Me and E-6-Me. $^1$H NMR analysis of the crude aliquots indicated >94% conversion of the monomer after 5 days. The flask was allowed to cool to ambient temperature, the residue was dissolved in dichloromethane, and the polymer was precipitated by addition to swirled methanol held at 0° C. The resulting slurry was cooled (−20° C.), centrifuged, decanted, and rendered free of solvent under vacuum overnight at 70° C. to provide 1.26 g of PMIC (84% yield). This product was judged to arise from a 42:58 ratio of 1,2- and 1,4-modes of polymerization (cf. "y" vs. "x", respectively, in the structure of PMIC) across the conjugated diene based on integration of $^1$H NMR resonances from 5.83-5.37 ppm (from moieties arising from 1,2-addition) and 5.37-4.92 ppm (from moieties arising from 1,4-addition). A nearly identical ratio for the 1,2- and 1,4-modes was seen in the relative intensities of the $^{13}$C NMR resonances for the conjugated (167.0-165.5 ppm) vs. unconjugated (174.2-173.0 ppm) carbonyl carbons.

$^1$H NMR (500 MHz, CDCl$_3$): δ 5.84-4.97 (m, 1.0H, HC=), 3.84-3.50 (m, 3.1H, OCH$_3$), 3.08-1.16 (m, 6.2H, three C$_{sp3}$H protons on the backbone and allylic methyl groups).

$^{13}$C NMR (125 MHz, CDCl$_3$): δ 174.1-173.1, 166.9-165.5, 161.9-159.0, 135.0-132.0, 126.6-124.6, 120.0-116.5, 54.4-53.8, 51.3-52.3, 50.9-50.5, 48-43, 38-27.5, 20.0-18.5, and 15.5-12.8.

IR (neat, selected peaks): 2950, 1728, 1715, 1643, and 1433 cm$^{-1}$.

Figure 5:
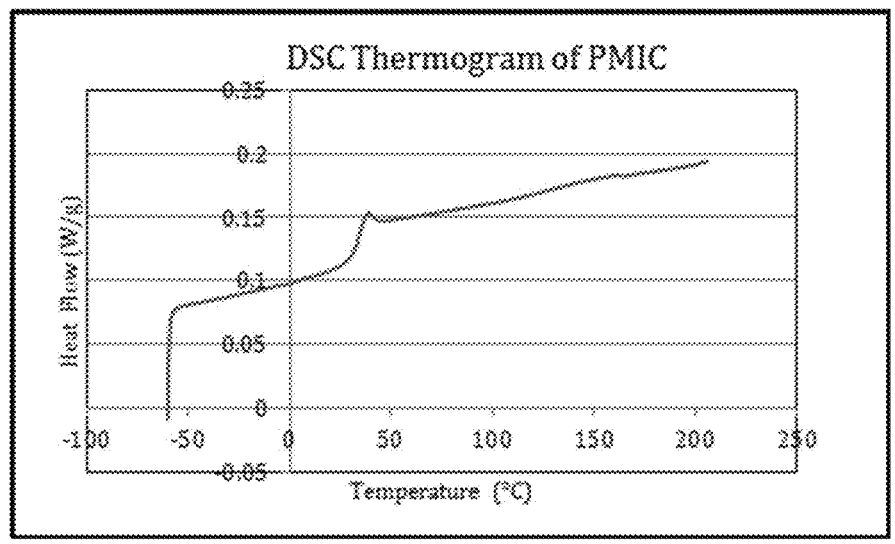
FIG. 5 shows a DSC thermogram of PMIC (methyl ester, $M_n$=152,000 g mol$^{-1}$). Glass transition temperature observed at 34° C.

DSC $T_g$=34° C. (FIG. 5)

Figure 6:
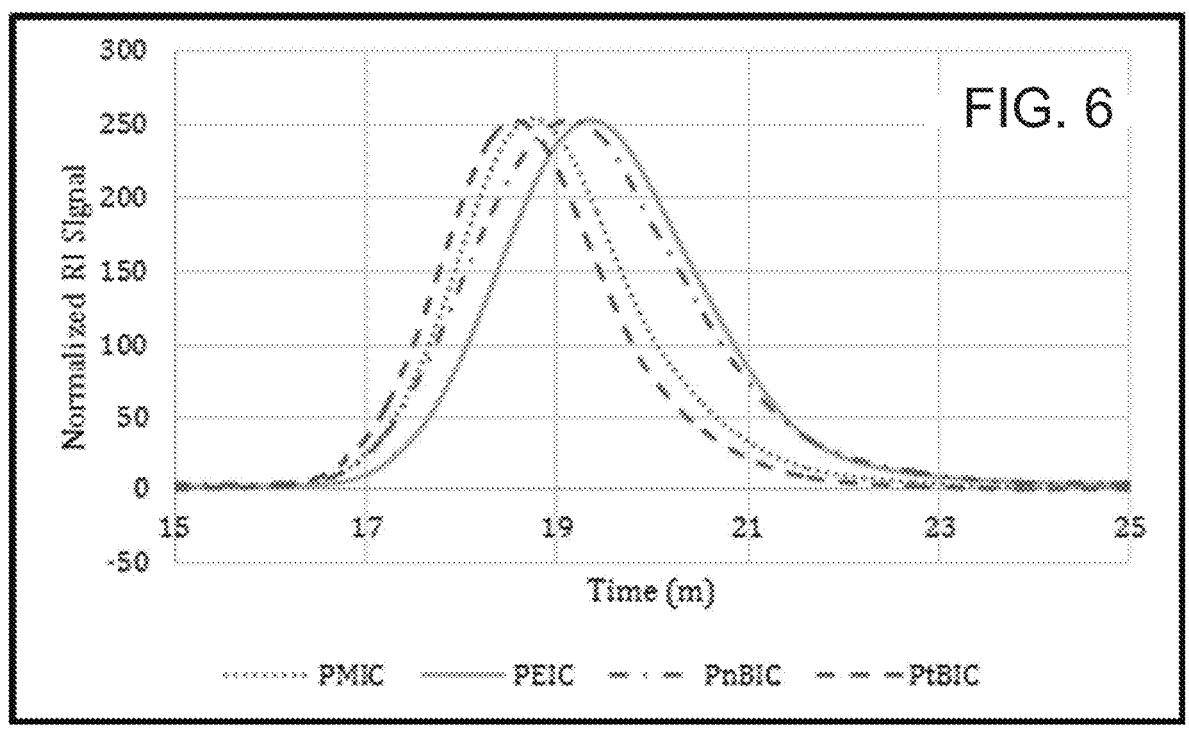
FIG. 6 shows an overlay of the SEC chromatograms of the poly(isoprenecarboxylic acid esters) (PS calibration in CHCl$_3$). Molecular weights ($M_n$) of PMIC, poly(ethyl isoprenecarboxylate) (PEIC), poly(n-butyl isoprenecarboxylic acid) (P"BIC), poly(t-butyl ester isoprenecarboxylate) (P$^t$-BIC) correspond to 152, 101, 115, 170 kg mol$^{-1}$, respectively.

SEC PS-GPC (CHCl$_3$): $M_n$=152,000 g mol$^{-1}$, $M_w$=228,000 g mol$^{-1}$, $Đ$=1.5 (FIG. 6)

Figure 7:
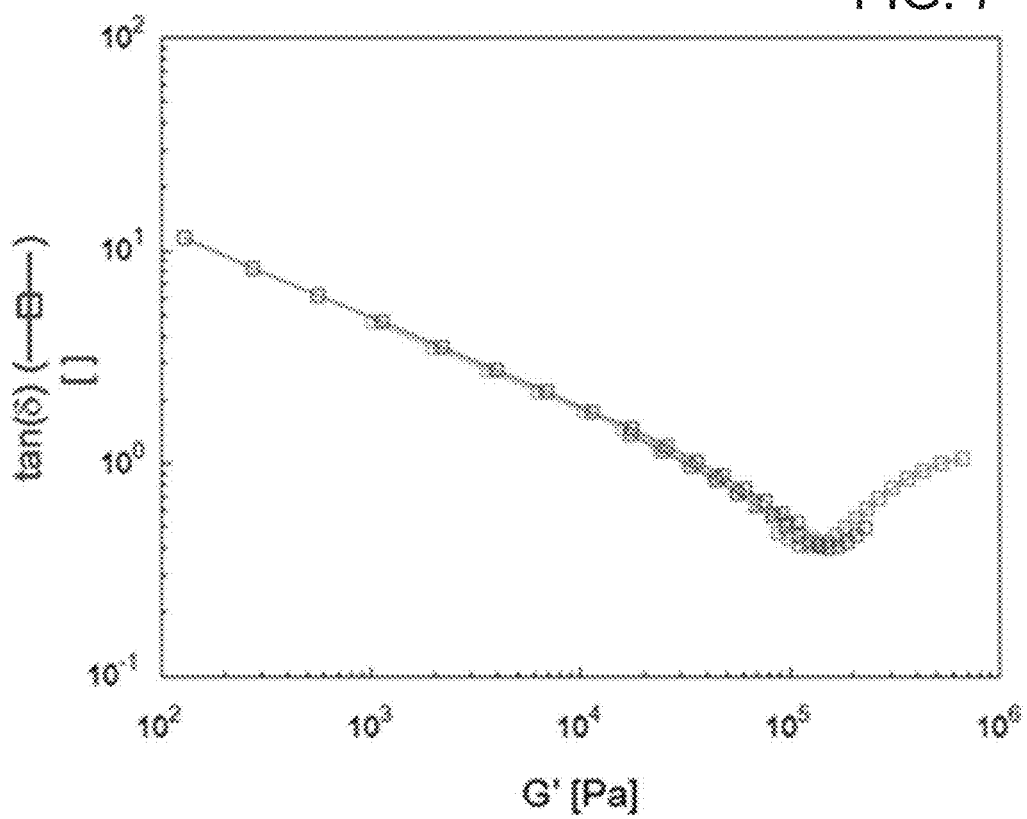
FIG. 7 shows Tan Delta vs Elastic Modulus for PMIC. The Plateau modulus was approximated at the minimum of Tan Delta corresponding to 1.11*10$^5$ Pa. $M_e$=17,000 g mol$^{-1}$.

Linear Viscoelastic Measurements: $T_{ref}$=110° C., $G_N$=1.53*10$^5$ Pa, $M_e$=17.0 kDa (FIGS. 4 and 7)

Figure 8:
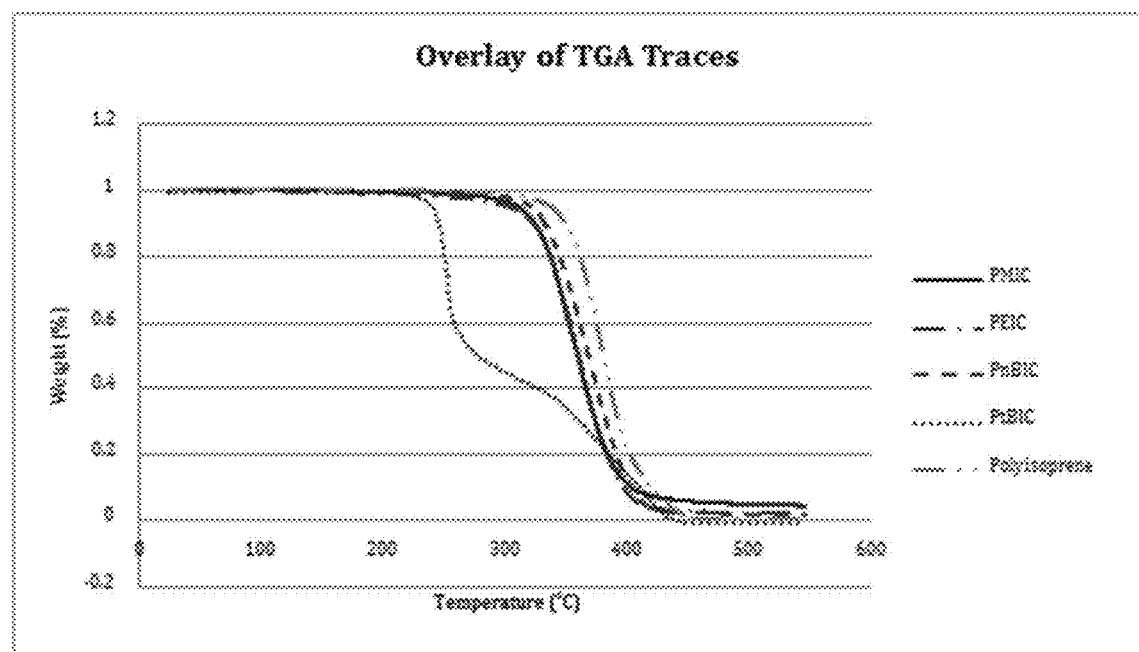
FIG. 8 shows an overlay of the TGA traces of the poly(isoprenecarboxylic acid esters) PMIC, PEIC, P"BIC, and P$^t$BIC as well as polyisoprene (PI). The sample size for each was between 10-20 mg. P$^t$BIC shows two modes of degradation, the first indicative of the thermal loss of isobutylene.

The thermal degradation of the polymer shown in FIG. 8.

Poly(ethyl isoprenecarboxylate) (PEIC)

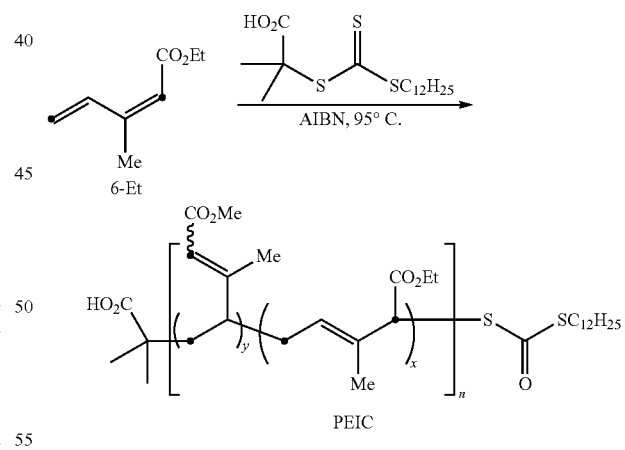

AIBN (0.08 equiv, 0.14 mg, 0.9 μmol) was added as a stock solution in DCM (10 mg·mL$^{-1}$) to a 10 mL Schlenk flask. The DCM was removed under reduced pressure and 2-{[(dodecylthio)carbonothioyl]thio}-2-methylpropanoic acid (DDMAT, 12, 1.0 equiv, 3.9 mg, 10.7 μmol) and ethyl (Z)-3-methylpenta-2,4-dienoate (6-Et, 1000 equiv, 1.50 g, 10.7 mmol) were added. The headspace was degassed through several freeze-pump-thaw cycles, under static vacuum, until bubbling no longer was observed during thawing. Nitrogen was then admitted and the flask was heated in an oil bath held at 95° C. Aliquots were periodically withdrawn under nitrogen flow. As with the examples above, $^1$H NMR analysis of the crude aliquots indicated >98% conversion of the monomer after 4 days. The flask was allowed to cool to ambient temperature, the residue was dissolved in dichloromethane, and the polymer was precipitated by addition to swirled methanol held at 0° C. The resulting slurry was cooled in (−20° C.), centrifuged, decanted, and rendered free of solvent under vacuum overnight at 70° C. to provide 1.18 g of PEIC (79% yield).

This product was also judged to arise from a 42:58 ratio of 1,2- and 1,4-modes of polymerization (cf. "y" vs. "x", respectively) across the conjugated diene based on integration of $^1$H NMR resonances from 5.85-5.38 ppm (from moieties arising from 1,2-addition) and 5.38-4.97 ppm (from moieties arising from 1,4-addition). A nearly identical ratio for the 1,2- and 1,4-modes was seen in the relative intensities of the $^{13}$C NMR resonances for the conjugated (166.8-165.0 ppm) vs. unconjugated (173.0-172.5 ppm) carbonyl carbons.

$^1$H NMR (500 MHz, CDCl$_3$): δ 5.8-5.0 (m, 1.0H), 4.3-3.7 (m, 2.2H, OCH$_2$CH$_3$), 3.5-1.2 (m, 9.2H, three C$_{sp3}$H protons on the backbone, allylic methyl groups, and CH$_2$CH$_3$)).

$^{13}$C NMR (125 MHz, CDCl$_3$): δ 173.6-172.5, 166.5-165.0, 162.0-159.0, 135.0-132.0, 126.5-124.5, 120.3-116.5, 60.5-60.0, 59.6-59.0, 54.5-53.9, 52.5-51.6, 48-43, 38-27.5, 20.0-18.5, and 14.5-13.0.

IR (neat, selected peaks): 2979, 1726, 1713, and 1641 cm$^{-1}$.

Figure 9:
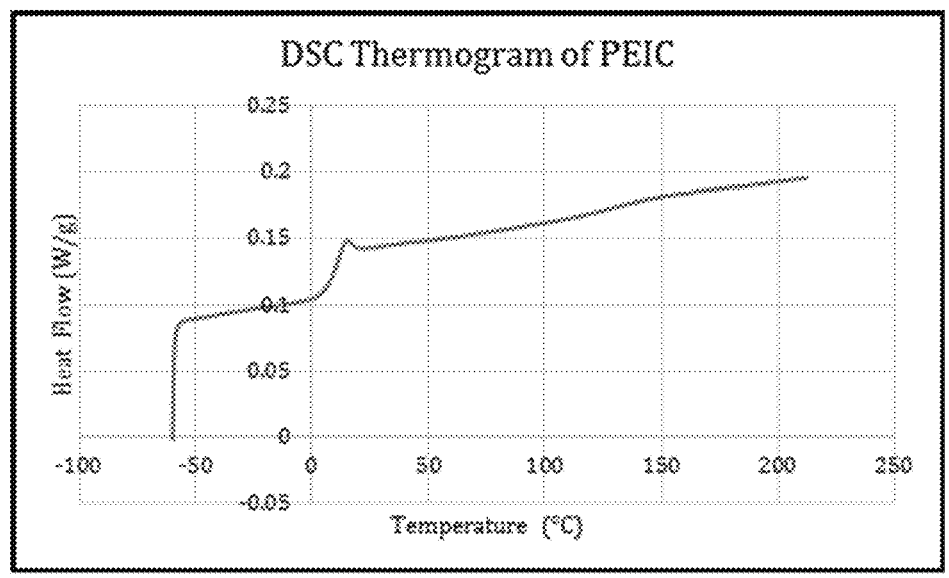
FIG. 9 shows a DSC thermogram of PEIC (ethyl ester, $M_n$=101,000 g mol$^{-1}$). Glass transition temperature observed at 16° C.

DSC T$_g$=10° C. (FIG. 9)

SEC PS-GPC (CHCl$_3$): M$_n$=101,000 g mol$^{-1}$, M$_w$=157,000 g mol$^{-1}$, Đ=1.6 (FIG. 6)

Figure 10:
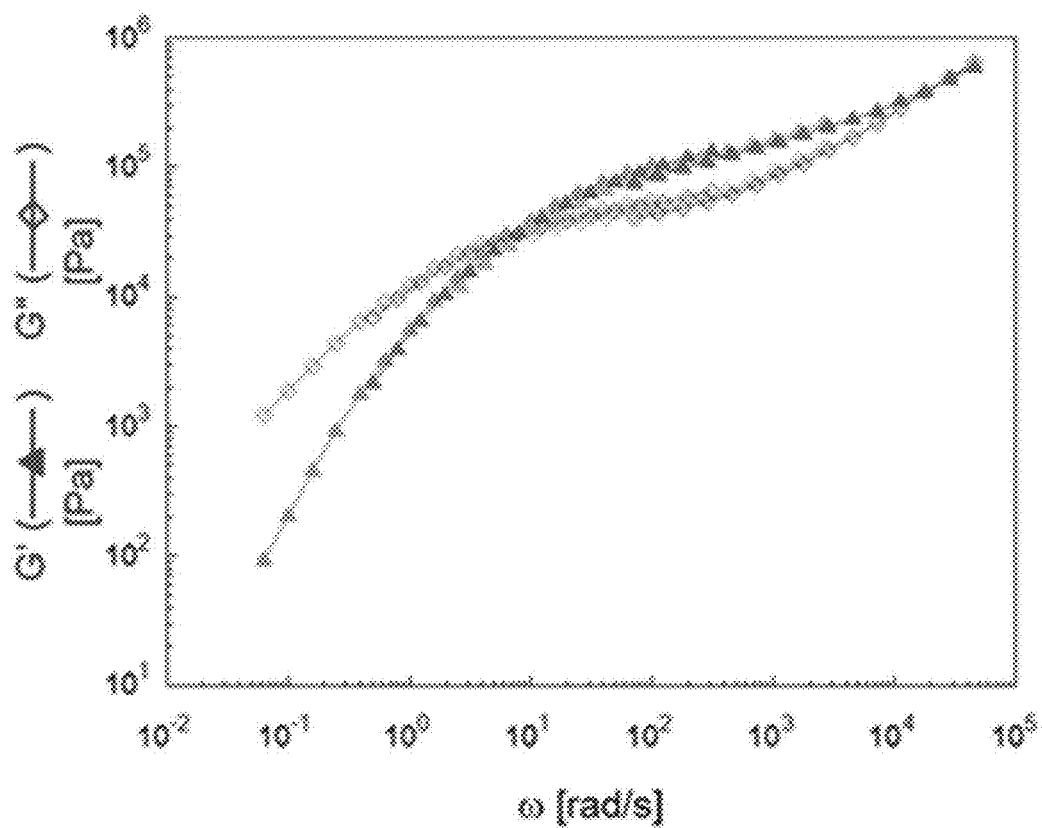
FIG. 10 shows Time-Temperature Superposition plot of PEIC (Mn=101,000 g/mol) referenced at 85° C. (Tg=16° C.). Each of the two curves comprised of closed triangles and open squares is a composite of four separate curves measured, respectively, at 45, 50, 75, and 85° C.
Figure 11:
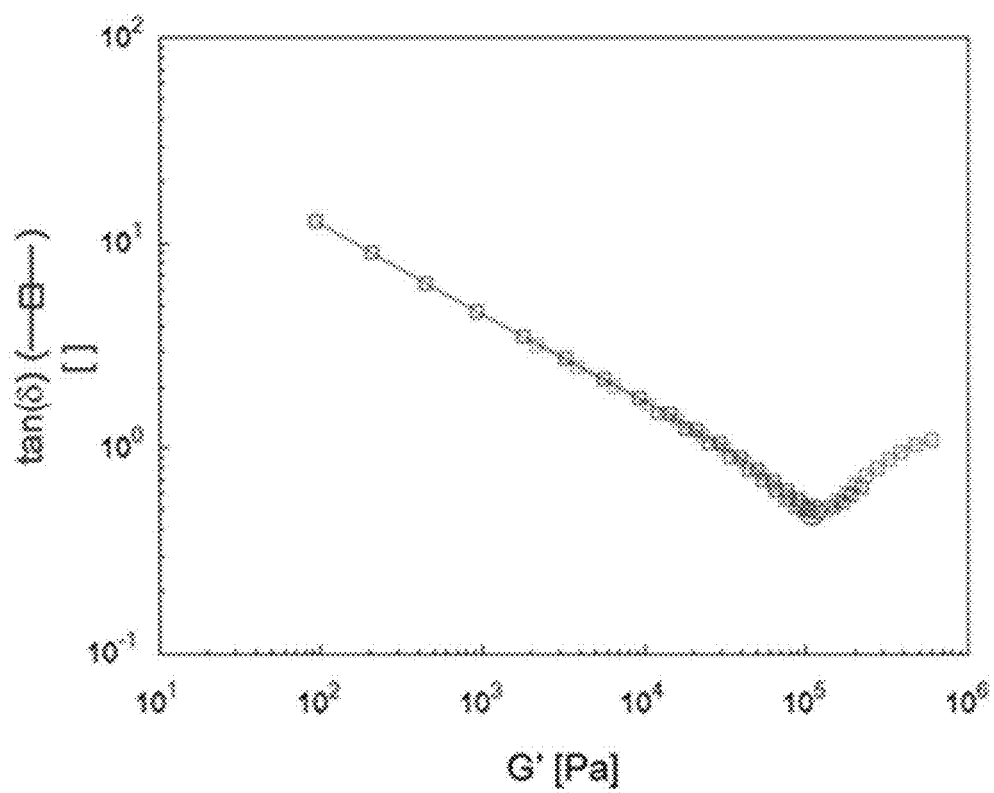
FIG. 11 shows tan delta vs elastic modulus for PEIC. The Plateau modulus approximated at the minimum of Tan Delta corresponding to 1.11*10$^5$ Pa. $M_e$=21,100 g mol$^{-1}$.

Linear Viscoelasticity Measurements: T$_{ref}$=85° C., G$_N$=1.11*10$^5$ Pa, M$_e$=21.5 kDa (FIGS. 10 and 11)

The thermal degradation of the polymer shown in FIG. 8.

Poly(n-butyl isoprenecarboxylic acid) (P$^n$BIC)

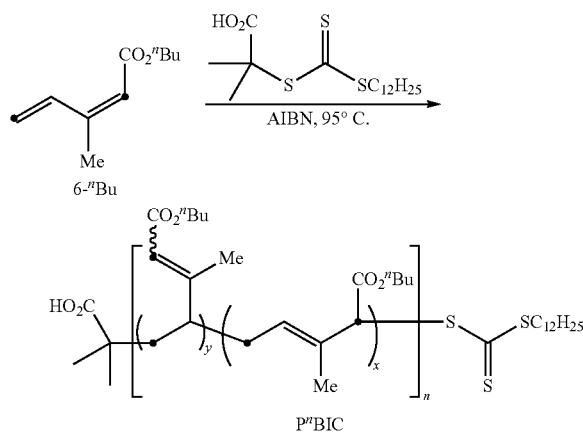

AIBN (0.08 equiv, 0.14 mg, 0.7 µmol) was added as a stock solution in DCM (10 mg·mL$^{-1}$) to a 10 mL Schlenk flask. The DCM was removed under reduced pressure and 2-{[(dodecylthio)carbonothioyl]thio}-2-methylpropanoic acid (DDMAT, 12, 1.0 equiv, 10.8 mg, 29.6 µmol) and tert-butyl (Z)-3-methylpenta-2,4-dienoate (6-$^n$Bu, 300 equiv, 1.50 g, 8.93 mmol) were added. The headspace was degassed through several freeze-pump-thaw cycles, under static vacuum, until bubbling no longer was observed during thawing. Nitrogen was then admitted and the flask, which was heated in an oil bath held at 115° C. Aliquots were periodically withdrawn under nitrogen flow. As with the examples above, $^1$H NMR analysis of the crude aliquots indicated >90% conversion of the monomer after 7 days, and the M$_n$, M$_w$, and Đ were analyzed (M$_n$=69,000 g mol$^{-1}$, M$_w$=90,000 g mol$^{-1}$, Đ=1.3). To demonstrate the livingness of this polymerization, more 6-$^n$Bu (320 eq, 1.6 g, 9.5 mmol) was added and the same freeze-pump-thaw cycles were performed. After introduction of nitrogen into the headspace, the Schlenk flask was placed into an oil bath at 95° C. $^1$HNMR analysis of the crude aliquots indicated >90% conversion of the monomer after 6 days. The flask was allowed to cool to ambient temperature and the residue was dissolved in dichloromethane and the polymer was precipitated by addition to swirled methanol held at 0° C. The resulting slurry was cooled (−20° C.), centrifuged, decanted, and rendered free of solvent under vacuum overnight at 70° C. to provide 1.96 g of P$^n$BIC (63% yield). This sample was judged to be a 41:59 mixture of 1,2:1,4 addition products based on integration of $^1$H NMR peaks from 5.90-5.40 ppm (1,2 addition) and 5.40-4.95 ppm (1,4 addition). A nearly identical ratio was seen for the 1,2- and 1,4-modes in the relative intensities of the $^{13}$C NMR resonances for the conjugated (166.8-165.1 ppm) vs. unconjugated (173.7-172.5 ppm) carbonyl carbons.

$^1$H NMR (500 MHz, CDCl$_3$): δ 5.8-5.0 (m, 1.0H), 4.1-3.9 (m, 2.1H, OCH$_2$CH$_2$), 3.6-1.2 (m, 10.5H, three C$_{sp3}$H protons on the backbone, the allylic methyl groups, and OCH$_2$CH$_2$CH$_3$), and 0.97-0.87 (br t, J=7 Hz, 3.0H, CH$_2$CH$_2$CH$_3$).

$^{13}$C NMR (125 MHz, CDCl$_3$): δ 173.8-172.6, 166.6-165.2, 161.8-159.3, 135.0-132.3, 127.0-124.4, 120.0-116.7, 64.4-63.9, 63.6-63.0, 54.8-54.0, 52.6-51.6, 48.1-43.9, 38-27.0, 19.8-18.6, and 14.5-13.0.

IR (neat, selected peaks): 2979, 1726, 1713, and 1641 cm$^{-1}$.

Figure 12:
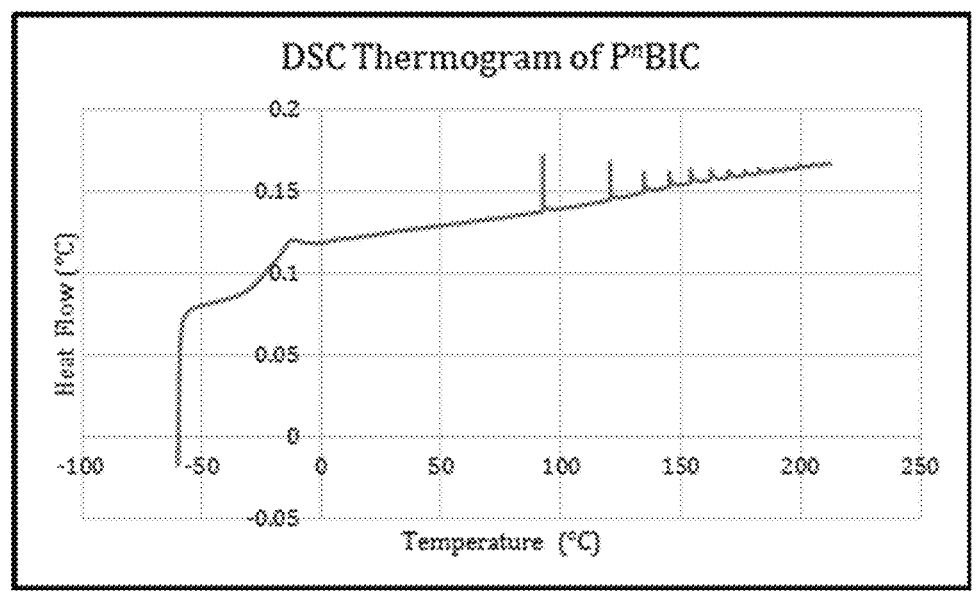
FIG. 12 shows a DSC thermogram of P"BIC (n-butyl ester, $M_n$=115,000 g mol$^{-1}$). Glass transition temperature observed at –19° C.

DSC T$_g$=−19° C. (FIG. 12)

SEC PS-GPC (CHCl$_3$): M$_n$=115,000 g mol$^{-1}$, M$_w$=188,000 g mol$^{-1}$, Đ=1.6 (FIG. 6)

Figure 13:
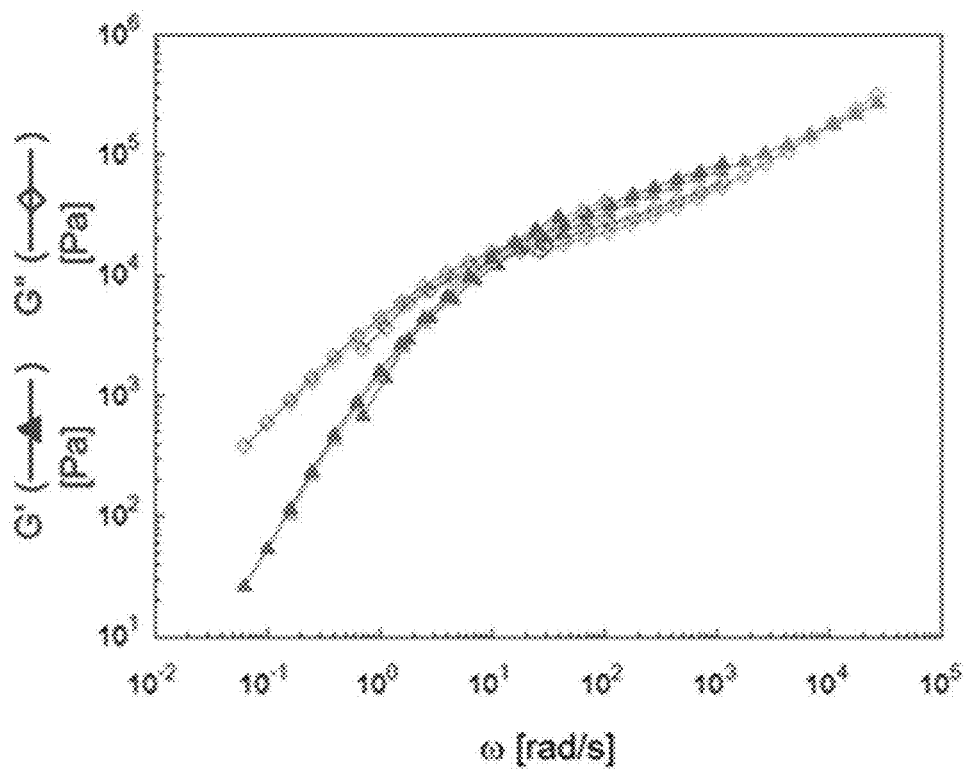
FIG. 13 shows Time-Temperature Superposition plot of P"BIC ($M_n$=115,000 g/mol) referenced at 50° C. ($T_g$=–16° C.). Each of the two curves comprised of closed triangles and open squares is a composite of four separate curves measured, respectively, at 10, 30, 50, and 60° C.
Figure 14:
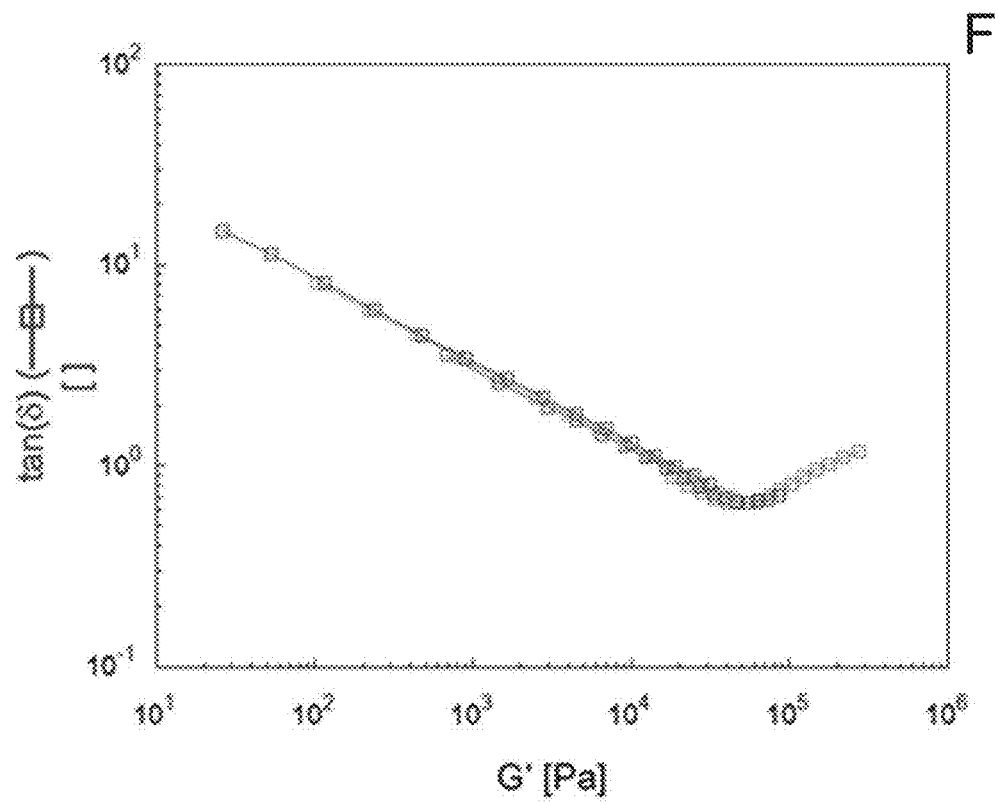
FIG. 14 shows tan delta vs elastic modulus for P"BIC. The Plateau Modulus the minimum of Tan Delta corresponding to approximated at 5.56*10$^5$ Pa. $M_e$=40,900 g mol$^{-1}$.

Linear Viscoelasticity Measurements: T$_{ref}$=50° C., G$_N$=5.56*10$^5$ Pa, M$_e$=40,900 kDa. (FIGS. 13 and 14)

The thermal degradation of the polymer shown in FIG. 8.

Poly(t-butyl ester isoprenecarboxylate) (P$^t$BIC)

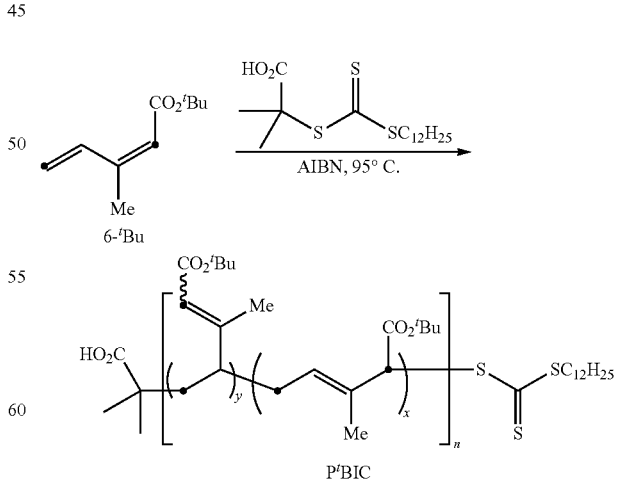

AIBN (0.08 equiv, 0.12 mg, 0.7 µmol) was added as a stock solution in DCM (10 mg·mL$^{-1}$) to a 2 mL Schlenk flask. The DCM was removed under reduced pressure and DDMAT (12, 1.0 equiv, 3.2 mg, 8.9 μmol) and tert-butyl (Z)-3-methylpenta-2,4-dienoate (6-$^t$Bu, 1000 equiv, 1.50 g, 8.93 mmol) were added. The headspace was degassed through several freeze-pump-thaw cycles, under static vacuum, until bubbling no longer was observed during thawing. Nitrogen was then admitted and the flask, which was heated in an oil bath held at 115° C. Aliquots were periodically withdrawn under nitrogen flow. As with the examples above, $^1$H NMR analysis of the crude aliquots indicated >90% conversion of the monomer after 4 days. The flask was allowed to cool to ambient temperature, the residue was dissolved in dichloromethane, and the polymer was precipitated by addition to swirled methanol held at 0° C. The resulting slurry was cooled (−20° C.), centrifuged, decanted, and rendered free of solvent under vacuum overnight at 70° C. to provide 1.22 g of P$^t$BIC (81% yield).

This sample was judged to be a 40:60 mixture of 1,2:1, 4-addition products based on integration of $^1$H NMR peaks from 5.79-5.37 ppm (1,2 addition) and 5.37-4.94 ppm (1,4 addition). A nearly identical ratio was seen for the 1,2- and 1,4-modes in the relative intensities of the $^{13}$C NMR resonances for the conjugated (166.6-164.8 ppm) vs. unconjugated (173.4-172.0 ppm) carbonyl carbons.

$^1$H NMR (500 MHz, CDCl$_3$): δ 5.8-5.0 (m, 1.0H), 4.1-1.8 (m, 3.2H, all C$_{sp3}$H protons on the backbone), 1.8-1.5 (m, 2.6H, the allylic methyl groups), and 1.5-1.3 (m, 9.2H, O[CH$_3$]$_3$).

$^{13}$C NMR (125 MHz, CDCl$_3$): δ 172.9-172.1, 166.2-164.9, 160.2-158.4, 135.4-132.9, 127.5-124.4, 121.6-118.0, 80.6-78.7, 55.8-55.1, 52.4-53.6, 48.1-47.1, 45.8-44.6, 38.4-31.5, 29.6-27.6, 20.0-19.0, and 15.1-12.9.

IR (neat, selected peaks): 2976, 1722, 1710, 1641, and 1454 cm$^{-1}$.

Figure 15:
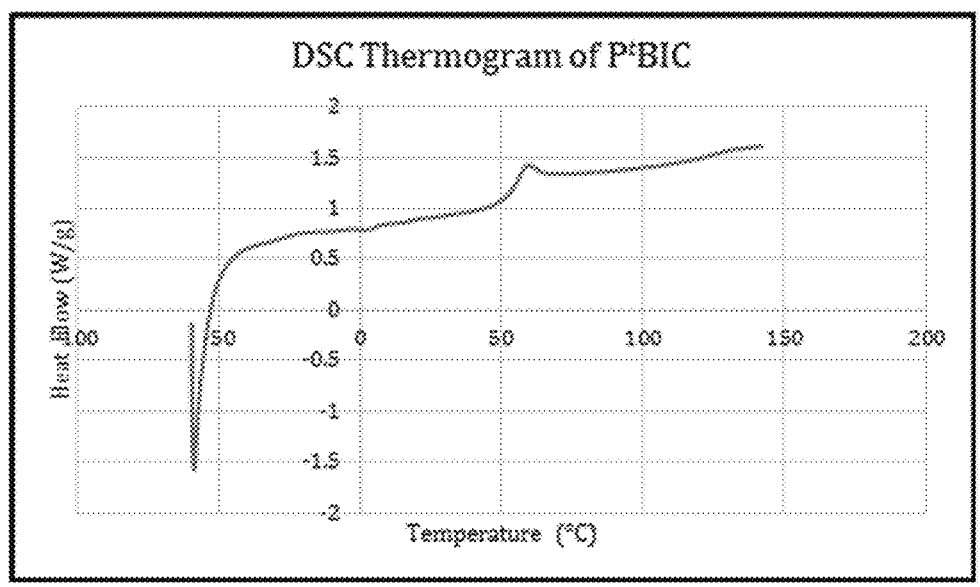
FIG. 15 shows a DSC thermogram of P$^t$BIC (t-butyl ester, $M_n$=170,000 g mol$^{-1}$). Glass transition temperature observed at 55° C.

DSC T$_g$=55° C. (FIG. 15)

SEC PS-GPC (CHCl$_3$): M$_n$=170,000 g mol$^{-1}$, M$_w$=260,000 g mol$^{-1}$, Đ=1.5 (FIG. 6)

Figure 16:
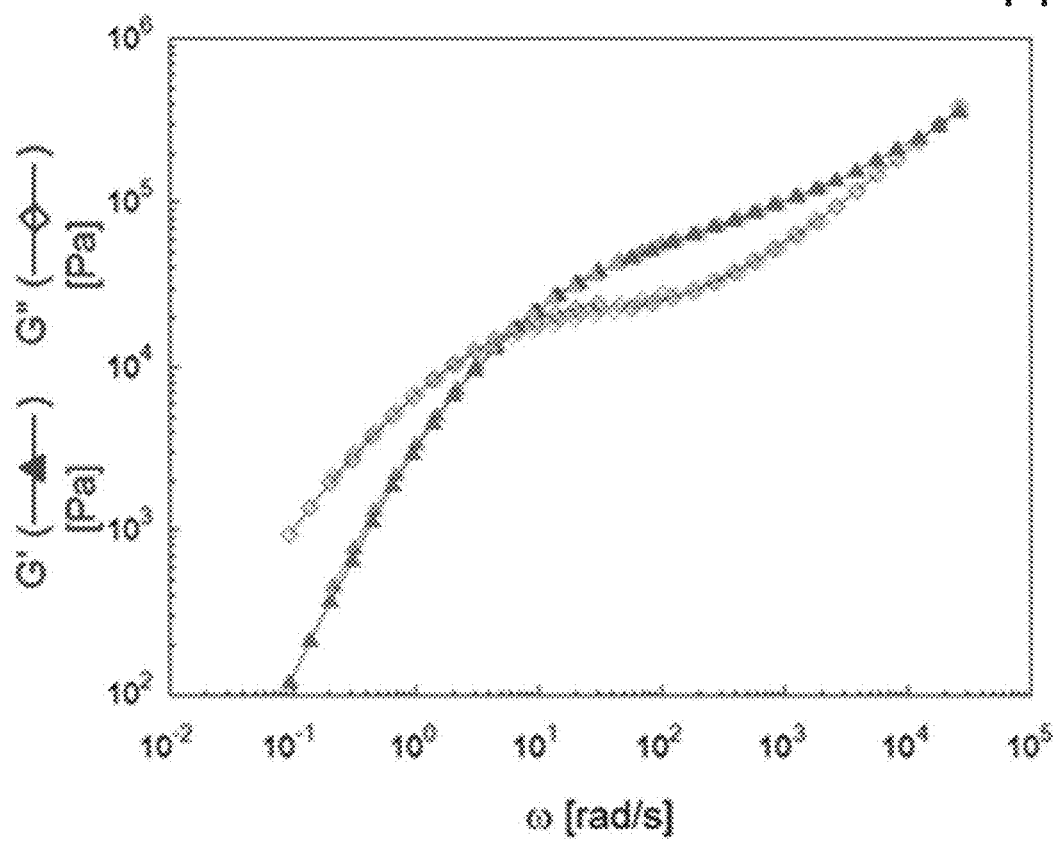
FIG. 16 shows Time-Temperature Superposition plot of P$^t$BIC ($M_n$=180,000 g/mol) referenced at 125° C. ($T_g$=55° C.). Each of the two curves comprised of closed triangles and open squares is a composite of four separate curves measured, respectively, at 85, 100, 125, and 140° C.
Figure 17:
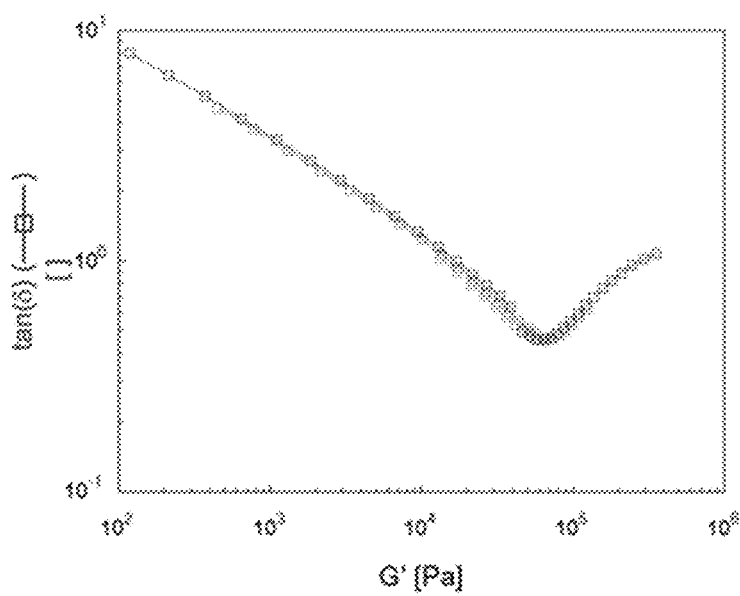
FIG. 17 shows Tan Delta vs Elastic Modulus for P$^t$BIC. The Plateau Modulus approximated at the minimum of Tan Delta corresponding to 6.59*10$^4$ Pa. $M_e$=38,700 g mol$^{-1}$.

Linear Viscoelasticity Measurements: T$_{ref}$=125° C., G$_N$=6.59*10$^5$ Pa, M$_e$=38.7 kDa (FIGS. 16 and 17)

Characterization of the Polymers

The SEC chromatograms of the poly(isoprenecarboxylic acid esters) (PS calibration in CHCl$_3$) can be seen in FIG. 6. Molecular weights (M$_n$) of PMIC, PEIC, PUBIC, PUBIC correspond to 152, 101, 115, 170 kg mol$^{-1}$, respectively.

Preparation of Poly(isoprenecarboxylic acid)

Isoprenecarboxylic acid (6-H, 1.00 eq, 224 mg, 2.00 mmol), 2,2'-azobis(2-methylpropionitrile) (0.01 eq, 3.3 mg, 0.020 mmol), and DMF (220 μL) were added to a 1-dram vial fitted with a Teflon cap. The vial was subjected to three freeze-pump-thaw cycles and the headspace was filled with nitrogen gas. The solution was allowed to react for 17 hours at 65° C., and an aliquot was analyzed via NMR spectroscopy (ca. 97% conversion to polymer). The polymer was then precipitated into a solution of MeOH and water (3:1), centrifuged, and decanted to give a white solid. The solid was resuspended into MeOH, precipitated into DCM, centrifuged, decanted, and placed on hi vacuum at 110° C. for 24 hours to give poly(isoprenecarboxylic acid) (166 mg, 74.1% yield) as a white solid.

Preparation of Poly(isoprenecarboxamides)

RAFT polymerization of each of the prepared isoprenecarboxamides was carried out in the same manner as described earlier for the isoprenecarboxylic esters to produce the poly(isoprenecarboxamides).

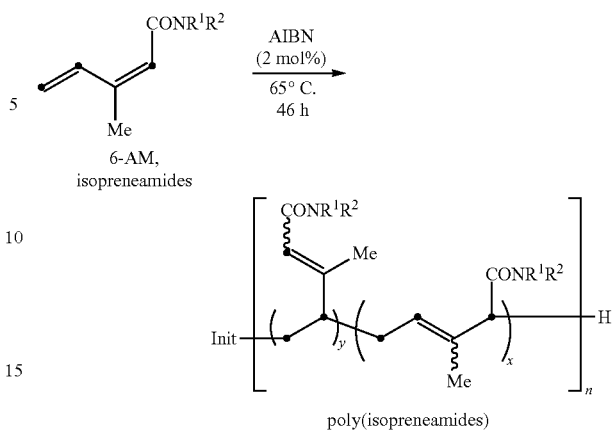

6-AM, isopreneamides poly(isopreneamides)

Preparation of Hydrogels and Poly(isoprenecarboxamides)

Figure 18:
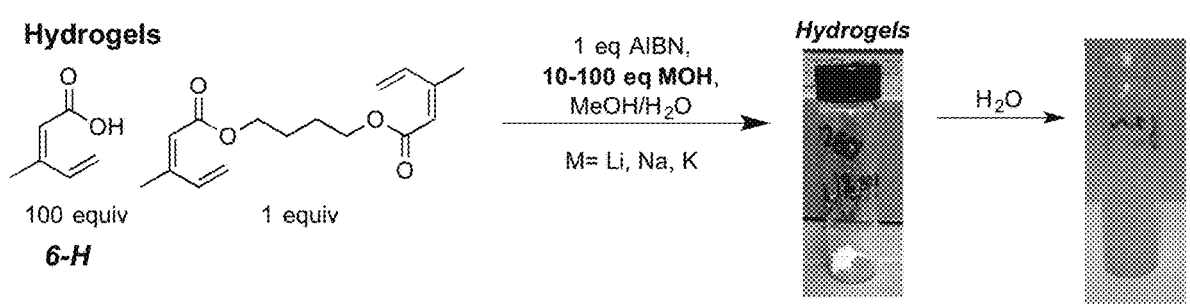
FIG. 18 shows an illustrative example of a hydrogel [poly(isoprenecarboxylic acid)] synthesis and a hydrogel formed thereby.

Hydrogels can be prepared according to the reaction seen in FIG. 18. Specifically, cross-linked versions of [poly (isoprenecarboxylic acid)] were synthesized by AIBN initiated polymerization of 6-H in the presence of the bis-ester derived via 6-H and 1,4-butanediol. The starting acid was pretreated with varying amounts of sodium hydroxide (from 0.1 to 0.9 equiv of the carboxylic acid 6-H) and this mixture polymerized directly to provide polymers as a pale yellow, clear gel. This was suspended in water to remove non-crosslinked polymers. Acetone was added several times to leach away the water by decantation. The residue was dried at 70° C. under vacuum for a day and ground to a fine white powder. This material was shown to have hydrogel properties—the ability to absorb large (on a wt:wt basis) amounts of water. The powdered samples could be swelled to hold about 205-335 times their mass of water. Analogous lithium or potassium salts were also prepared and shown to behave as hydrogels as well.

Alternatively, hydrogels can be prepared by crosslinking using a bis-methacrylate, which is less expensive, albeit not as environmentally advantageous, than an alternative, bis-isoprenecarboxylate-containing crosslinking agent.

Synthesis of Crosslinked Poly(isoprenecarboxylic acid-co-sodioisoprenecarboxylate)

2,2'-Azobis(2-methylpropionitrile) (AIBN, 0.01 equiv, 6.4 mg, 0.04 mmol), (Z)-3-methylpenta-2,4-dienoic acid (1.0 equiv, 448 mg, 4.00 mmol), and MeOH (400 μL) were added to a 1-dram vial. Sodium hydroxide was added via a 7.9 M solution (0.9 equiv, 455 μL, 3.60 mmol) followed by additional water (155 μL) to neutralize 90% of the carboxylic acid groups to sodium carboxylates. The crosslinking agent, butane-1,4-diyl (2Z,2'Z)-bis(3-methylpenta-2,4-dienoate) (0.01 equiv, 11.2 mg, 0.04 mmol) was added in MeOH (200 μL). The headspace was evacuated via freeze-pump-thaw cycles until bubbling no longer persisted upon thawing. Nitrogen gas was admitted, and the vial was sealed with a Teflon-fitted cap. The vial was placed into a sand bath held at 65° C. for 24 hours. The newly formed gel was then transferred to a 6-dram vial and soluble impurities were removed through first introducing water (ca. 8 mL) to slightly-swell the polymer. This material was washed repeatedly with acetone, during which the polymer contracted in volume significantly as the water was leached from the sample. This material was then placed under hi-vacuum for 48 hours at 70° C. and ground to a fine white powder using a mortar and pestle.

Hydrogel Preparation

Figure 38:
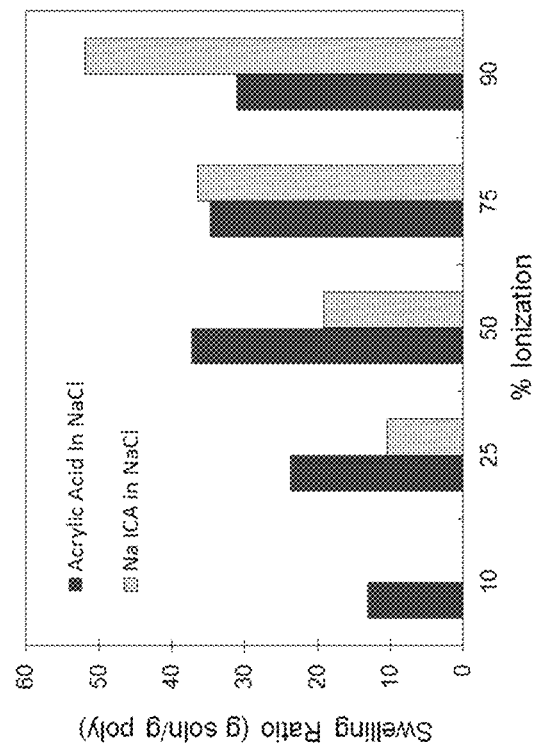
FIG. 38 shows masses of water retained by hydrogels based on polymers of varying proportions of acid:carboxylate, after being immersed in either pure water or various salt solutions.

A portion (25-50 mg) of the above crosslinked powder was allowed to swell in water for 24 h and excess water was pipetted off and additionally removed by gently wiping with a moist paper towel. FIG. 18 shows a photograph of the hydrogel after swelling. The masses of water retained by hydrogels based on polymers of varying proportions of acid:carboxylate, after being immersed in either pure water or various salt solutions, are shown in Tables 2a-c and FIG. 38 Additionally, these sodiated hydrogels swell more in the presence of water at higher ionizations (NaOH equivalents) than do acrylic acid-based hydrogels synthesized under identical conditions, presumably due to the increased distance between carboxylates (FIG. 38).

TABLE 2a

Di H$_2$O Solution

| % ionization | Swelling Ratio | | Average (each sample) | Average |
|---|---|---|---|---|
| | 35 min | 60 min | | |
| 10 (a) | 1.9 | 1.4 | 1.6 | 2.9 ± 0.9 |
| (b) | 3.2 | 1.4 | 2.4 | |
| 25 (a) | 84.7 | 80.7 | 82.7 | 80.9 ± 5.9 |
| (b) | 85.8 | 72.7 | 79.1 | |
| 50 (a) | 111.0 | 106.5 | 108.8 | 112.6 ± 5.1 |
| (b) | 118.5 | 114.3 | 116.4 | |
| 75 (a) | 150.7 | 143.8 | 147.3 | 146.4 ± 3.6 |
| (b) | 148.1 | 143.2 | 145.6 | |
| 90 (a) | 245.1 | 245.4 | 245.2 | 257.9 ± 15.3 |
| (b) | 276.2 | 264.8 | 270.5 | |

TABLE 2c 0.17M KCl in H$_2$O Solution

| % ionization | Swelling Ratio | | Average (each sample) | Average |
|---|---|---|---|---|
| | 35 min | 60 min | | |
| 10 (a) | — | — | — | — |
| (b) | — | — | — | |
| 25 (a) | 6.5 | 6.3 | 6.4 | 5.2 ± 1.5 |
| (b) | 4.4 | 3.6 | 4.0 | |
| 50 (a) | 21.6 | 21.7 | 21.7 | 22.4 ± 0.5 |
| (b) | 22.5 | 22.6 | 22.6 | |
| 75 (a) | 36.4 | 36.6 | 36.5 | 36.1 ± 0.5 |
| (b) | 35.5 | 36.0 | 35.8 | |
| 90 (a) | 49.0 | 47.4 | 48.2 | 46.1 ± 0.8 |
| (b) | 47.3 | 48.6 | 48.0 | |

TABLE 2b 0.17M NaCl in H$_2$O Solution

| % ionization | Swelling Ratio | | Average (each sample) | Average |
|---|---|---|---|---|
| | 35 min | 60 min | | |
| 10 (a) | — | — | — | — |
| (b) | — | — | — | |
| 25 (a) | 9.5 | 8.5 | 9.0 | 10.4 ± 1.7 |
| (b) | 12.2 | 11.5 | 11.9 | |
| 50 (a) | 16.6 | 13.0 | 14.7 | 15.8 ± 1.9 |
| (b) | 17.0 | 16.9 | 17.0 | |
| 75 (a) | 36.4 | 37.6 | 37.0 | 36.4 ± 0.8 |
| (b) | 36.0 | 35.8 | 35.9 | |
| 90 (a) | 53.1 | 52.3 | 52.7 | 51.9 ± 1.0 |
| (b) | 51.4 | 50.8 | 51.1 | |

The percent ionization is indicative of NaOH equivalents to isoprenecarboxylic acid of the initial polymerization solution.

One step preparation of hydrogel monomer feed.

Single step preparation of mixtures of acid 6-H and its carboxylate salt 6-M (M=Li, Na, K) that are suitable as a monomer feed for direct use in hydrogel polymerization procedure described above could also be prepared. Namely, the lactone 3 could be opened, for example, with one molar equivalent of Metal-tert-butoxide (Metal=lithium, sodium, or potassium) in tert-butanol or THF as solvent to produce the carboxylate salt 6-M. This mixture could be treated with a mineral acid like aqueous HCl, H$_2$SO$_4$, or HNO$_3$, for example, using molar ratios varying from 0.1 to 0.9 relative to the salt 6-M. The solvent composition could be adjusted, as needed, to precipitate the mixture of 6-H/6-M, which could be used in the same fashion as described above.

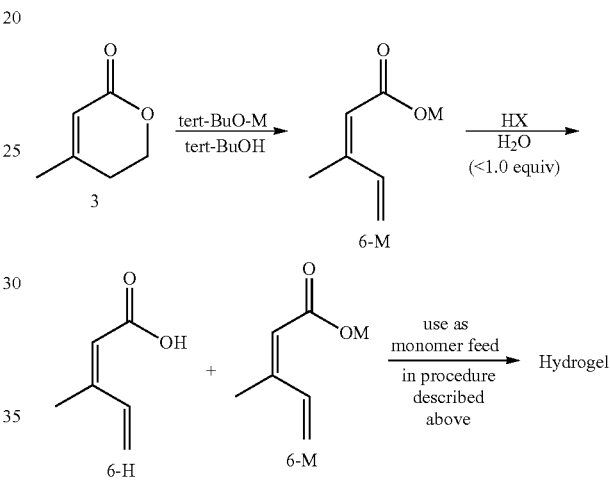

Figure 19:
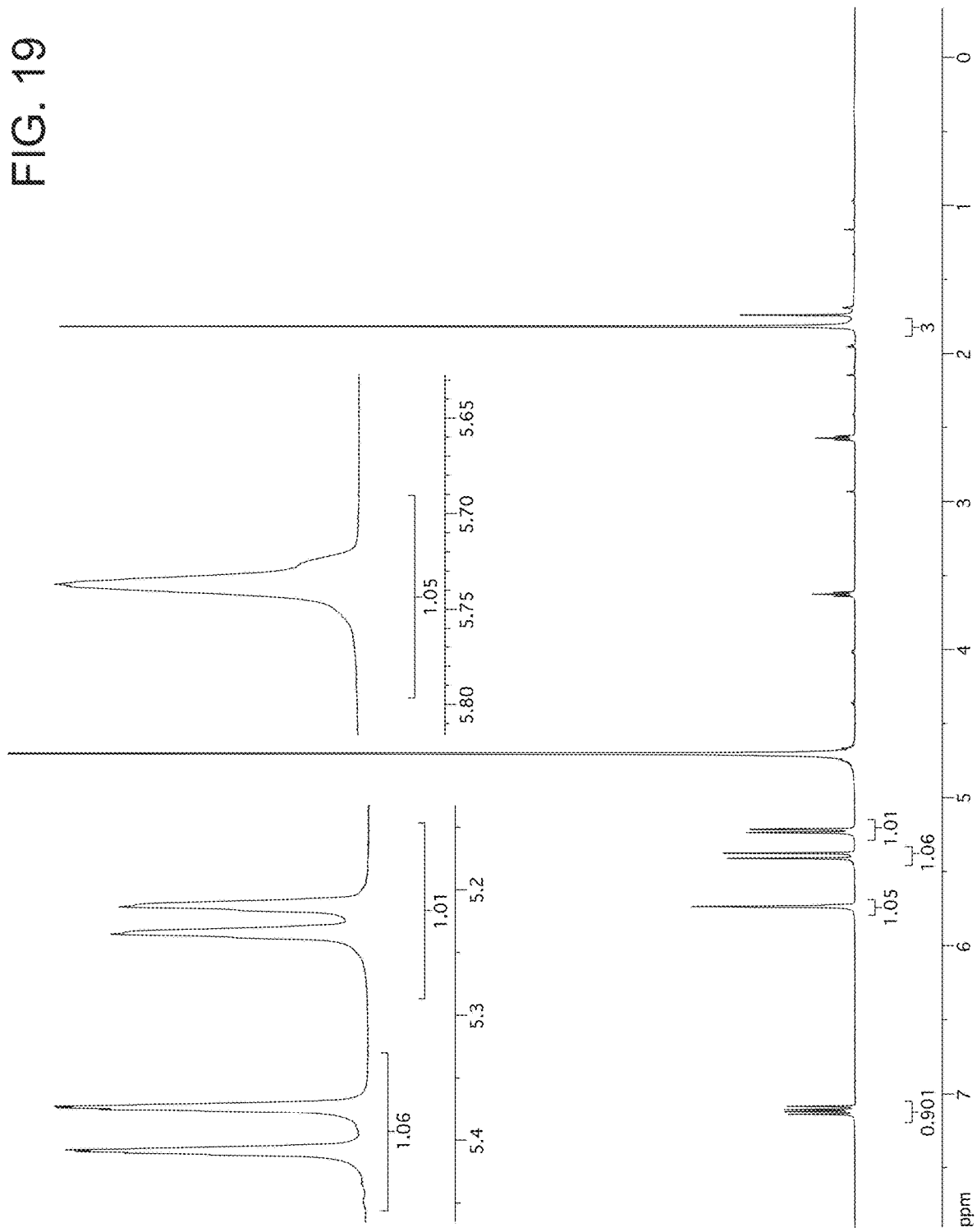
FIG. 19 shows $^1$H NMR of potassium (Z)-3-methylpenta-2,4-dienoate (6-K).
Figure 20:
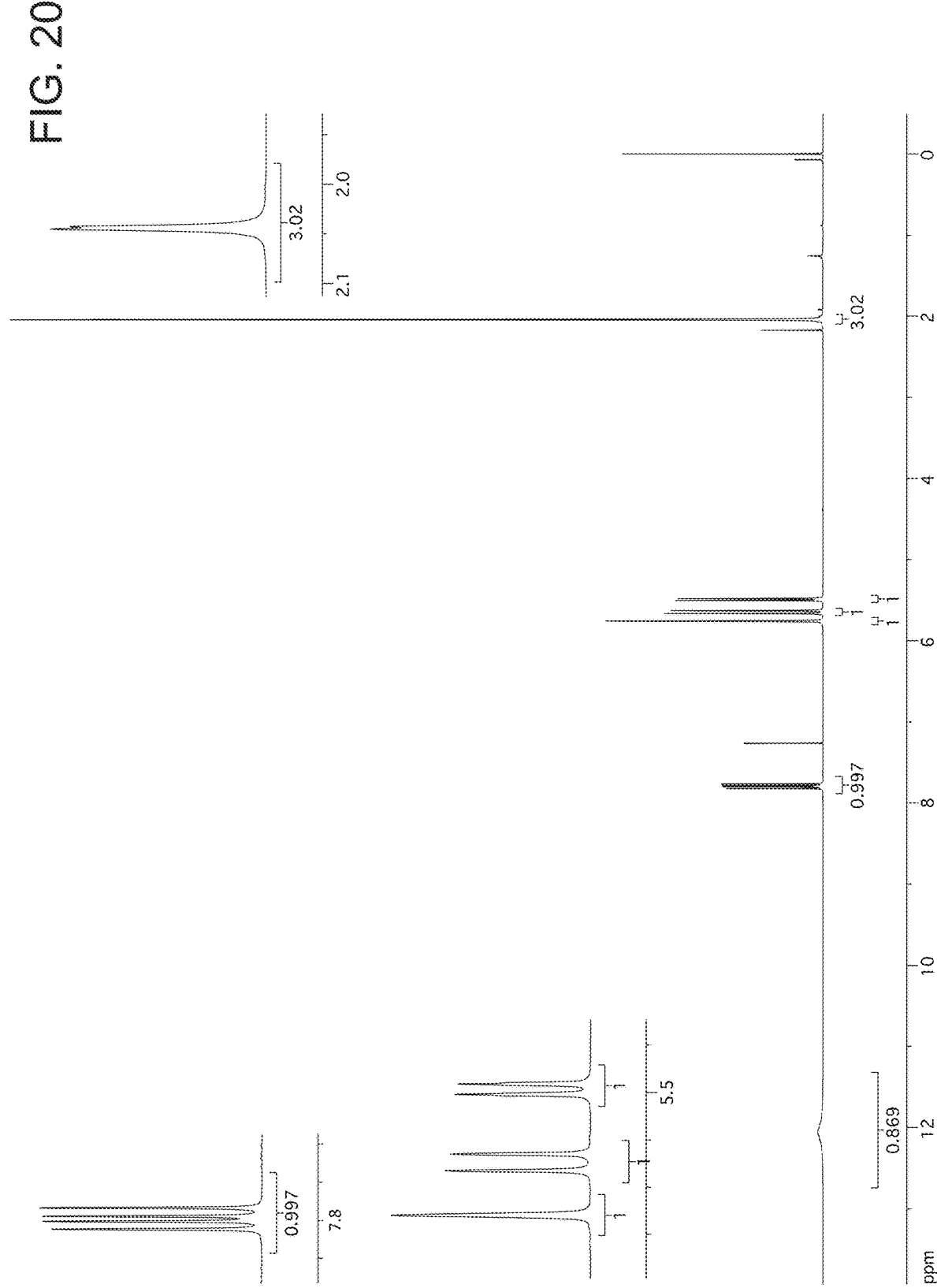
FIGS. 20 and 21 show $^1$H and $^{13}$C NMR of isoprenecarboxylic acid (6-H).
Figure 21:
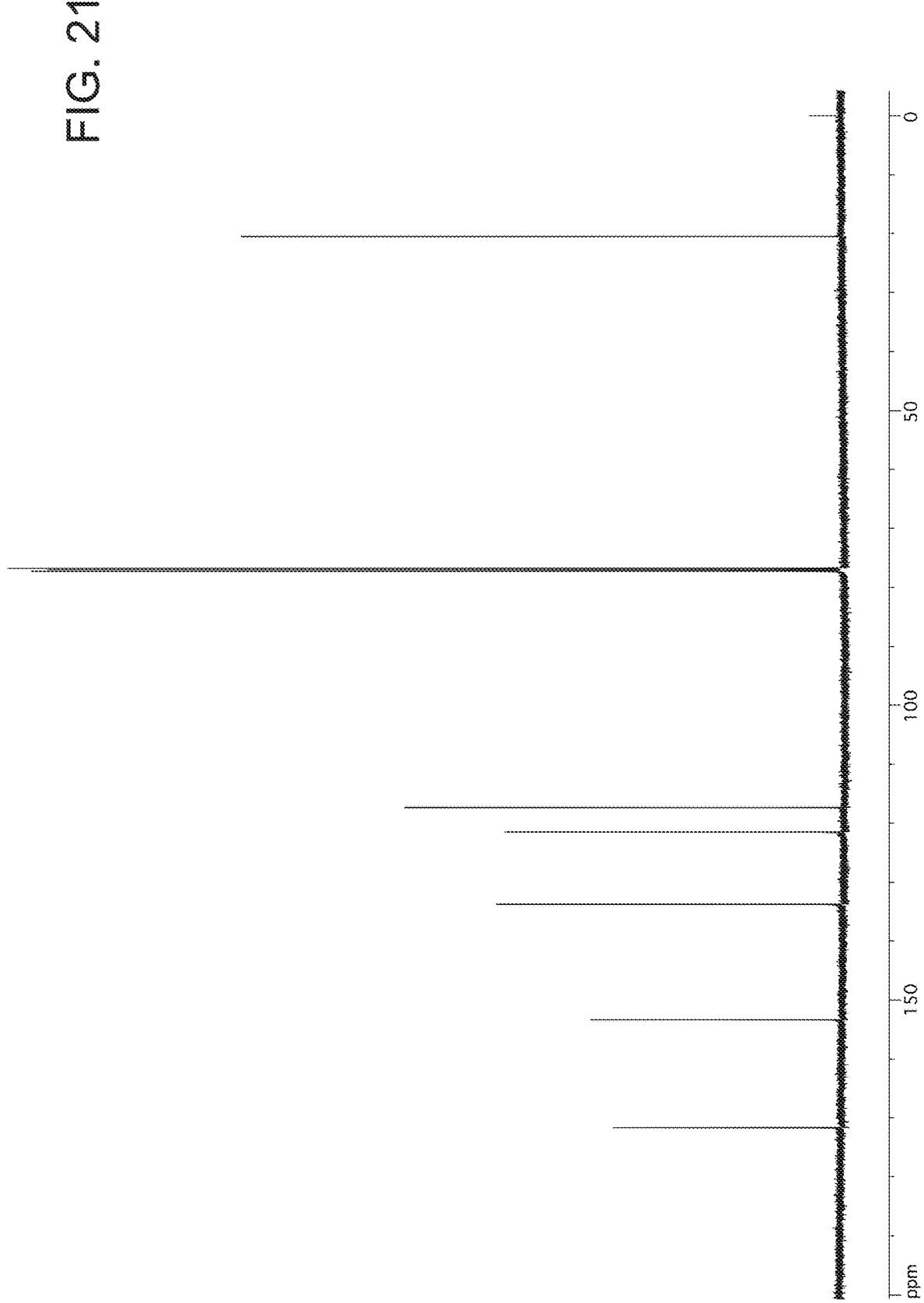
Figure 22:
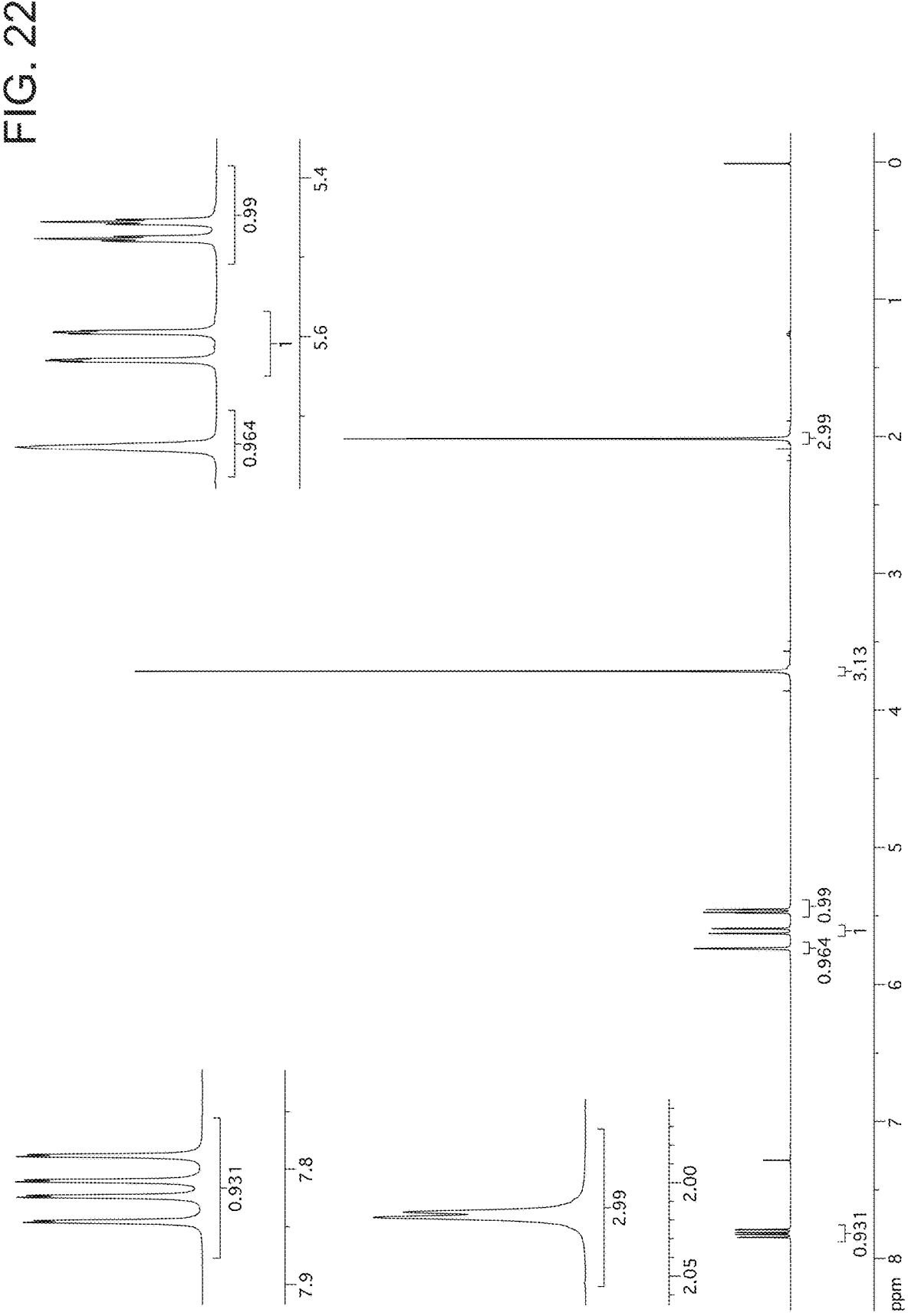
FIGS. 22 and 23 show $^1$H and $^{13}$C NMR of methyl (Z)-3-methylpenta-2,4-dienoate (6-Me).
Figure 23:
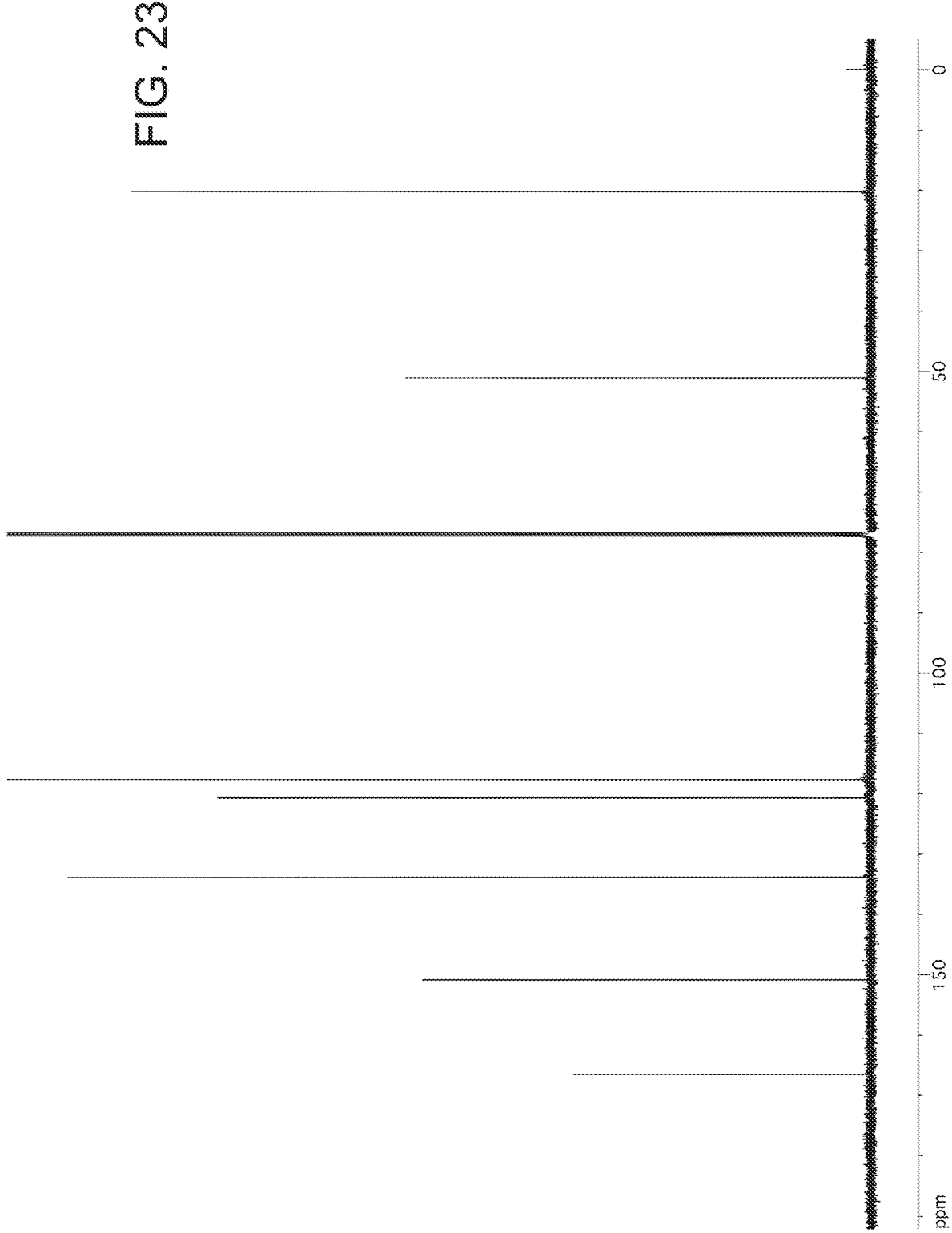
Figure 24:
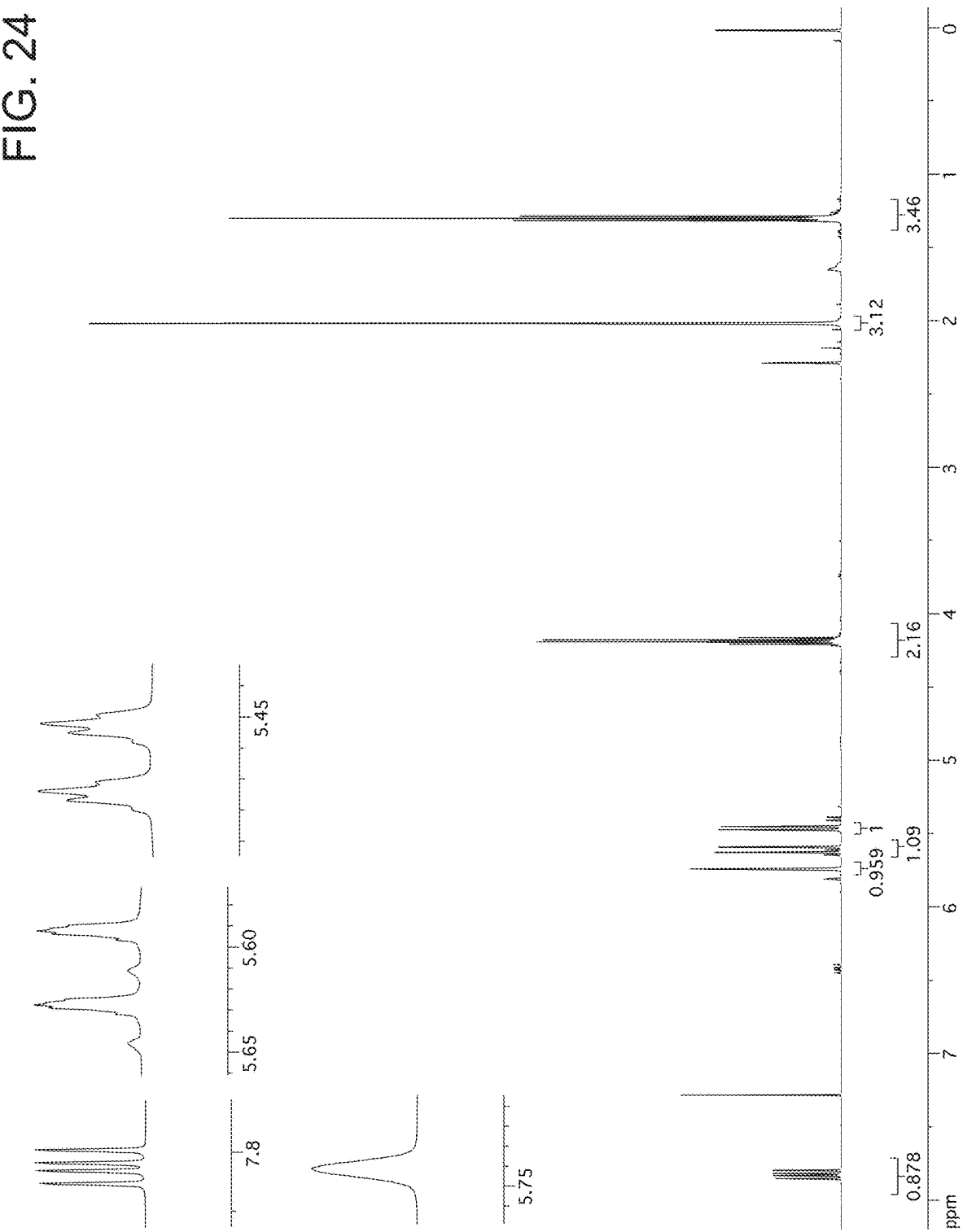
FIGS. 24 and 25 show $^1$H and $^{13}$C NMR of ethyl (Z)-3-methylpenta-2,4-dienoate (6-Et).
Figure 25:
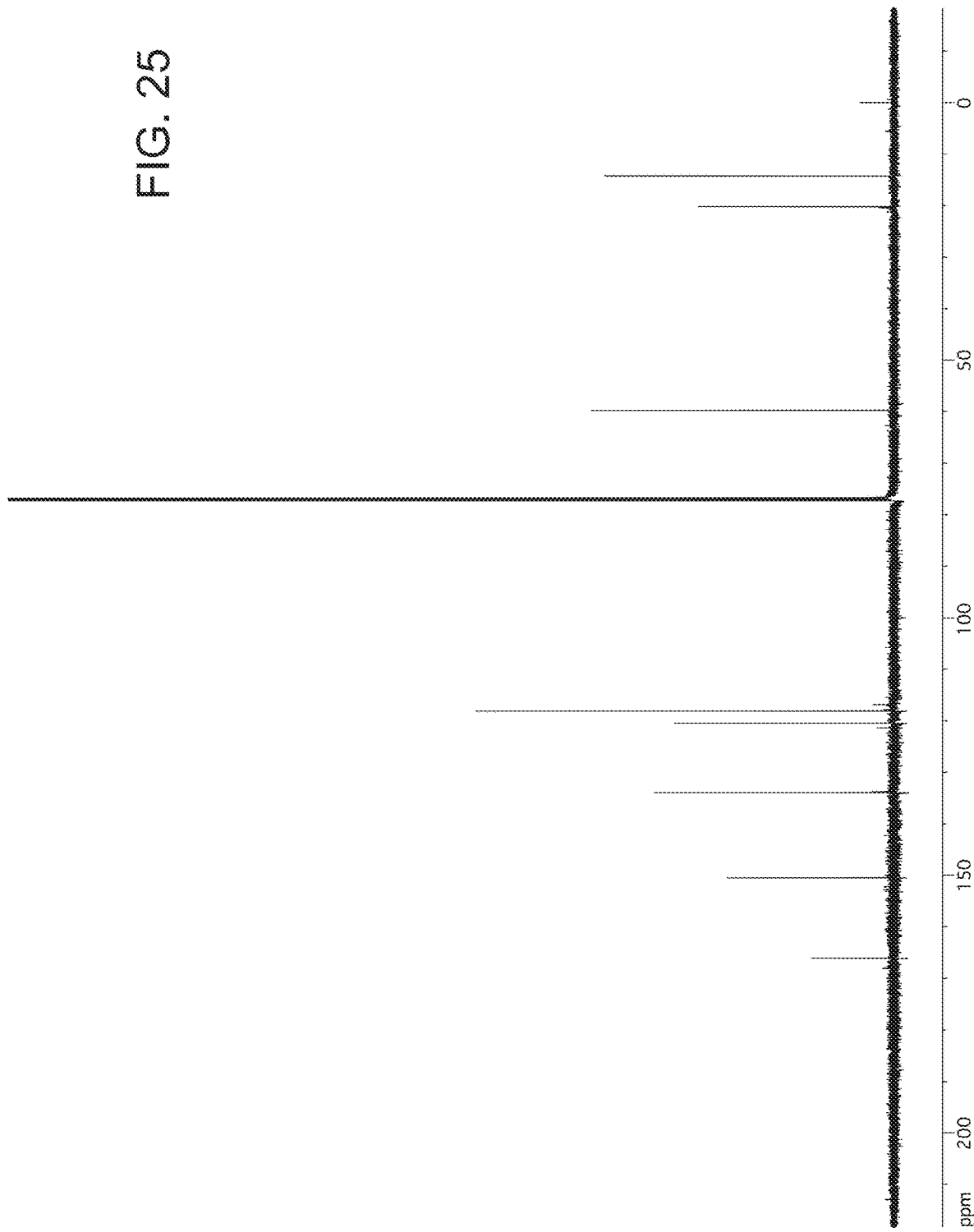
Figure 26:
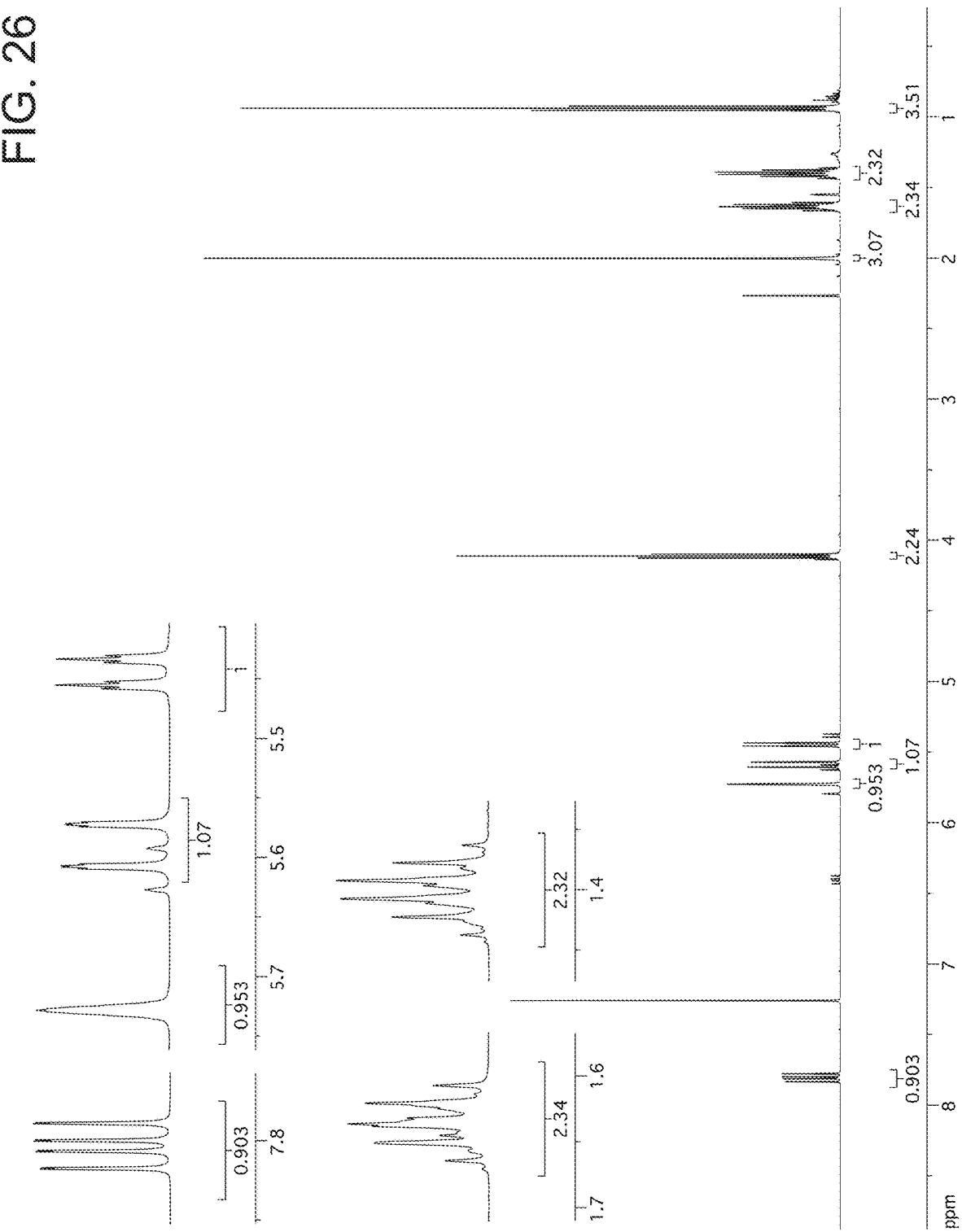
FIGS. 26 and 27 show $^1$H and $^{13}$C NMR of butyl (Z)-3-methylpenta-2,4-dienoate (6-"Bu).
Figure 27:
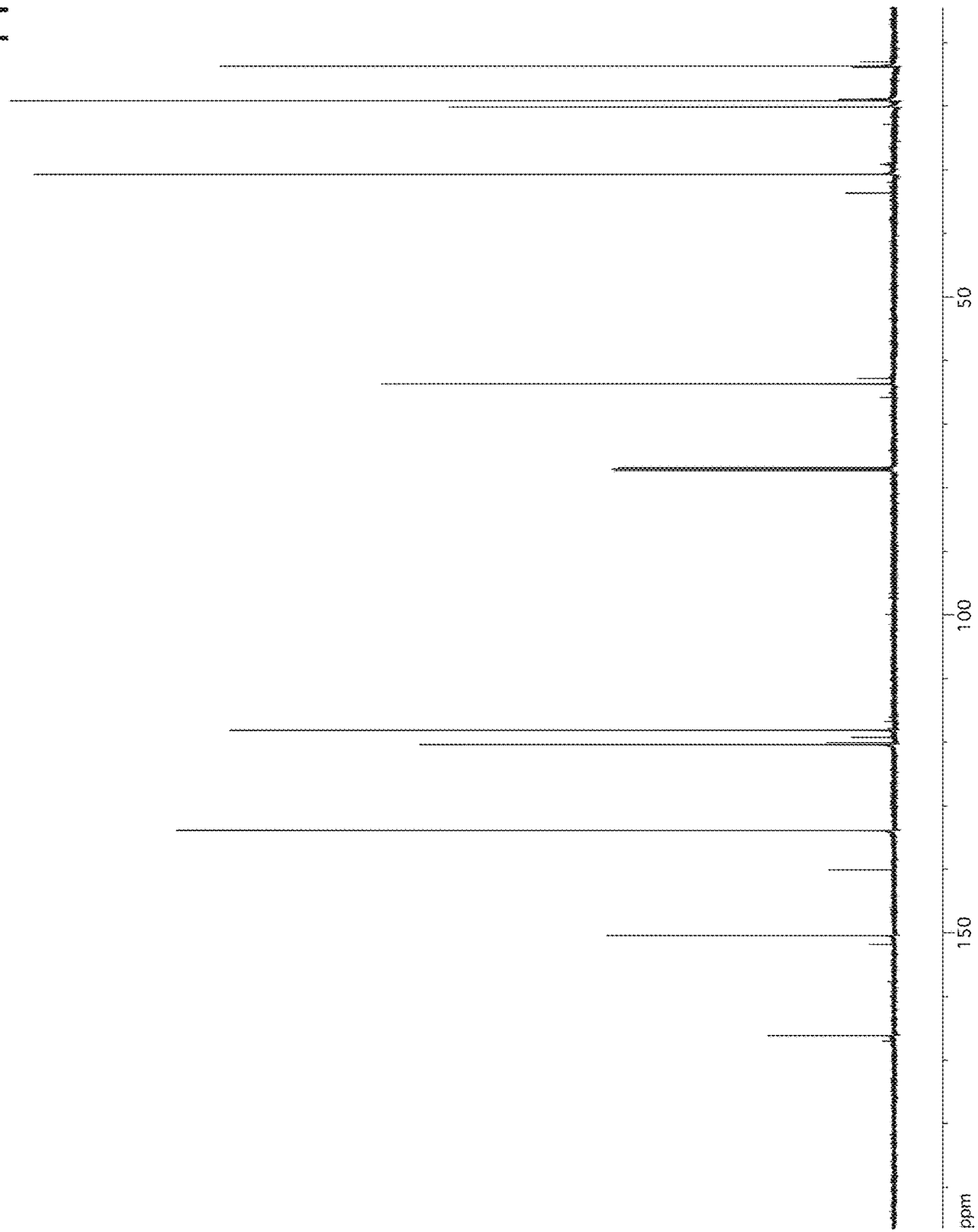
Figure 28:
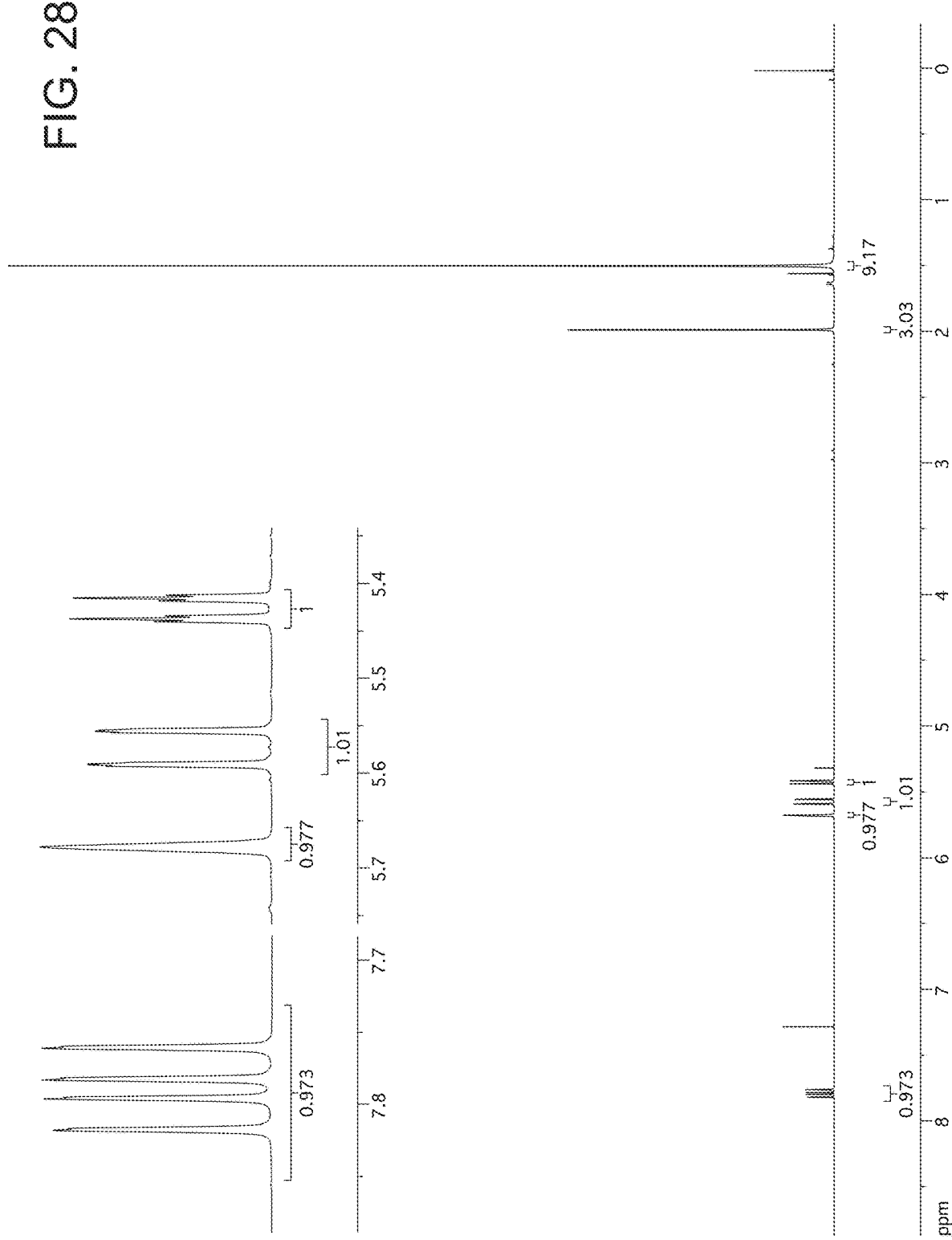
FIGS. 28 and 29 show $^1$H and $^{13}$C NMR of tert-Butyl (Z)-3-Methylpenta-2,4-dienoate (6-$^t$Bu).
Figure 29:
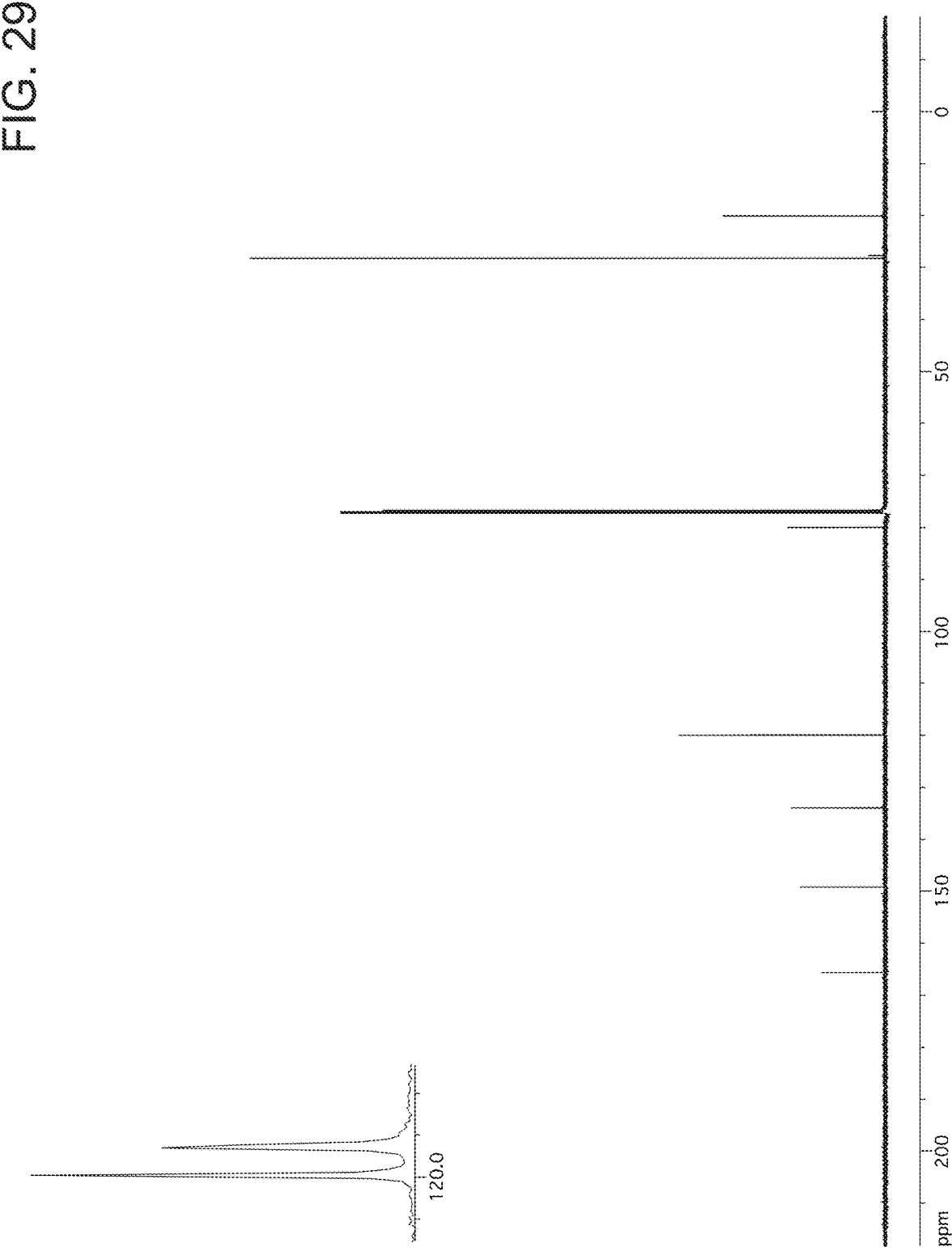
Figure 30:
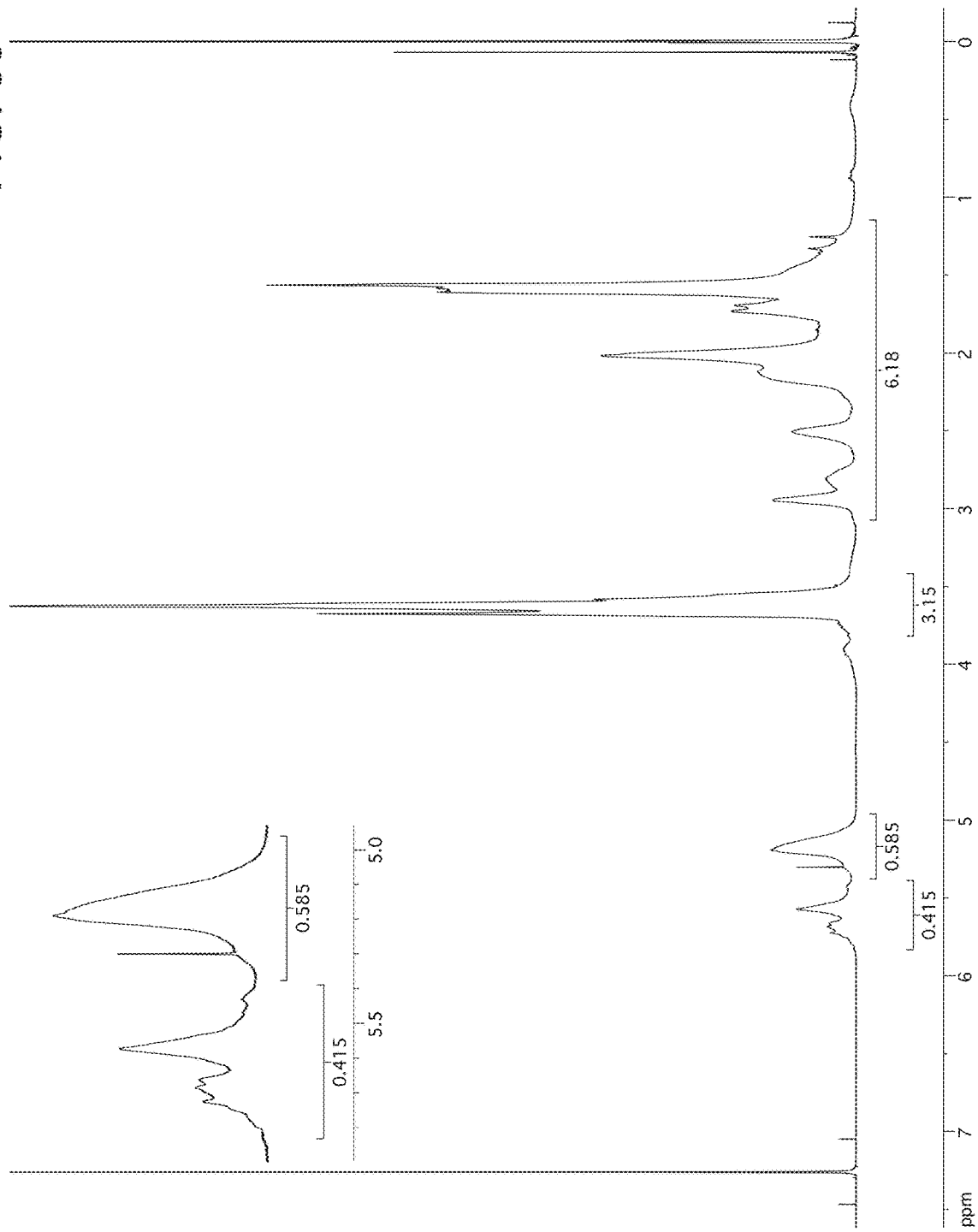
FIGS. 30 and 31 show $^1$H and $^{13}$C NMR of poly(methyl isoprenecarboxylate) (PMIC).
Figure 31:
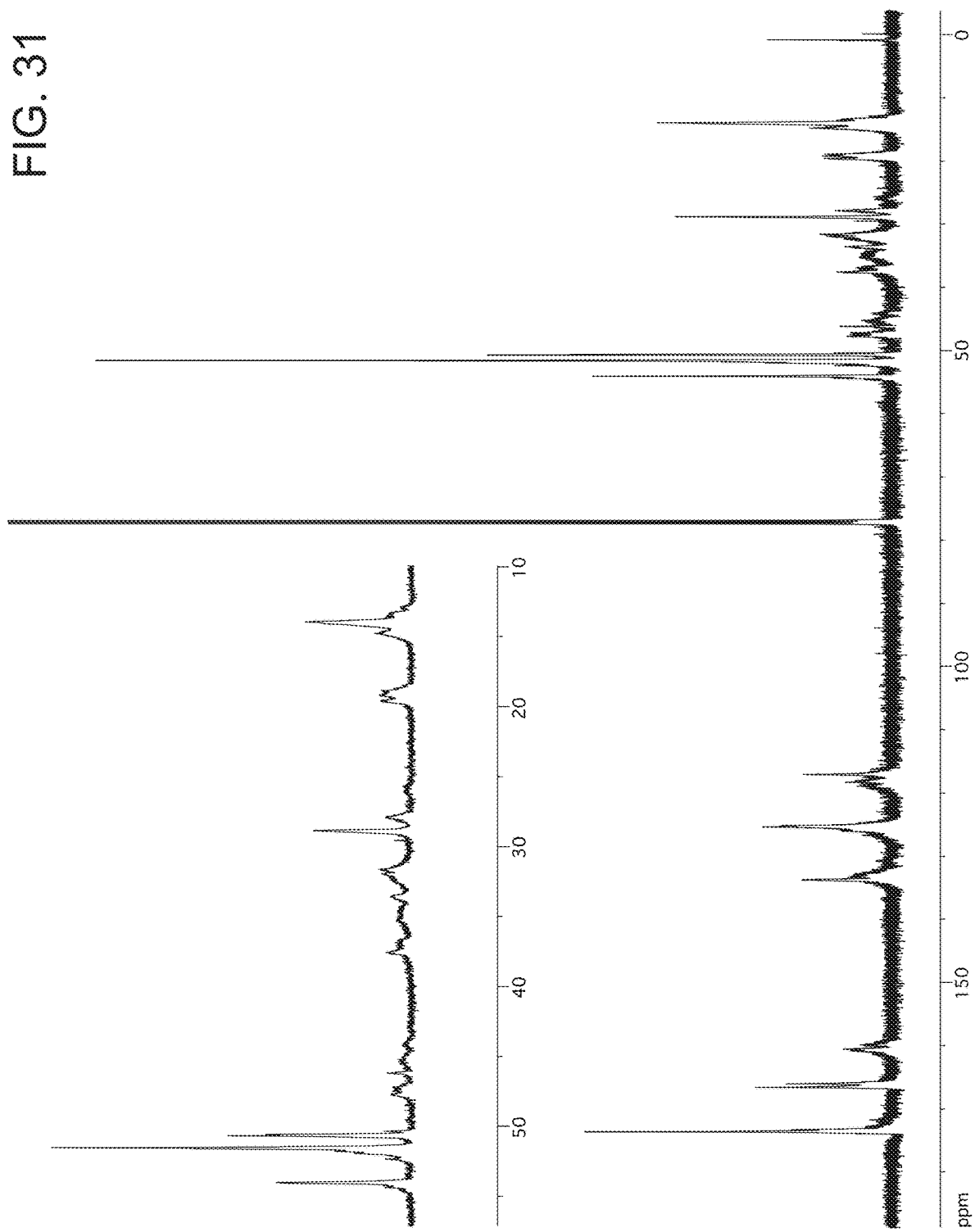
Figure 32:
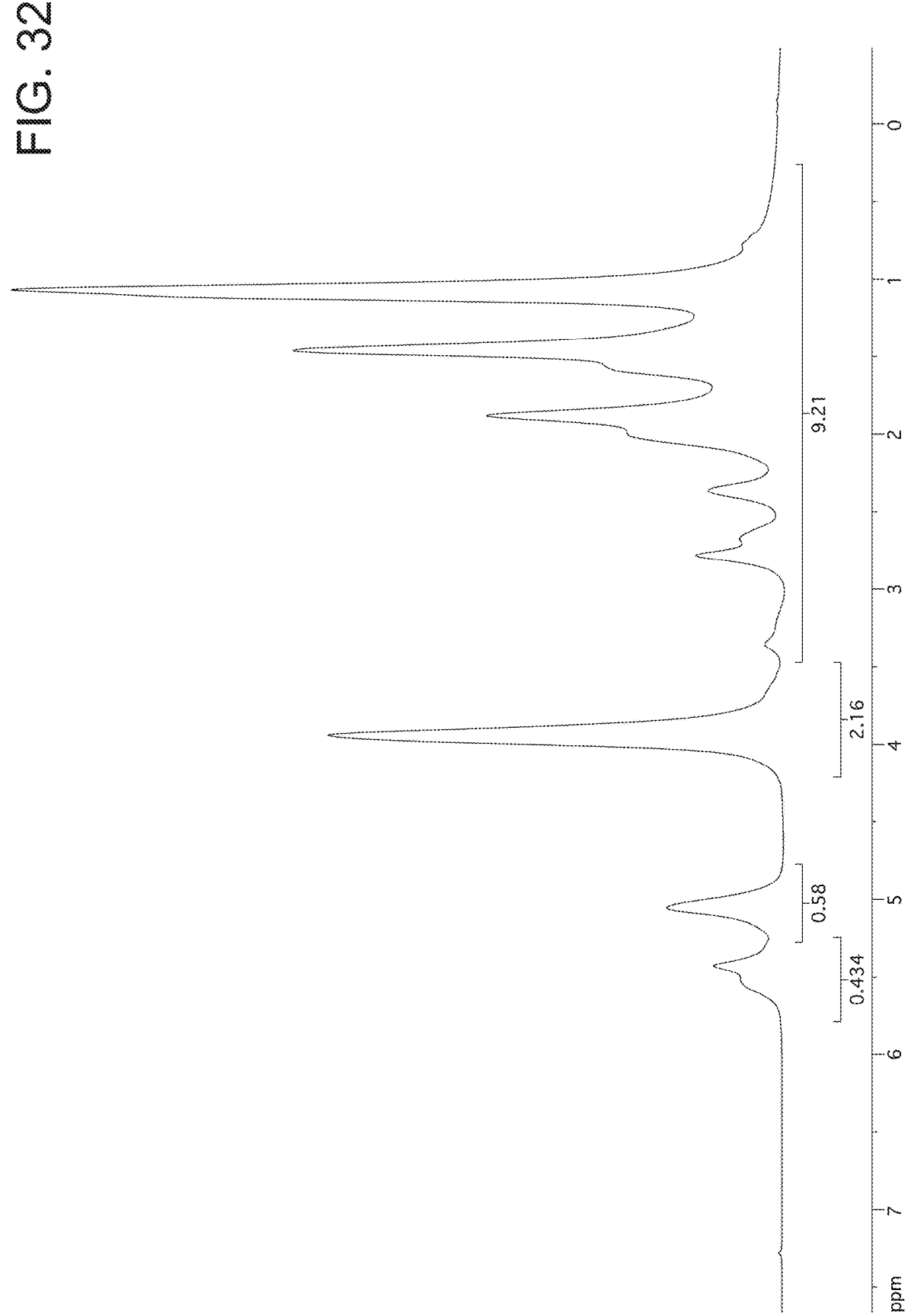
FIGS. 32 and 33 show $^1$H and $^{13}$C NMR of poly(ethyl isoprenecarboxylate) (PEIC).
Figure 33:
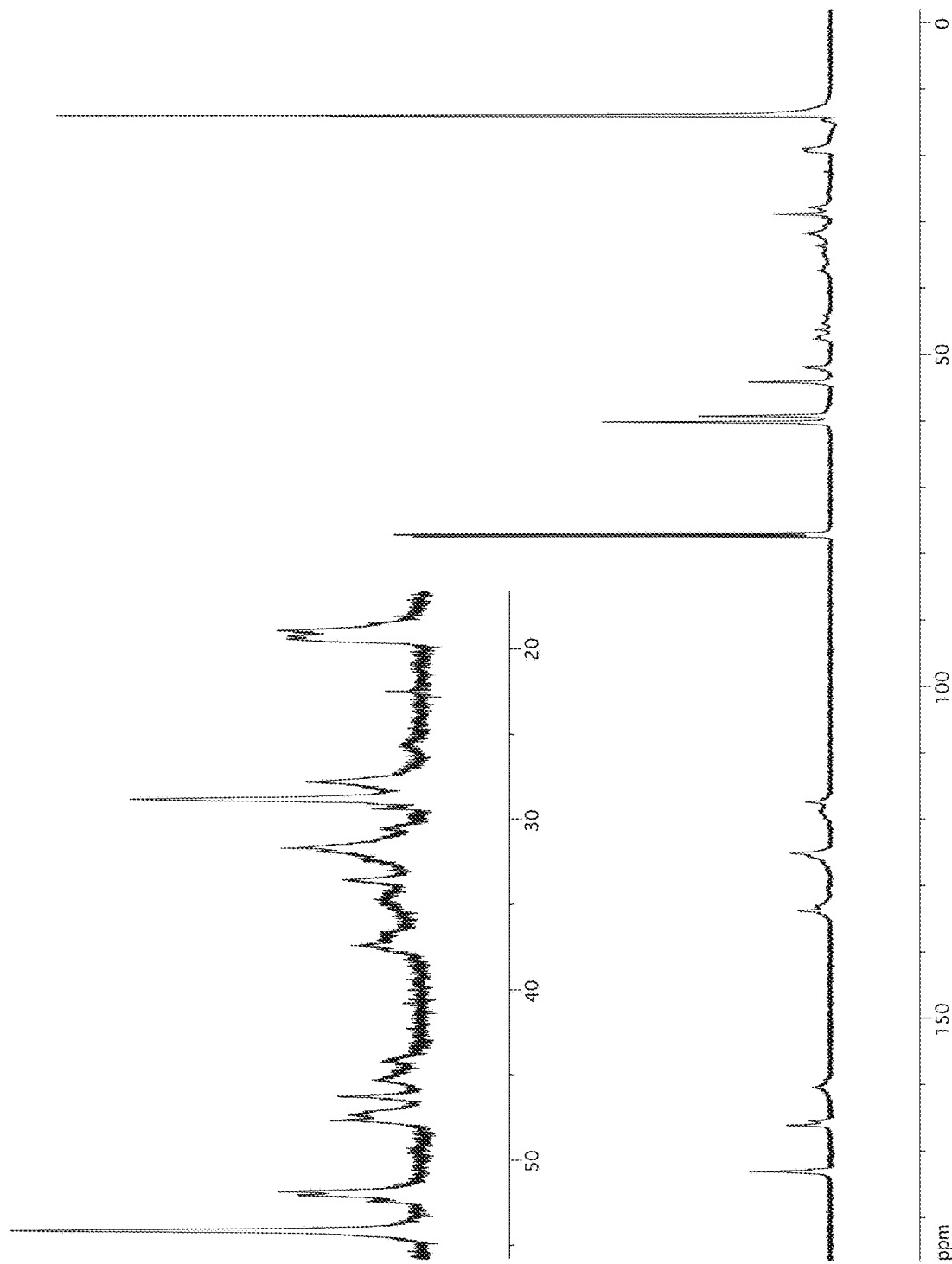
Figure 34:
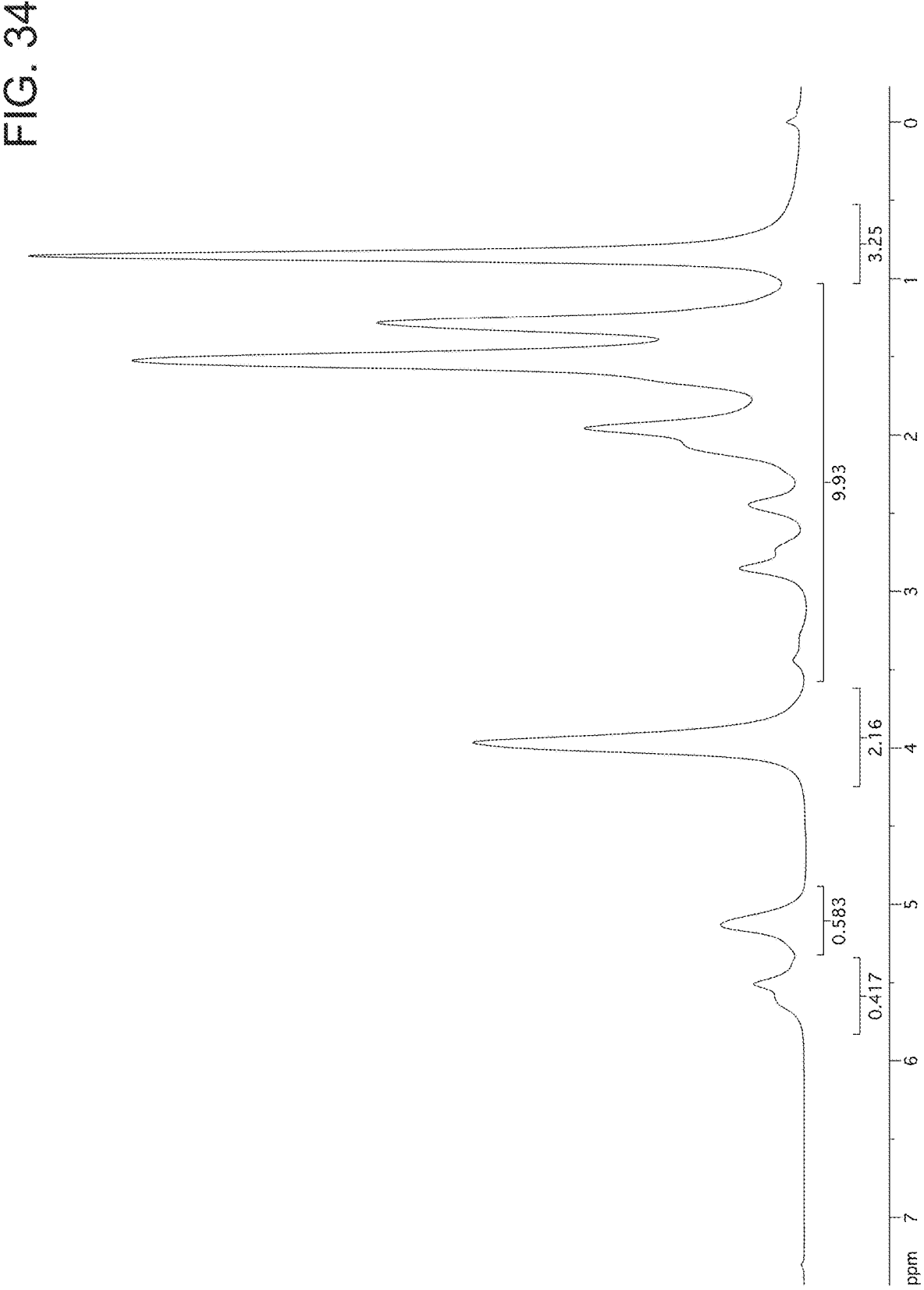
FIGS. 34 and 35 show $^1$H and $^{13}$C NMR of poly(n-butyl isoprenecarboxylic acid) (P"BIC).
Figure 35:
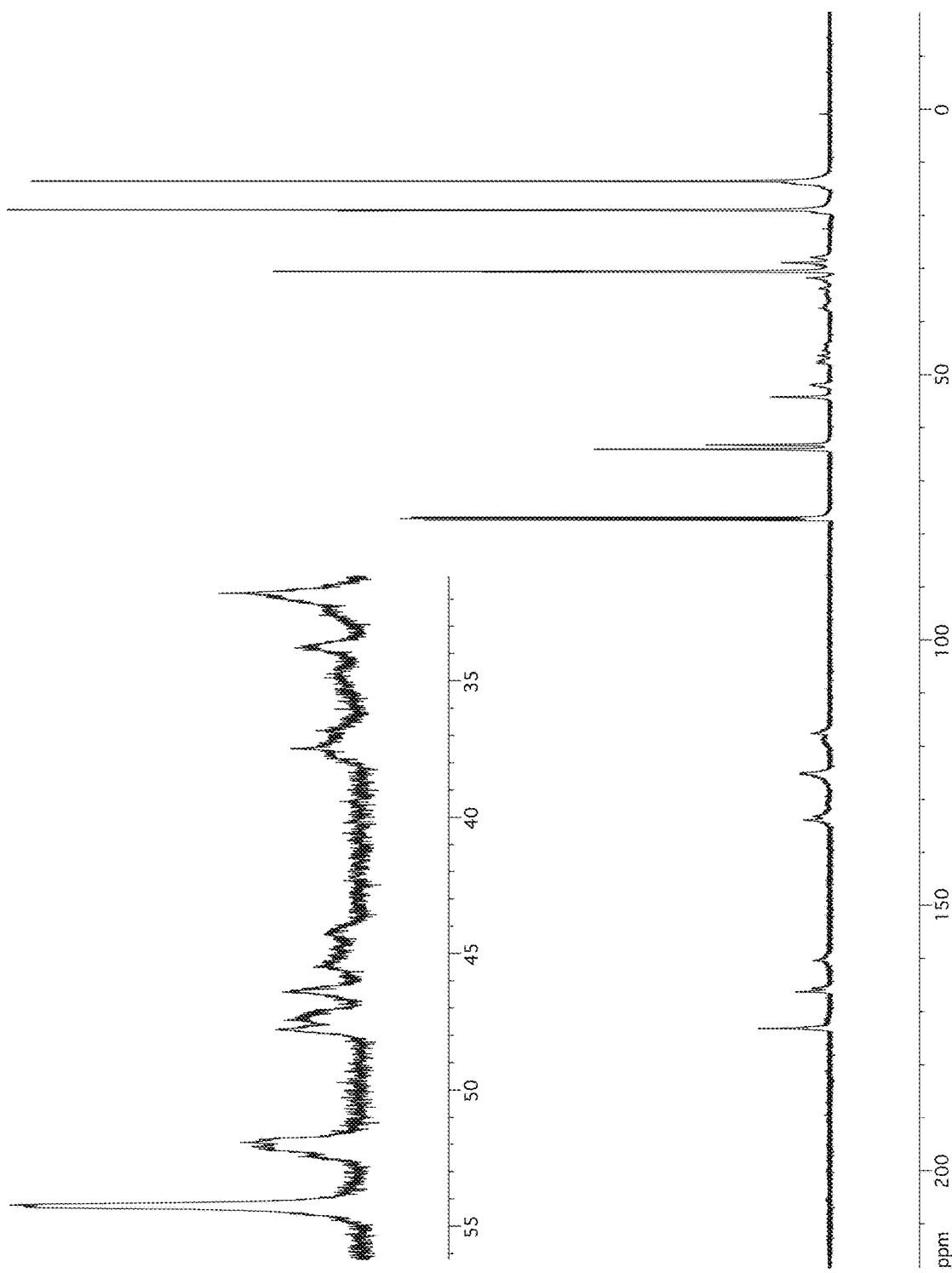
Figure 36:
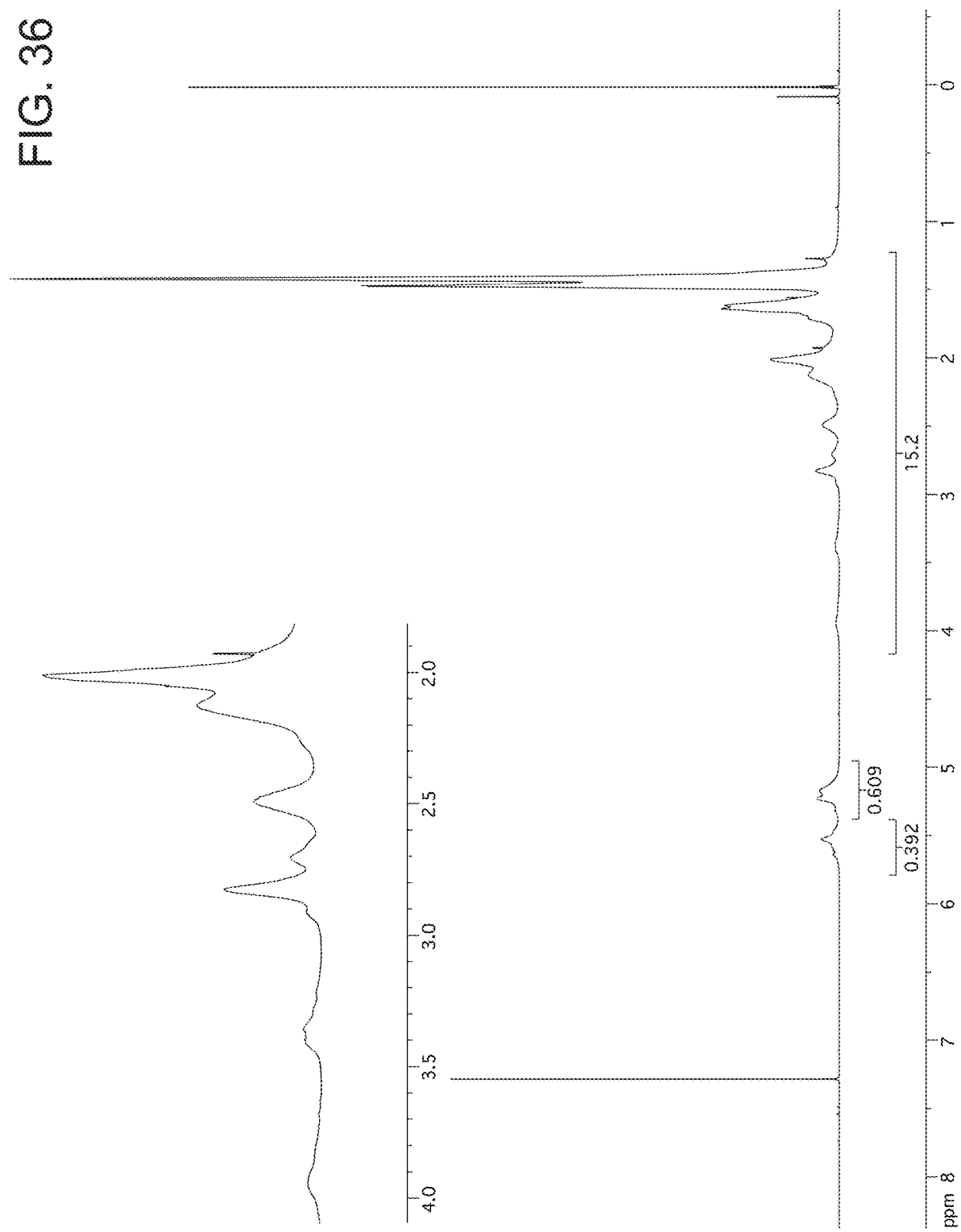
FIGS. 36 and 37 show $^1$H and $^{13}$C NMR of poly(t-butyl ester isoprenecarboxylate) (P$^t$BIC).
Figure 37:
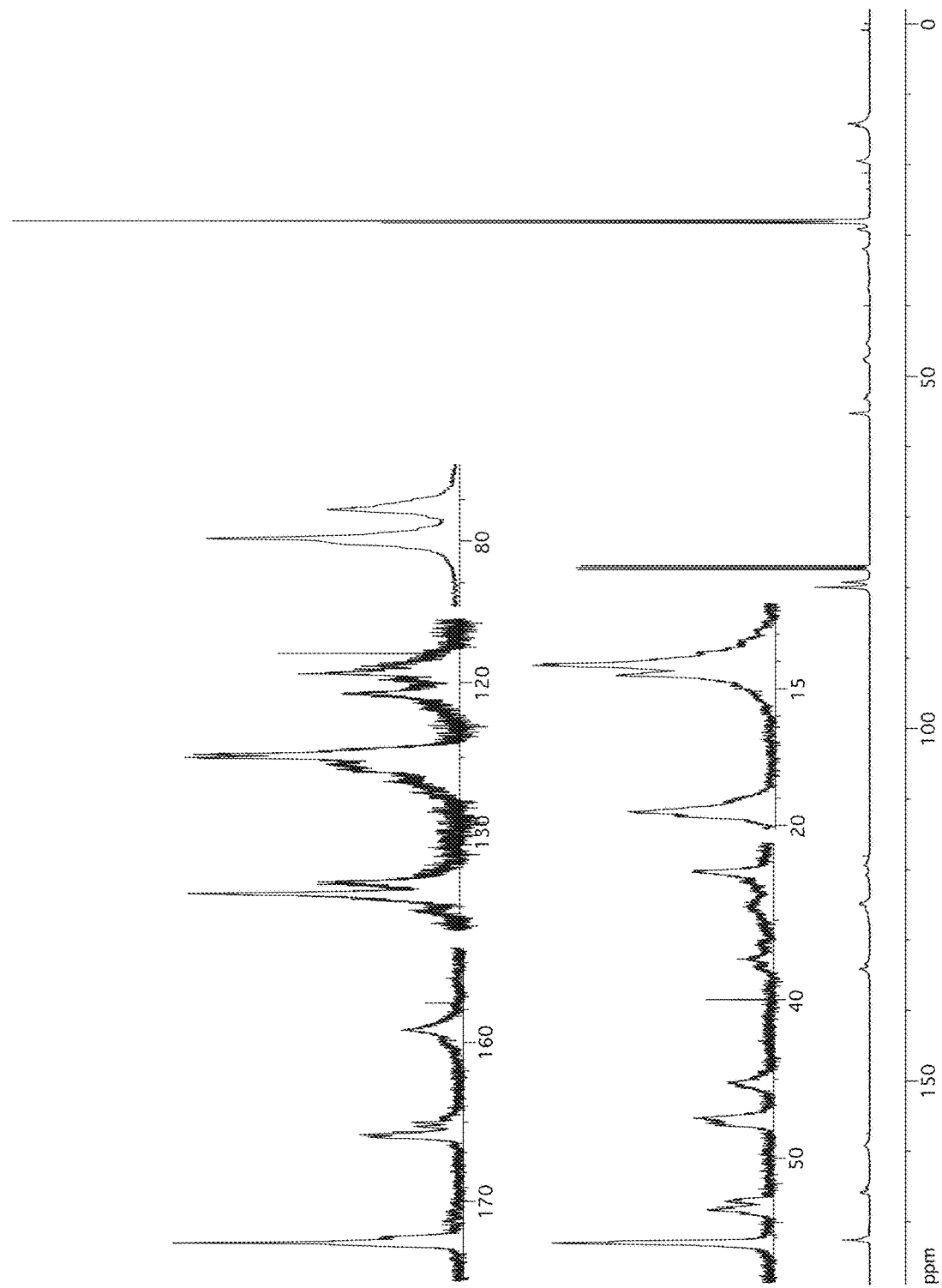

FIG. 19 shows $^1$H NMR of potassium (Z)-3-methylpenta-2,4-dienoate (6-K). FIGS. 20 and 21 show $^1$H and $^{13}$C NMR of isoprenecarboxylic acid (6-H). FIGS. 22 and 23 show $^1$H and $^{13}$C NMR of methyl (Z)-3-methylpenta-2,4-dienoate (6-Me). FIGS. 24 and 25 show $^1$H and $^{13}$C NMR of ethyl (Z)-3-methylpenta-2,4-dienoate (6-Et). FIGS. 26 and 27 show $^1$H and $^{13}$C NMR of butyl (Z)-3-methylpenta-2,4-dienoate (6-$^n$Bu). FIGS. 28 and 29 show $^1$H and $^{13}$C NMR of tert-Butyl (Z)-3-Methylpenta-2,4-dienoate (6-$^t$Bu). FIGS. 30 and 31 show $^1$H and $^{13}$C NMR of poly(methyl isoprenecarboxylate) (PMIC). FIGS. 32 and 32 show $^1$H and $^{13}$C NMR of poly(ethyl isoprenecarboxylate) (PEIC). FIGS. 34 and 35 show $^1$H and $^{13}$C NMR of poly(n-butyl isoprenecarboxylic acid) (P$^n$BIC). FIGS. 36 and 37 show $^1$H and $^{13}$C NMR of poly(t-butyl ester isoprenecarboxylate) (P$^t$BIC).

Thus, embodiments of monomers and polymers formed thereby are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The invention claimed is:

1. A polymer formed from one or more monomers of formula I

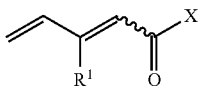 (I)

wherein $R^1$ is a $C_1$ to $C_4$ alkyl; and

X is —$OR^2$ where $R^2$ is a $C_1$ to $C_4$ alkyl, 2-ethylhexyl, or a hydrocarbon moiety of bio-renewable alcohol or a hydrogenated derivative thereof.

2. The polymer according to claim 1, wherein $R^1$ is a methyl group, an ethyl group, a propyl group, an n-butyl group, or a t-butyl group.

3. The polymer according to claim 1, wherein $R^2$ is a $C_1$ to $C_4$ alkyl.

4. The polymer according to claim 1, wherein $R^2$ is 2-ethylhexyl.

5. The polymer according to claim 1, wherein $R^2$ is a hydrocarbon moiety of bio-renewable alcohol or a hydrogenated derivative thereof.

6. The polymer according to claim 1, wherein the monomer according to formula I is polymerized with a secondary monomer not of formula I.

7. The polymer according to claim 1, wherein the monomer of formula I is co-polymerized with the acid of the monomer of formula I.

8. The polymer according to claim 1, wherein the polymer is crosslinked.

9. The polymer according to claim 1, wherein the polymer is a hydrogel and can hold at least about 100 times its weight in water.

10. The polymer according to claim 6, wherein the secondary monomer is selected from isoprene, butadiene, styrene, sorbic acid (or its alkali metal salts), a sorbate ester, (meth)acrylic acid (or its alkali metal salts), (meth)acrylate ester, or combinations thereof.

* * * * *